(12) United States Patent
Danitz et al.

(10) Patent No.: US 9,085,085 B2
(45) Date of Patent: *Jul. 21, 2015

(54) ARTICULATING MECHANISMS WITH ACTUATABLE ELEMENTS

(71) Applicant: Intuitive Surgical Operations, Inc., Sunnyvale, CA (US)

(72) Inventors: David J. Danitz, San Jose, CA (US); Adam Gold, Scarsdale, NY (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/012,489

(22) Filed: Aug. 28, 2013

(65) Prior Publication Data

US 2013/0340559 A1    Dec. 26, 2013

Related U.S. Application Data

(60) Continuation of application No. 12/766,820, filed on Apr. 23, 2010, now Pat. No. 8,535,347, which is a division of application No. 12/109,333, filed on Apr. 24, 2008, which is a continuation of application No.

(Continued)

(51) Int. Cl.
*A61B 17/28* (2006.01)
*B25J 18/06* (2006.01)
(Continued)

(52) U.S. Cl.
CPC ............... *B25J 18/06* (2013.01); *A61B 1/0053* (2013.01); *A61B 1/0055* (2013.01);
(Continued)

(58) Field of Classification Search
CPC .... A61B 1/0051; A61B 1/0057; A61B 1/008; A61B 2017/00305; A61B 2017/00314; A61B 2017/00318; A61B 2017/00323; B25J 18/06; B25J 9/104

USPC ........... 600/141, 142, 144, 146, 148, 149; 606/1, 108, 141; 604/528
See application file for complete search history.

(56) References Cited

U.S. PATENT DOCUMENTS 1,820,463 A    8/1931    Klein
3,060,972 A    10/1962   Sheldon
(Continued)

FOREIGN PATENT DOCUMENTS

EP    165718 A2    12/1985
EP    0598618 A2    5/1994
(Continued)

OTHER PUBLICATIONS

Cox J., "The minimally invasive Maze-III procedure; Operative Techniques in Thoracic and Cardiovascular Surgery," 2000, vol. 5, Issue 1, pp. 79-92.
(Continued)

*Primary Examiner* — Ryan Severson

(57) ABSTRACT

The invention provides an articulating mechanism useful, for example, for remote manipulation of various surgical instruments and diagnostic tools within, or to, regions of the body. Movement of segments at the proximal end of the mechanism results in a corresponding, relative movement of segments at the distal end of the mechanism. The proximal and distal segments are connected by a set of cables in such a fashion that each proximal segment forms a discrete pair with a distal segment. This configuration allows each segment pair to move independently of one another and also permits the articulating mechanism to undergo complex movements and adopt complex configurations. The articulating mechanisms may also be combined in such a way to remotely mimic finger movements for manipulation of an object or body tissue.

18 Claims, 40 Drawing Sheets

Related U.S. Application Data

10/997,249, filed on Nov. 24, 2004, now Pat. No. 7,410,483, which is a continuation-in-part of application No. 10/444,769, filed on May 23, 2003, now Pat. No. 7,090,637.

(51) Int. Cl.

| | | |
|---|---|---|
| *A61B 1/005* | (2006.01) | |
| *A61B 17/072* | (2006.01) | |
| *A61B 19/00* | (2006.01) | |
| *B25J 9/06* | (2006.01) | |
| *B25J 9/10* | (2006.01) | |
| *B25J 13/02* | (2006.01) | |
| *A61B 18/14* | (2006.01) | |
| *A61B 17/00* | (2006.01) | |
| *A61B 17/29* | (2006.01) | |

(52) U.S. Cl.
CPC ........ *A61B 17/072* (2013.01); *A61B 17/07207* (2013.01); *A61B 19/22* (2013.01); *B25J 9/06* (2013.01); *B25J 9/104* (2013.01); *B25J 13/02* (2013.01); *A61B 18/1492* (2013.01); *A61B 2017/00323* (2013.01); *A61B 2017/00424* (2013.01); *A61B 2017/00438* (2013.01); *A61B 2017/2905* (2013.01); *A61B 2017/2927* (2013.01); *A61B 2019/2238* (2013.01); *A61B 2019/2242* (2013.01); *A61B 2019/2296* (2013.01); *Y10S 901/21* (2013.01); *Y10T 74/20323* (2015.01); *Y10T 74/20402* (2015.01)

(56) References Cited

U.S. PATENT DOCUMENTS

| | | |
|---|---|---|
| 3,071,161 A | 1/1963 | Ulrich |
| 3,190,286 A | 6/1965 | Stokes |
| 3,557,780 A | 1/1971 | Sato |
| 3,605,725 A | 9/1971 | Bentov |
| 4,246,661 A | 1/1981 | Pinson |
| 4,466,649 A | 8/1984 | Ozawa |
| 4,489,826 A | 12/1984 | Dubson |
| 4,551,061 A | 11/1985 | Olenick |
| 4,566,843 A | 1/1986 | Iwatsuka et al. |
| 4,580,551 A | 4/1986 | Siegmund et al. |
| 4,700,693 A | 10/1987 | Lia et al. |
| 4,763,669 A | 8/1988 | Jaeger |
| 4,790,294 A | 12/1988 | Allred, III |
| 4,834,761 A | 5/1989 | Walters |
| 4,838,859 A | 6/1989 | Strassmann |
| 4,854,626 A | 8/1989 | Duke |
| 4,873,965 A | 10/1989 | Danieli |
| 4,880,015 A | 11/1989 | Nierman |
| 4,921,293 A | 5/1990 | Ruoff et al. |
| 4,984,951 A | 1/1991 | Jameson |
| 5,143,505 A | 9/1992 | Burdea et al. |
| 5,158,086 A | 10/1992 | Brown et al. |
| 5,174,276 A | 12/1992 | Crockard |
| 5,209,747 A | 5/1993 | Knoepfler |
| 5,251,611 A | 10/1993 | Zehel et al. |
| 5,257,618 A | 11/1993 | Kondo |
| 5,271,381 A | 12/1993 | Ailinger et al. |
| 5,273,026 A | 12/1993 | Wilk |
| 5,286,228 A | 2/1994 | Lee et al. |
| 5,297,443 A | 3/1994 | Wentz |
| 5,314,424 A | 5/1994 | Nicholas |
| 5,322,064 A | 6/1994 | Lundquist |
| 5,325,845 A | 7/1994 | Adair |
| 5,330,502 A | 7/1994 | Hassler et al. |
| 5,354,162 A | 10/1994 | Burdea et al. |
| 5,373,747 A | 12/1994 | Ogawa et al. |
| 5,381,782 A | 1/1995 | DeLaRama et al. |
| 5,403,342 A | 4/1995 | Tovey et al. |
| 5,405,344 A | 4/1995 | Williamson et al. |
| 5,425,743 A | 6/1995 | Nicholas |
| 5,441,494 A | 8/1995 | Ortiz |
| 5,454,827 A | 10/1995 | Aust et al. |
| 5,476,479 A | 12/1995 | Green et al. |
| 5,486,154 A | 1/1996 | Kelleher |
| 5,490,819 A | 2/1996 | Nicholas et al. |
| 5,498,256 A | 3/1996 | Furnish |
| 5,513,827 A | 5/1996 | Michelson |
| 5,520,678 A | 5/1996 | Heckele et al. |
| 5,522,788 A | 6/1996 | Kuzmak |
| 5,549,636 A | 8/1996 | Li |
| 5,562,699 A | 10/1996 | Heimberger et al. |
| 5,570,919 A | 11/1996 | Eusebe |
| 5,599,151 A | 2/1997 | Daum et al. |
| 5,609,601 A | 3/1997 | Kolesa et al. |
| 5,618,294 A | 4/1997 | Aust et al. |
| 5,620,415 A | 4/1997 | Lucey et al. |
| 5,624,398 A | 4/1997 | Smith et al. |
| 5,626,608 A | 5/1997 | Cuny et al. |
| 5,632,432 A | 5/1997 | Schulze et al. |
| 5,643,294 A | 7/1997 | Tovey et al. |
| 5,647,743 A | 7/1997 | Schmitt |
| 5,702,408 A | 12/1997 | Wales et al. |
| 5,704,534 A | 1/1998 | Huitema et al. |
| 5,713,505 A | 2/1998 | Huitema |
| 5,716,352 A | 2/1998 | Viola et al. |
| 5,759,151 A | 6/1998 | Sturges |
| 5,792,164 A | 8/1998 | Lakatos et al. |
| 5,807,376 A | 9/1998 | Viola et al. |
| 5,813,813 A | 9/1998 | Daum et al. |
| 5,823,066 A | 10/1998 | Huitema et al. |
| 5,827,323 A | 10/1998 | Klieman et al. |
| 5,836,960 A | 11/1998 | Kolesa et al. |
| 5,845,540 A | 12/1998 | Rosheim |
| 5,846,183 A | 12/1998 | Chilcoat |
| 5,873,817 A | 2/1999 | Kokish et al. |
| 5,899,425 A | 5/1999 | Corey Jr. et al. |
| 5,899,428 A | 5/1999 | Gauger |
| 5,912,658 A | 6/1999 | Bergamasco et al. |
| 5,916,146 A | 6/1999 | Allotta et al. |
| 5,916,147 A | 6/1999 | Boury |
| 5,921,956 A | 7/1999 | Grinberg et al. |
| 5,938,678 A | 8/1999 | Zirps et al. |
| 5,947,984 A | 9/1999 | Whipple |
| 5,961,532 A | 10/1999 | Finley et al. |
| 6,019,722 A | 2/2000 | Spence et al. |
| 6,042,555 A | 3/2000 | Kramer et al. |
| 6,050,996 A | 4/2000 | Schmaltz et al. |
| 6,161,543 A | 12/2000 | Cox et al. |
| 6,250,532 B1 | 6/2001 | Green et al. |
| 6,270,453 B1 | 8/2001 | Sakai |
| 6,413,229 B1 | 7/2002 | Kramer et al. |
| 6,446,850 B2 | 9/2002 | Ming-Shun |
| 6,464,704 B2 | 10/2002 | Schmaltz et al. |
| 6,471,641 B2 | 10/2002 | Sakamoto |
| 6,471,696 B1 | 10/2002 | Berube et al. |
| 6,482,149 B1 | 11/2002 | Torii |
| 6,491,626 B1 | 12/2002 | Stone et al. |
| 6,571,042 B1 | 5/2003 | Kordahi |
| 6,626,824 B2 | 9/2003 | Ruegg et al. |
| 6,635,071 B2 | 10/2003 | Boche et al. |
| 6,638,213 B2 | 10/2003 | Ogura et al. |
| 6,638,287 B2 | 10/2003 | Danitz et al. |
| RE38,335 E | 11/2003 | Aust et al. |
| 6,641,528 B2 | 11/2003 | Torii |
| 6,644,532 B2 | 11/2003 | Green et al. |
| 6,666,854 B1 | 12/2003 | Lange |
| 6,669,254 B2 | 12/2003 | Thom et al. |
| 6,676,676 B2 | 1/2004 | Danitz et al. |
| 6,682,541 B1 | 1/2004 | Gifford, III et al. |
| 6,730,020 B2 | 5/2004 | Peng et al. |
| 6,743,239 B1 | 6/2004 | Kuehn et al. |
| 6,746,443 B1 | 6/2004 | Morley et al. |
| 6,749,560 B1 | 6/2004 | Konstorum et al. |
| 6,752,823 B2 | 6/2004 | Prestel |
| 6,764,445 B2 | 7/2004 | Ramans et al. |
| 6,773,327 B1 | 8/2004 | Felice et al. |
| 6,817,972 B2 | 11/2004 | Snow |
| 6,824,548 B2 | 11/2004 | Smith et al. |

(56) References Cited

U.S. PATENT DOCUMENTS

| | | |
|---|---|---|
| 6,843,794 B2 | 1/2005 | Sixto, Jr. |
| 6,858,005 B2 | 2/2005 | Ohline et al. |
| 6,902,560 B1 | 6/2005 | Morley et al. |
| 6,942,613 B2 | 9/2005 | Ewers et al. |
| 6,945,979 B2 | 9/2005 | Kortenbach et al. |
| 6,960,162 B2 | 11/2005 | Saadat et al. |
| 6,960,163 B2 | 11/2005 | Ewers et al. |
| 6,976,969 B2 | 12/2005 | Messerly |
| 6,994,700 B2 | 2/2006 | Elkins et al. |
| 7,090,637 B2 | 8/2006 | Danitz et al. |
| 7,138,976 B1 | 11/2006 | Bouzit et al. |
| 7,147,650 B2 | 12/2006 | Lee |
| 7,320,700 B2 | 1/2008 | Cooper et al. |
| 7,410,483 B2 | 8/2008 | Danitz et al. |
| 7,480,600 B2 | 1/2009 | Massie et al. |
| 7,553,275 B2 | 6/2009 | Padget et al. |
| 7,608,083 B2 | 10/2009 | Lee et al. |
| 7,615,066 B2 | 11/2009 | Danitz et al. |
| 7,637,905 B2 | 12/2009 | Saadat et al. |
| 7,678,117 B2 | 3/2010 | Hinman et al. |
| 7,682,307 B2 | 3/2010 | Danitz et al. |
| 7,708,758 B2 | 5/2010 | Lee et al. |
| 7,785,252 B2 | 8/2010 | Danitz et al. |
| 7,828,808 B2 | 11/2010 | Hinman et al. |
| 7,842,028 B2 | 11/2010 | Lee |
| 7,854,109 B2 | 12/2010 | Zubiate et al. |
| 8,100,824 B2 | 1/2012 | Hegeman et al. |
| 8,182,417 B2 | 5/2012 | Danitz |
| 8,535,347 B2 | 9/2013 | Danitz et al. |
| 2001/0023313 A1 | 9/2001 | Ide |
| 2001/0042766 A1 | 11/2001 | Ming-Shun |
| 2002/0096177 A1 | 7/2002 | Toti et al. |
| 2002/0111604 A1 | 8/2002 | Doyle et al. |
| 2002/0156497 A1 | 10/2002 | Nagase et al. |
| 2002/0161281 A1 | 10/2002 | Jaffe et al. |
| 2002/0177750 A1 | 11/2002 | Pilvisto |
| 2003/0036748 A1 | 2/2003 | Cooper et al. |
| 2003/0050649 A1 | 3/2003 | Brock et al. |
| 2003/0073939 A1 | 4/2003 | Taylor et al. |
| 2003/0078644 A1 | 4/2003 | Phan |
| 2003/0108888 A1 | 6/2003 | Scanlan et al. |
| 2003/0109898 A1 | 6/2003 | Schwarz et al. |
| 2003/0114838 A1 | 6/2003 | O'Neill et al. |
| 2003/0135204 A1 | 7/2003 | Lee et al. |
| 2003/0149338 A1 | 8/2003 | Francois et al. |
| 2003/0153902 A1 | 8/2003 | Doyle et al. |
| 2003/0229271 A1 | 12/2003 | Briscoe et al. |
| 2003/0233026 A1 | 12/2003 | Saadat et al. |
| 2004/0054322 A1 | 3/2004 | Vargas |
| 2004/0138529 A1 | 7/2004 | Wiltshire et al. |
| 2004/0138700 A1 | 7/2004 | Cooper et al. |
| 2004/0140786 A1 | 7/2004 | Borenstein |
| 2004/0199052 A1 | 10/2004 | Banik et al. |
| 2005/0090809 A1 | 4/2005 | Cooper et al. |
| 2005/0096694 A1 | 5/2005 | Lee |
| 2005/0119527 A1 | 6/2005 | Banik et al. |
| 2005/0273084 A1 | 12/2005 | Hinman et al. |
| 2006/0009759 A1 | 1/2006 | Chrisitian et al. |
| 2006/0020287 A1 | 1/2006 | Lee et al. |
| 2006/0036255 A1 | 2/2006 | Pond et al. |
| 2006/0041188 A1 | 2/2006 | Dirusso et al. |
| 2006/0058582 A1 | 3/2006 | Maahs et al. |
| 2006/0111209 A1 | 5/2006 | Hinman et al. |
| 2006/0111210 A1 | 5/2006 | Hinman |
| 2006/0111615 A1 | 5/2006 | Danitz et al. |
| 2006/0111616 A1 | 5/2006 | Danitz |
| 2006/0199999 A1 | 9/2006 | Ikeda et al. |
| 2006/0201130 A1 | 9/2006 | Danitz |
| 2007/0250113 A1 | 10/2007 | Hegeman et al. |
| 2007/0276430 A1 | 11/2007 | Lee et al. |
| 2007/0287993 A1 | 12/2007 | Hinman et al. |
| 2008/0065116 A1 | 3/2008 | Lee et al. |
| 2008/0188869 A1 | 8/2008 | Weitzner et al. |
| 2008/0188871 A1 | 8/2008 | Smith et al. |
| 2008/0255421 A1 | 10/2008 | Hegeman et al. |
| 2008/0255588 A1 | 10/2008 | Hinman |
| 2008/0255608 A1 | 10/2008 | Hinman et al. |
| 2008/0262538 A1 | 10/2008 | Danitz et al. |
| 2010/0041945 A1 | 2/2010 | Isbell, Jr. |
| 2010/0234831 A1 | 9/2010 | Hinman et al. |
| 2010/0249759 A1 | 9/2010 | Hinman et al. |
| 2010/0261964 A1 | 10/2010 | Danitz et al. |
| 2010/0261971 A1 | 10/2010 | Danitz et al. |
| 2010/0262075 A1 | 10/2010 | Danitz et al. |
| 2010/0262161 A1 | 10/2010 | Danitz et al. |
| 2010/0305717 A1 | 12/2010 | Tong et al. |
| 2011/0022078 A1 | 1/2011 | Hinman |
| 2011/0087071 A1 | 4/2011 | Danitz et al. |
| 2012/0095451 A1 | 4/2012 | Hegeman et al. |

FOREIGN PATENT DOCUMENTS

| | | |
|---|---|---|
| EP | 0836833 A2 | 4/1998 |
| EP | 1132041 A2 | 9/2001 |
| EP | 0836833 A3 | 9/2002 |
| EP | 1395398 B1 | 1/2006 |
| JP | 6262549 A2 | 9/1994 |
| JP | 2001299768 A2 | 10/2001 |
| WO | 9320878 A1 | 10/1993 |
| WO | WO-9849961 A1 | 11/1998 |
| WO | 0110292 A1 | 2/2001 |
| WO | 0197694 A1 | 12/2001 |
| WO | 0213682 A1 | 2/2002 |
| WO | 02087420 A2 | 11/2002 |
| WO | 03001986 | 1/2003 |
| WO | WO-200419769 A1 | 3/2004 |
| WO | 2004105578 A2 | 12/2004 |
| WO | WO-2004105578 A9 | 4/2005 |
| WO | 2005067785 | 7/2005 |
| WO | 2005120326 A2 | 12/2005 |
| WO | 2005120327 A2 | 12/2005 |
| WO | WO-2005120327 A3 | 3/2006 |
| WO | 200657699 | 6/2006 |
| WO | 200657702 | 6/2006 |
| WO | WO-2006057700 A1 | 6/2006 |
| WO | 200673581 | 7/2006 |

OTHER PUBLICATIONS

Danitz, David J.; U.S. Appl. No. 12/766,822 entitled "Articulating catheters," filed Apr. 23, 2010.

Danitz, David J.; U.S. Appl. No. 12/766,825 entitled "Articulating endoscopes," filed Apr. 23, 2010.

Danitz, David J.; U.S. Appl. No. 12/766,827 entitled "Articulating retractors," filed Apr. 23, 2010.

Danitz et al.; U.S. Appl. No. 12/766,818 entitled "Articulating instruments with joystick control," filed Apr. 23, 2010.

Hinman, Cameron; U.S. Appl. No. 12/508,478 entitled "Articulating mechanism," filed Jul. 23, 2009.

Hinman et al.; U.S. Appl. No. 12/725,377 entitled "Articulating mechanism with flex-hinged links," filed Mar. 16, 2010.

Hinman et al.; U.S. Appl. No. 12/816,359 entitled "Link systems and articulation mechanisms for remote manipulation of surgical or diagnostic tools," filed Jun. 15, 2010.

Prasad et al., "Epicardial ablation on the beating heart: progress towards an off-pump maze procedure," The Heart Surgery Forum, 2001, vol. 5, Issue 2, pp. 100-104.

Simha et al., "The elctrocautery maze—how I do it," The Heart Surgery Forum, 2001, vol. 4, Issue 4, pp. 340-345.

Supplementary European Search Report for Application No. EP04752882.3, mailed on Feb. 6, 2013, 3 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Hegeman et al; U.S. Appl. No. 11/787,201 entitled "Articulating tool with improved tension member system" filed Apr. 16, 2007.

http://engr.bd.psu.edu/pkoch/plasticdesign/snap_design.htm date verified via internet archive (Sep. 2, 2003).

(56) References Cited

OTHER PUBLICATIONS

International Search Report and Written Opinion for Application No. PCT/US2005/033377, mailed on May 11, 2006, 15 pages.
International Search Report and Written Opinion for Application No. PCT/US2008/060385, mailed on Jul. 15, 2008, 8 pages.
International Search Report for Application No. PCT/US2005/018145 (WO2005120326), mailed on Feb. 20, 2006, 5 pages.
International Search Report mailed Aug. 26, 2005 for PCT Application No. PCT/US04/15944 filed May 21, 2004, 1 page.
International search report mailed on Jan. 25, 2006 for PCT Application No. PCT/US2005/033257 filed on Sep. 15, 2005, 2 pages.
Invitation to Pay Additional Fees mailed on Feb. 13, 2006 for PCT Application No. PCT/US2005/033377 filed on Sep. 19, 2005, 6 pages.
Merriam-Webster, "Define-reciprocal", Merriam-Webster's Collegiate Dictionary, 2009, p. 1038, Edition 11, Merriam-Webster, In corp, Published in: US.
U.S. Appl. No. 10/648,911, filed Sep. 24, 2004 for Danitz et al., 57 pages.
Written Opinion for Application No. PCT/US04/15944, mailed on Aug. 26, 2005, 3 pages.
Written Opinion for Application No. PCT/US2005/033257, mailed on Jan. 25, 2006, 7 pages.
Extended European Search Report for Application No. EP14168730.1 mailed on Dec. 15, 2014, 6 pages.

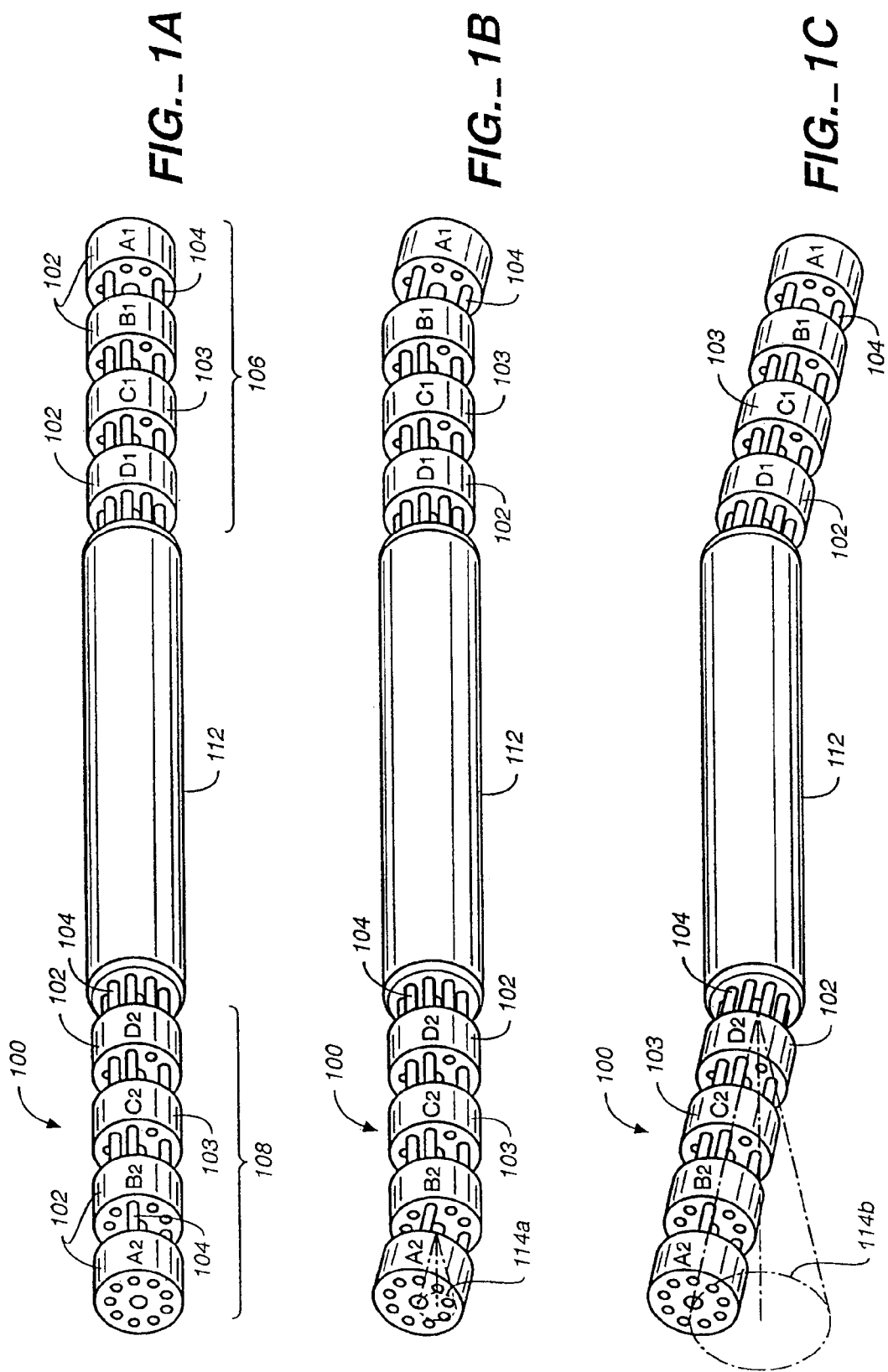

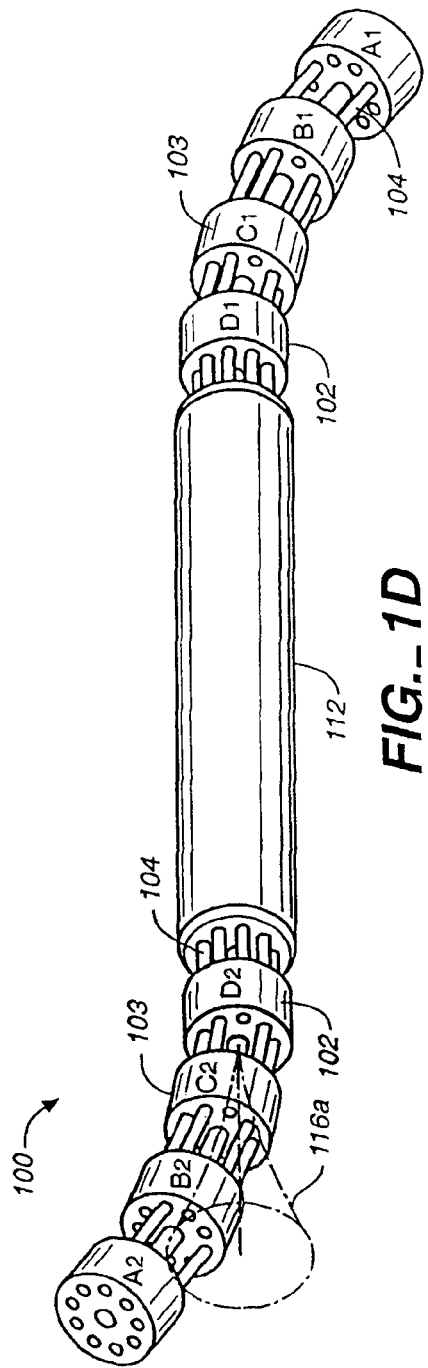
FIG._1D
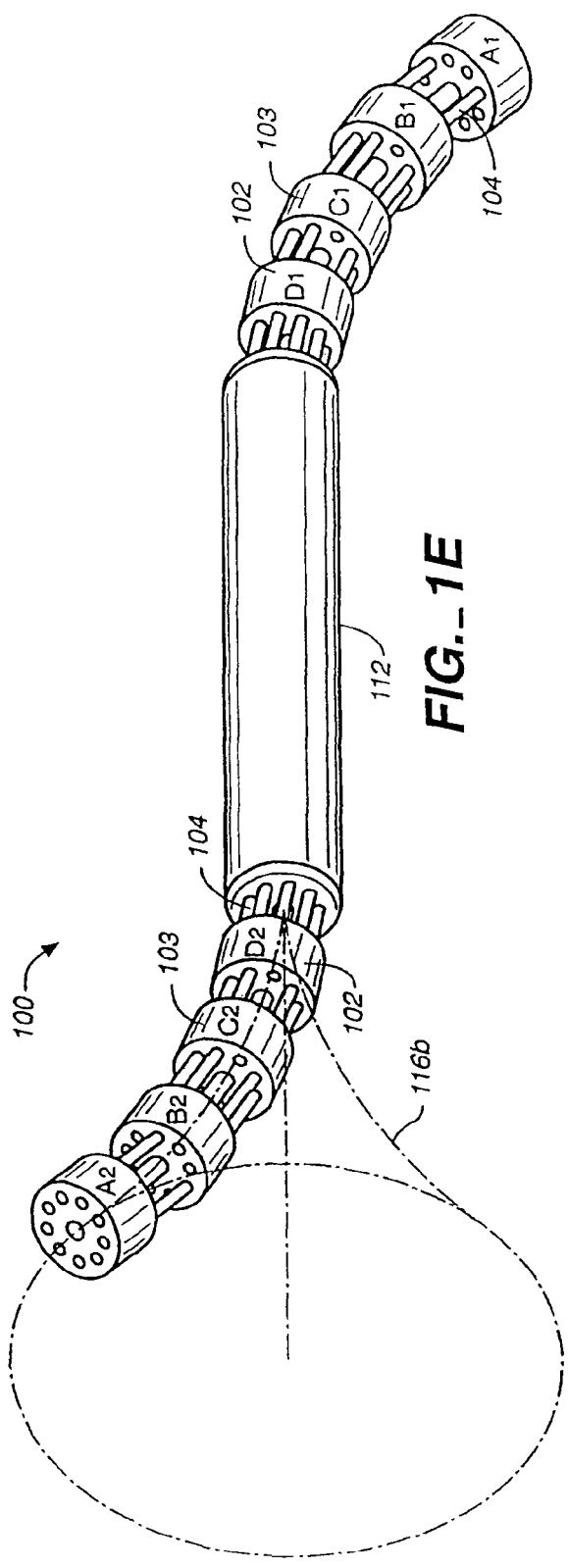
FIG._1E

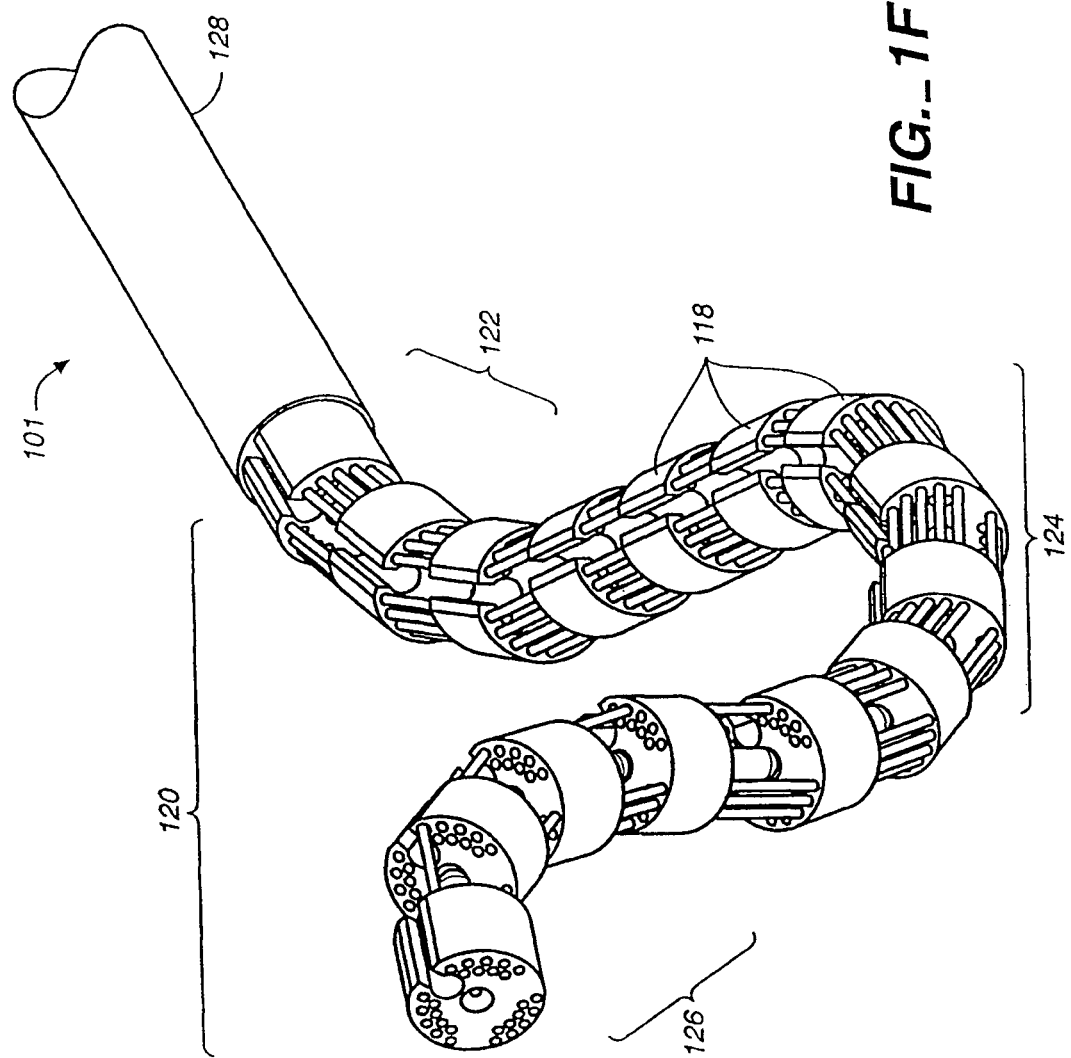
FIG._1F

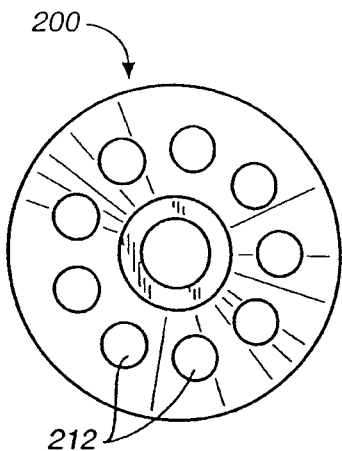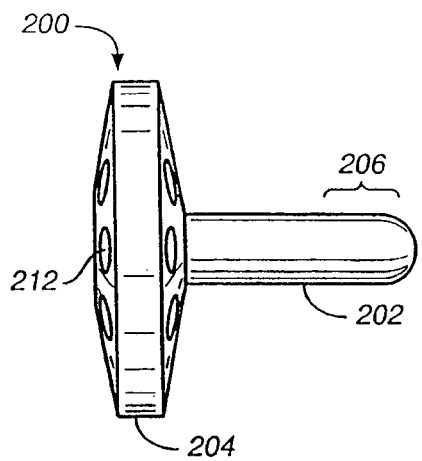
FIG._2A  FIG._2B
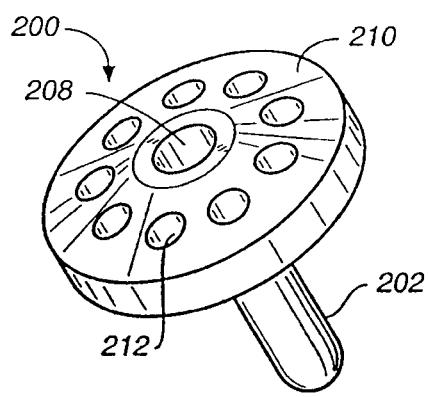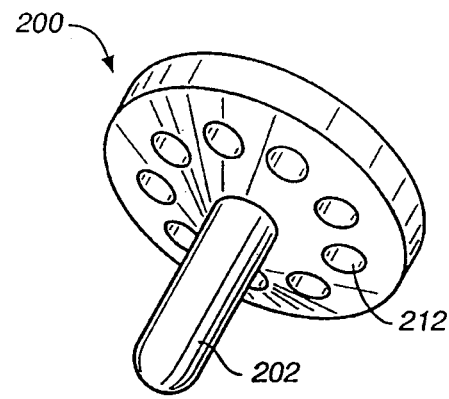
FIG._2C  FIG._2D
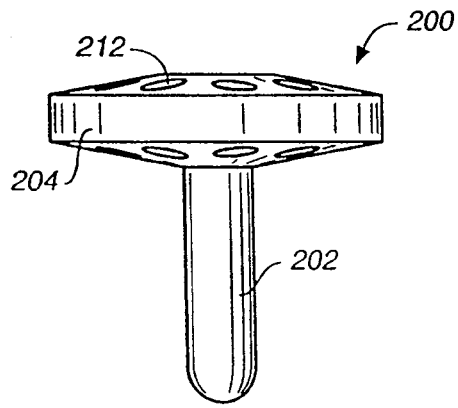
FIG._2E

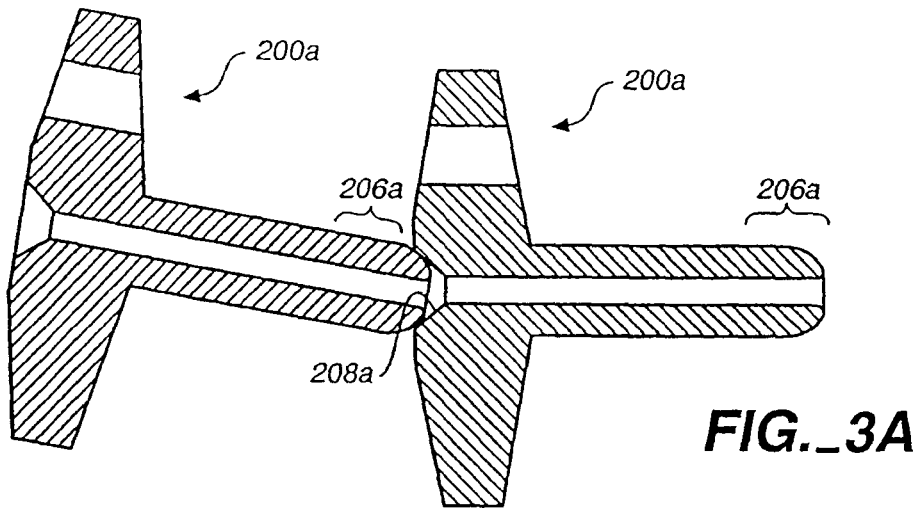
*FIG._3A*
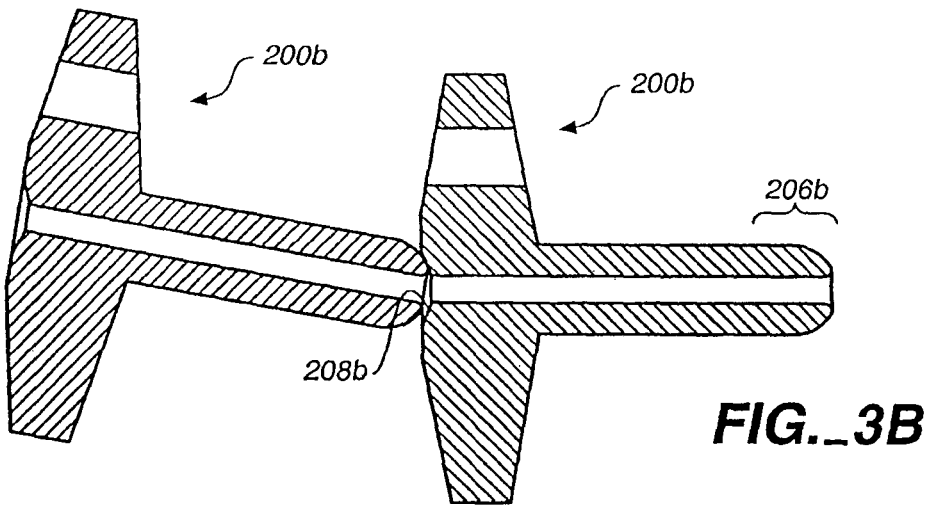
*FIG._3B*
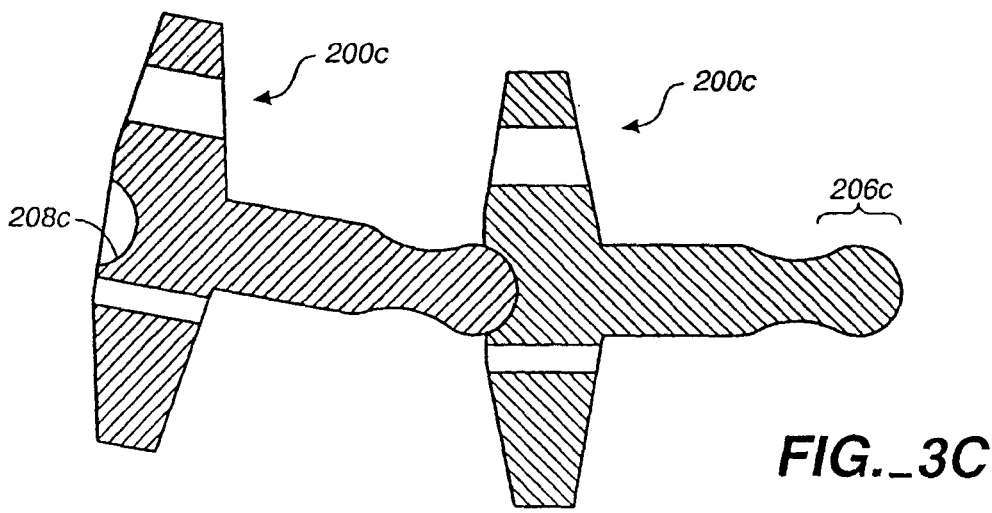
*FIG._3C*

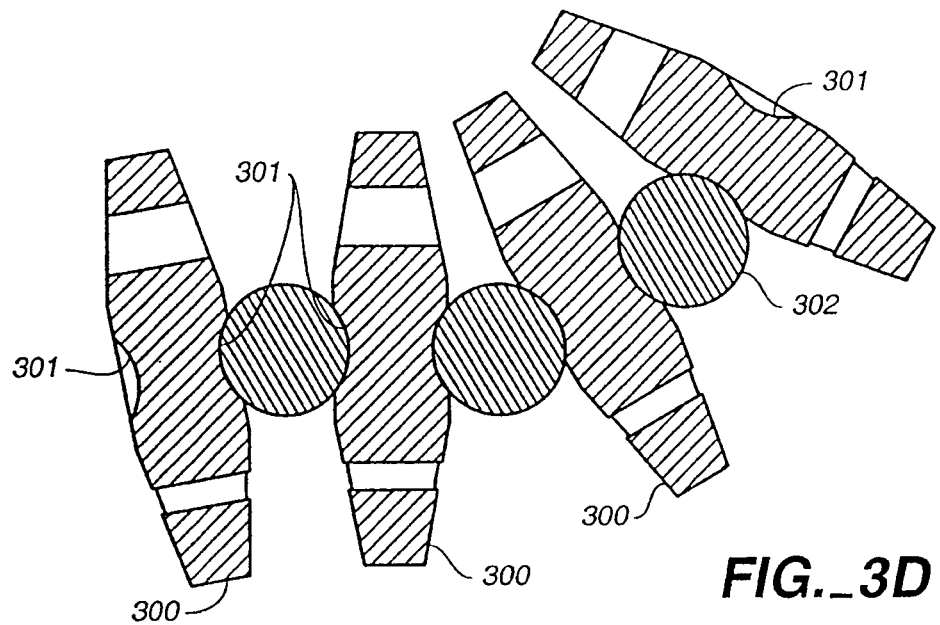
FIG._3D
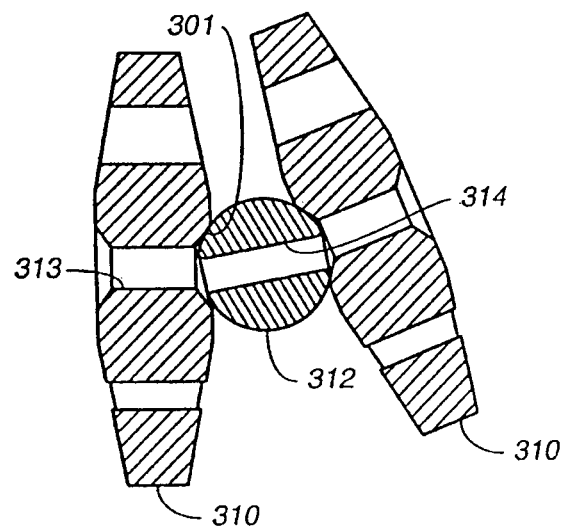
FIG._3E

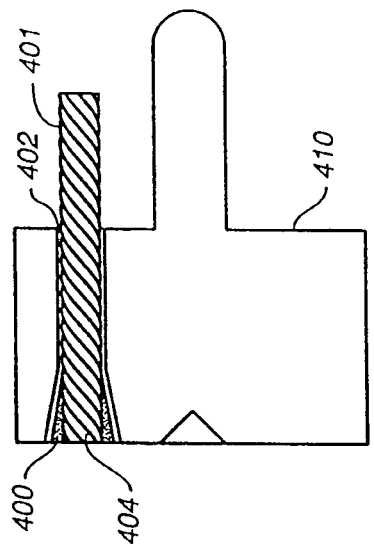
FIG._4C
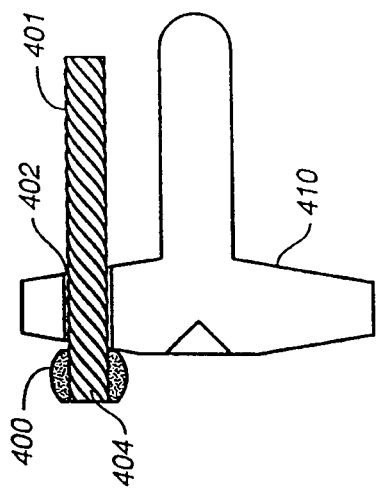
FIG._4B
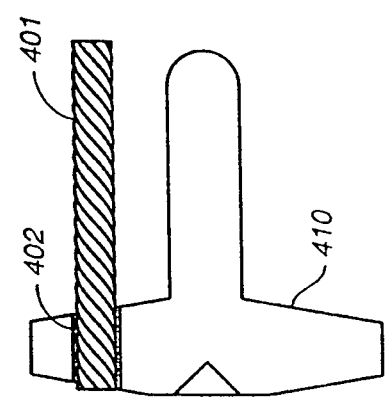
FIG._4A

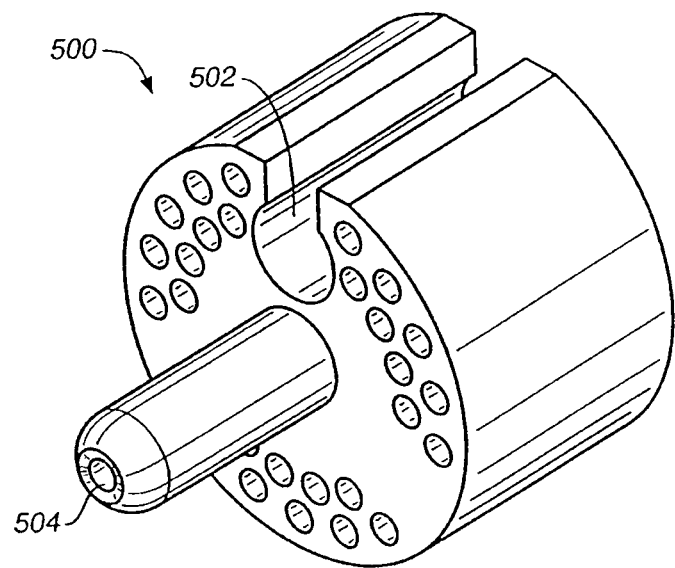
FIG._5A
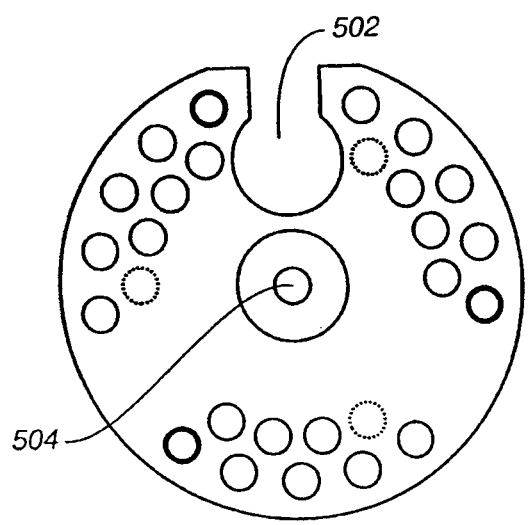
FIG._5B

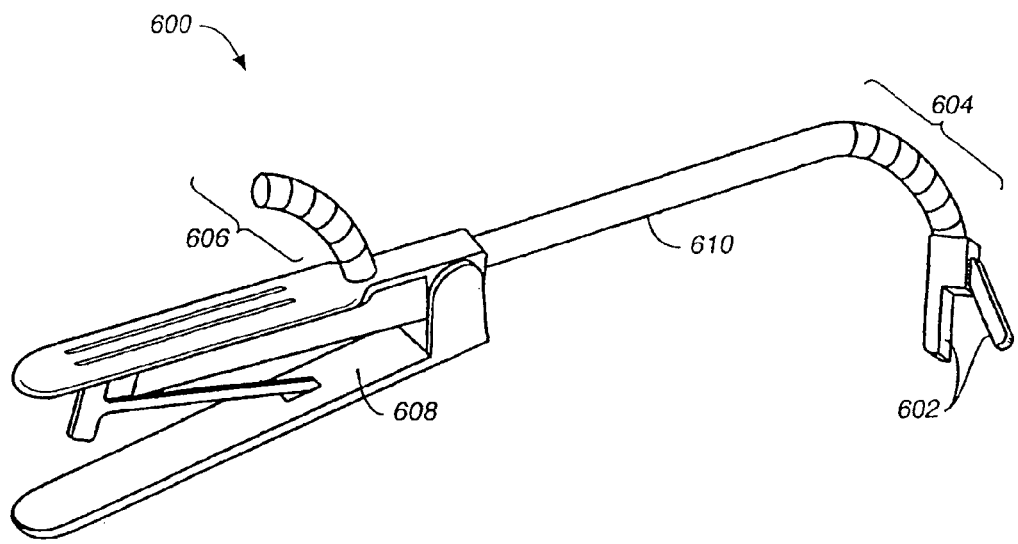
FIG._6A
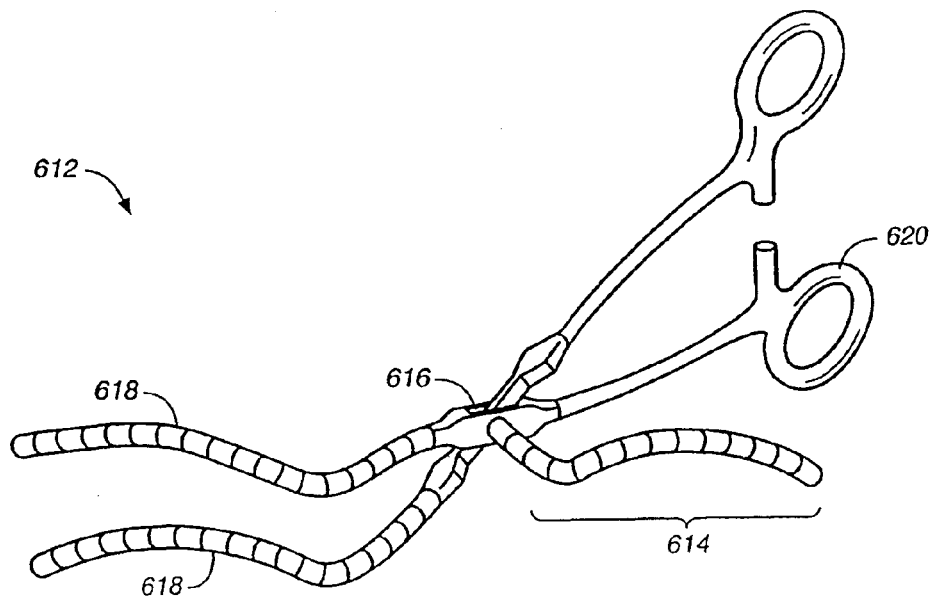
FIG._6B

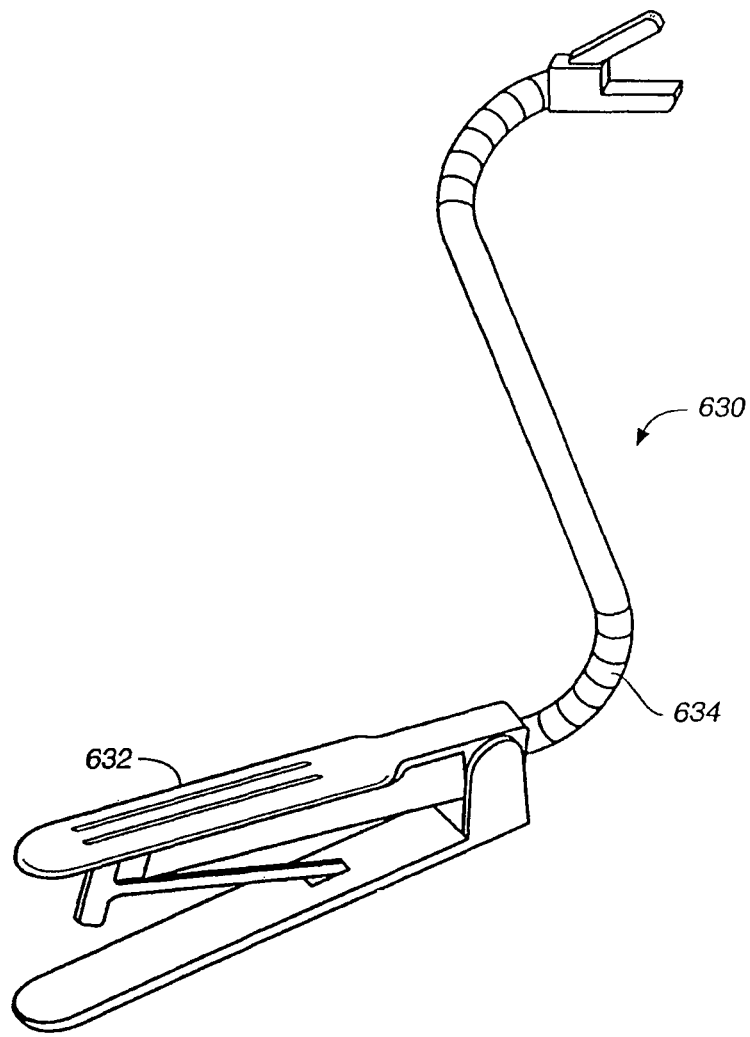
FIG._6C

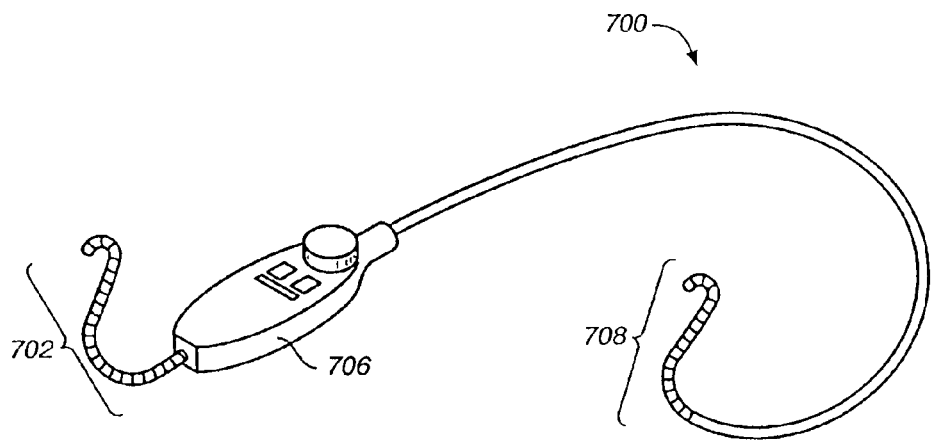
FIG._7
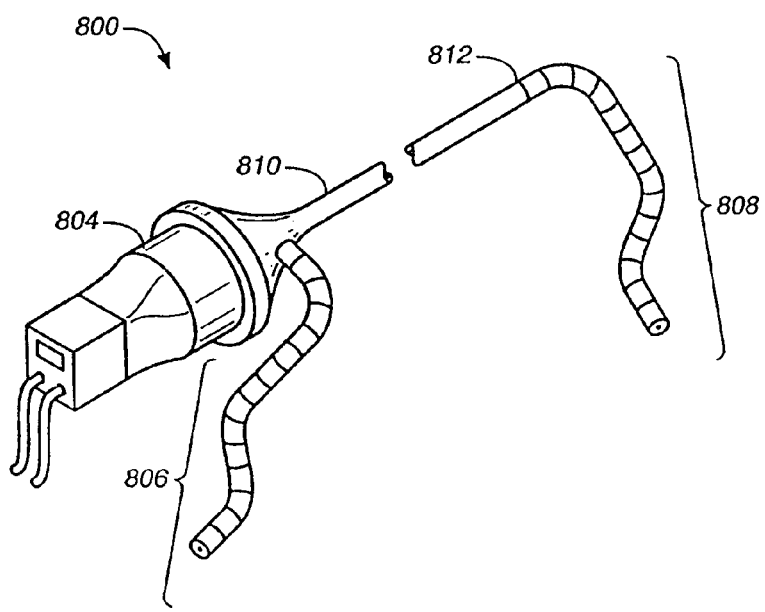
FIG._8

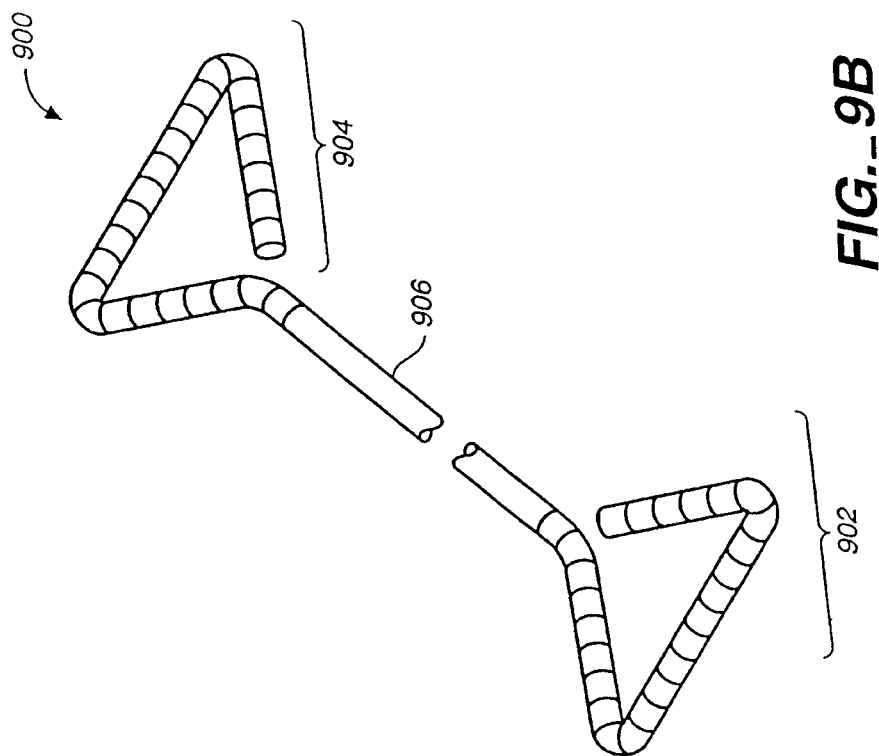
FIG._9B
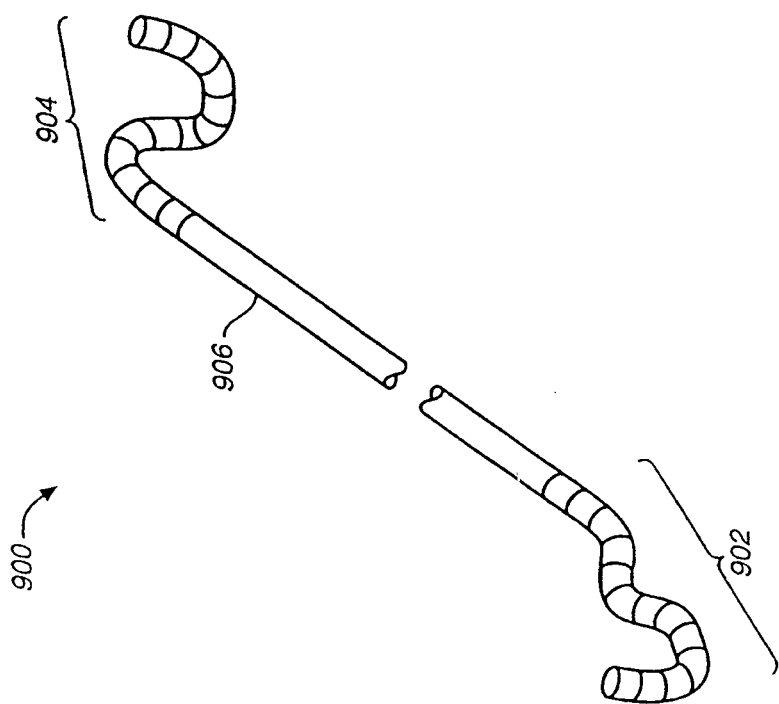
FIG._9A

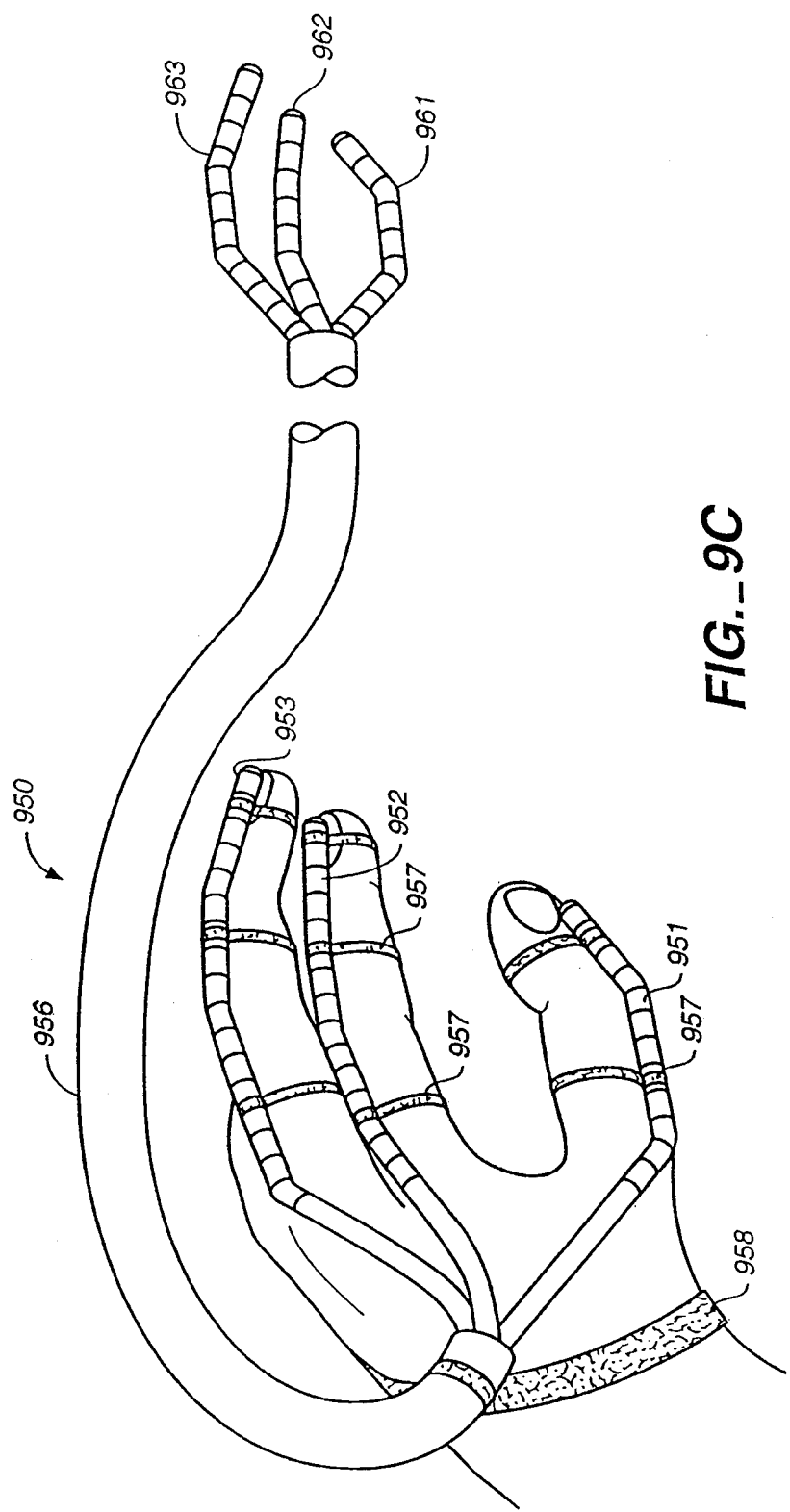
FIG._9C

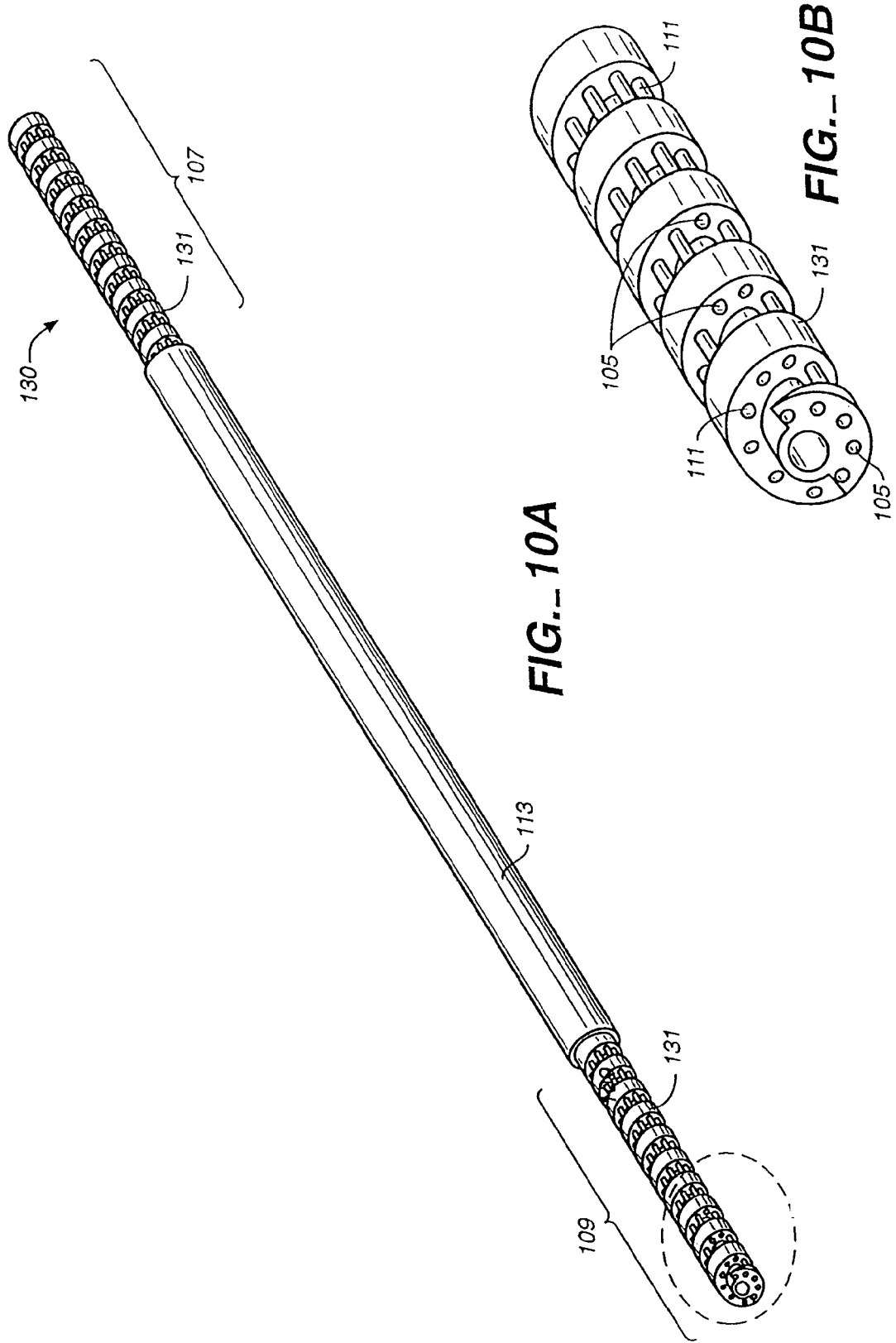

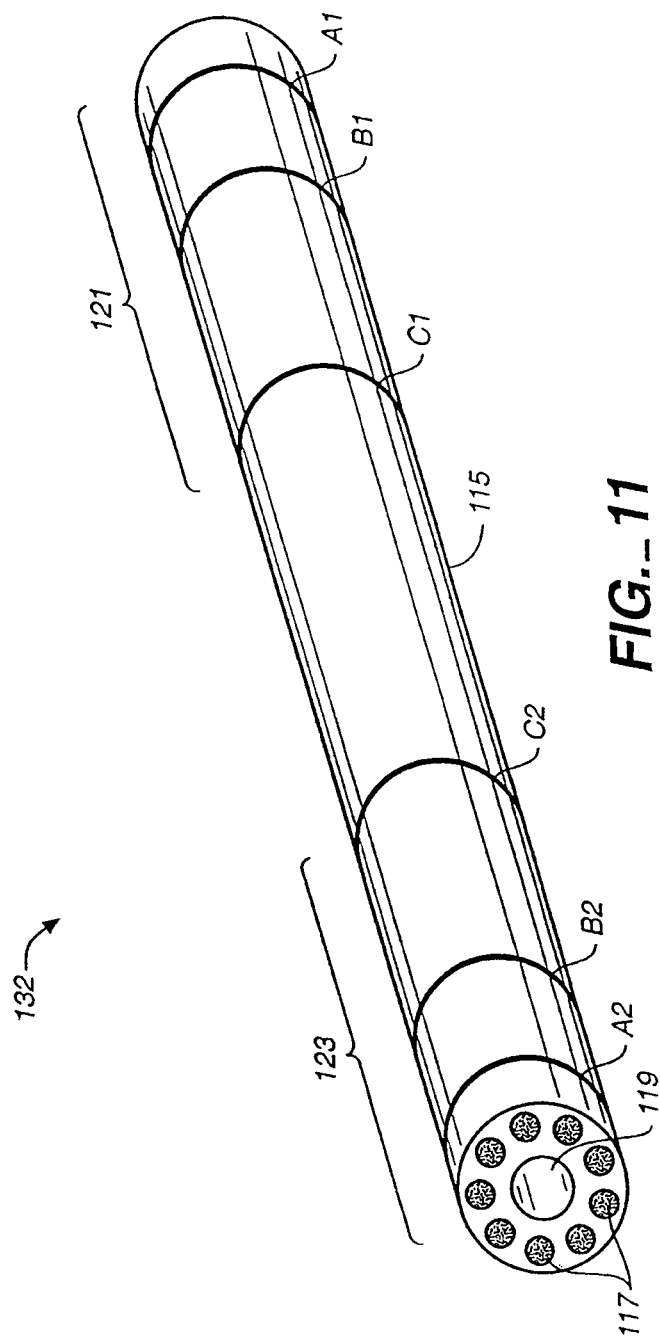
FIG._11

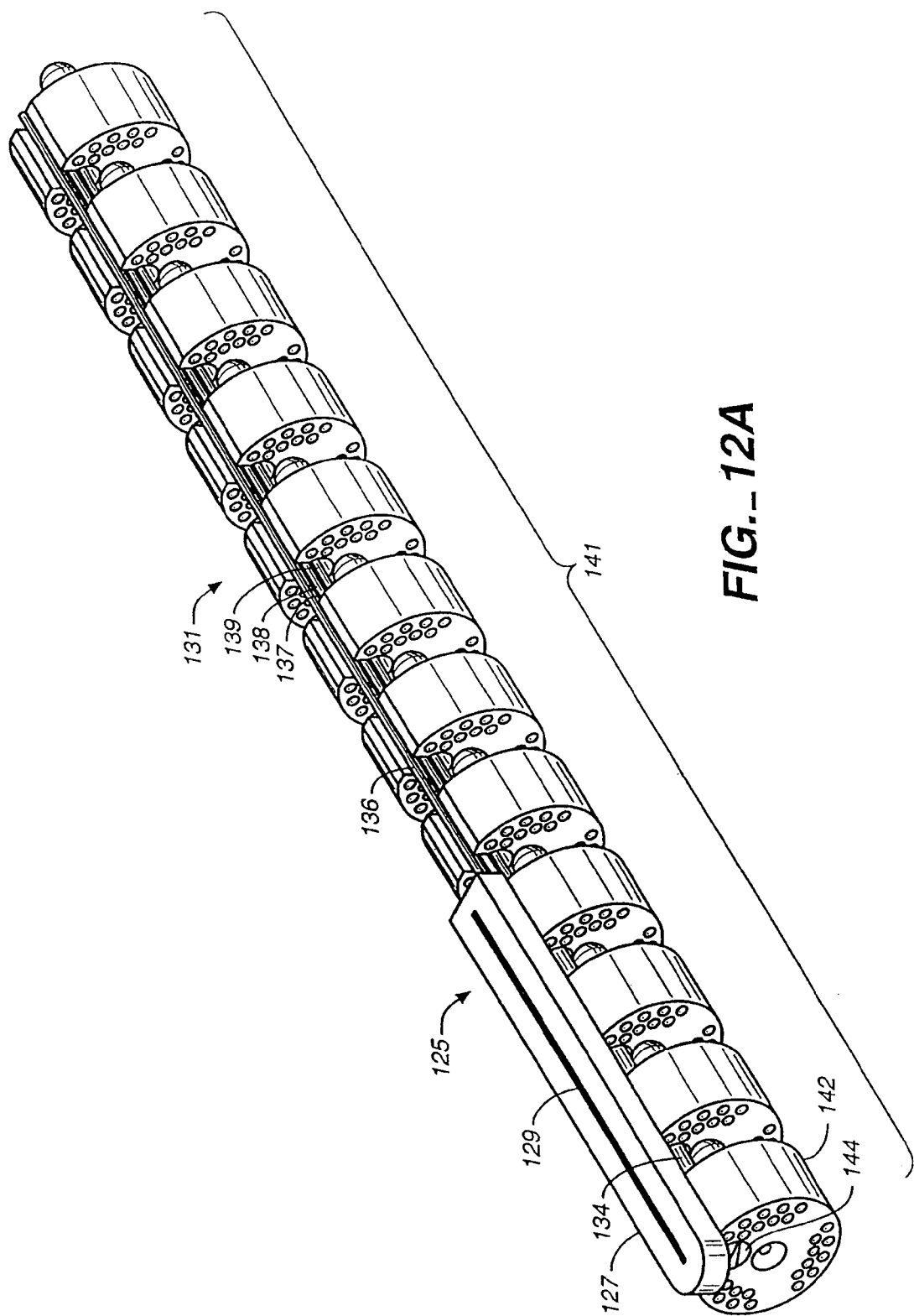
FIG._12A

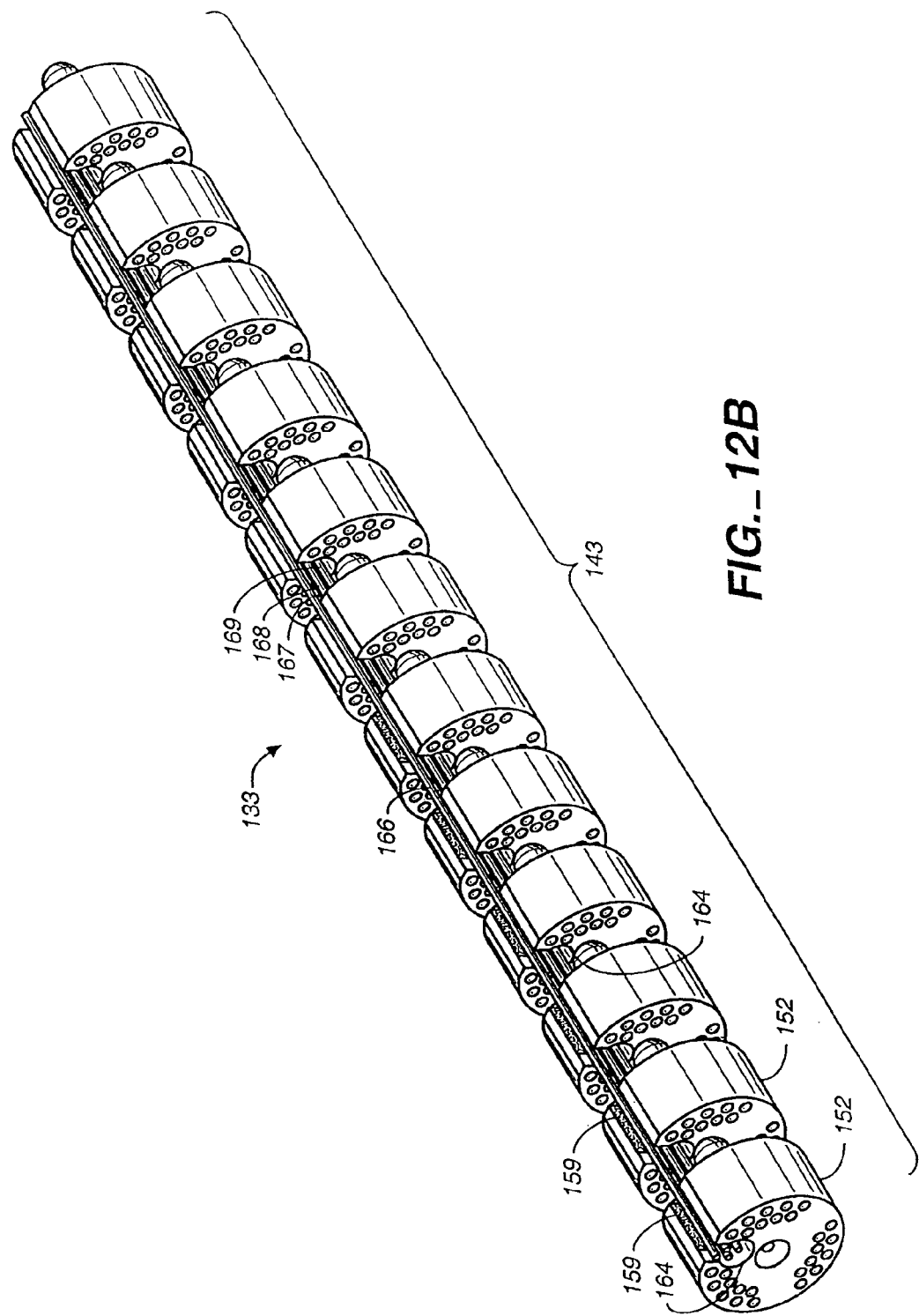

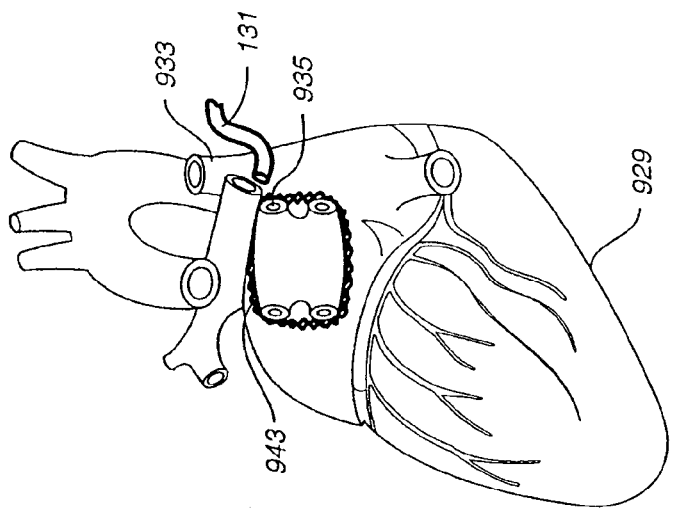
FIG._13C
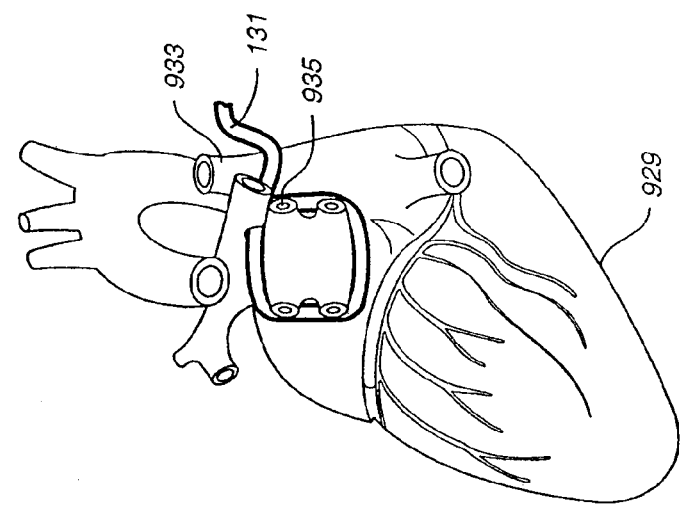
FIG._13B
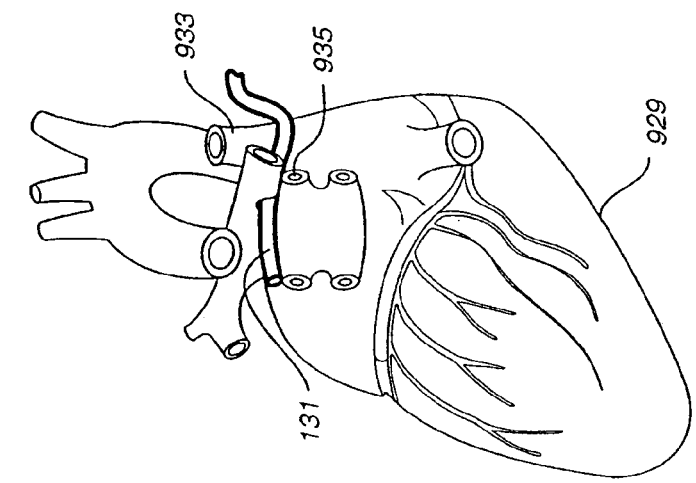
FIG._13A

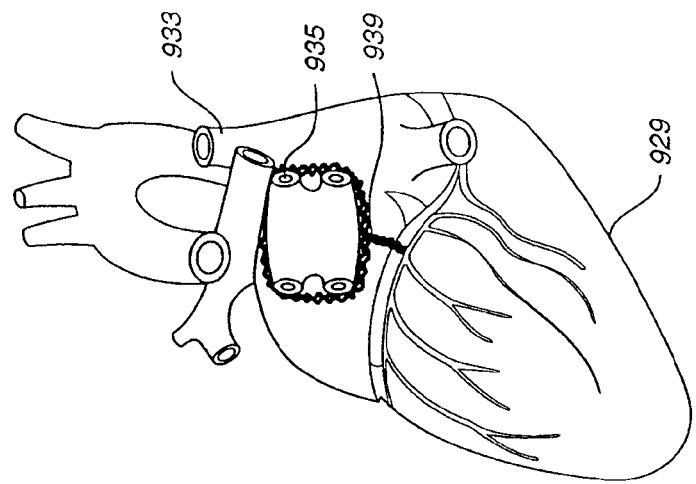
FIG._13F
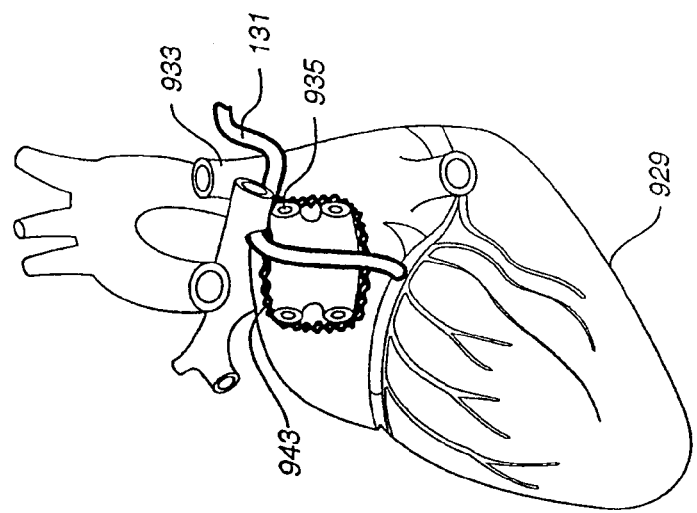
FIG._13E
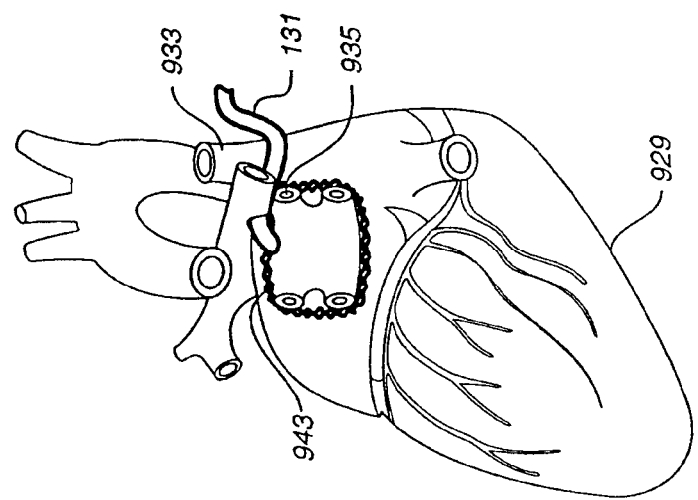
FIG._13D

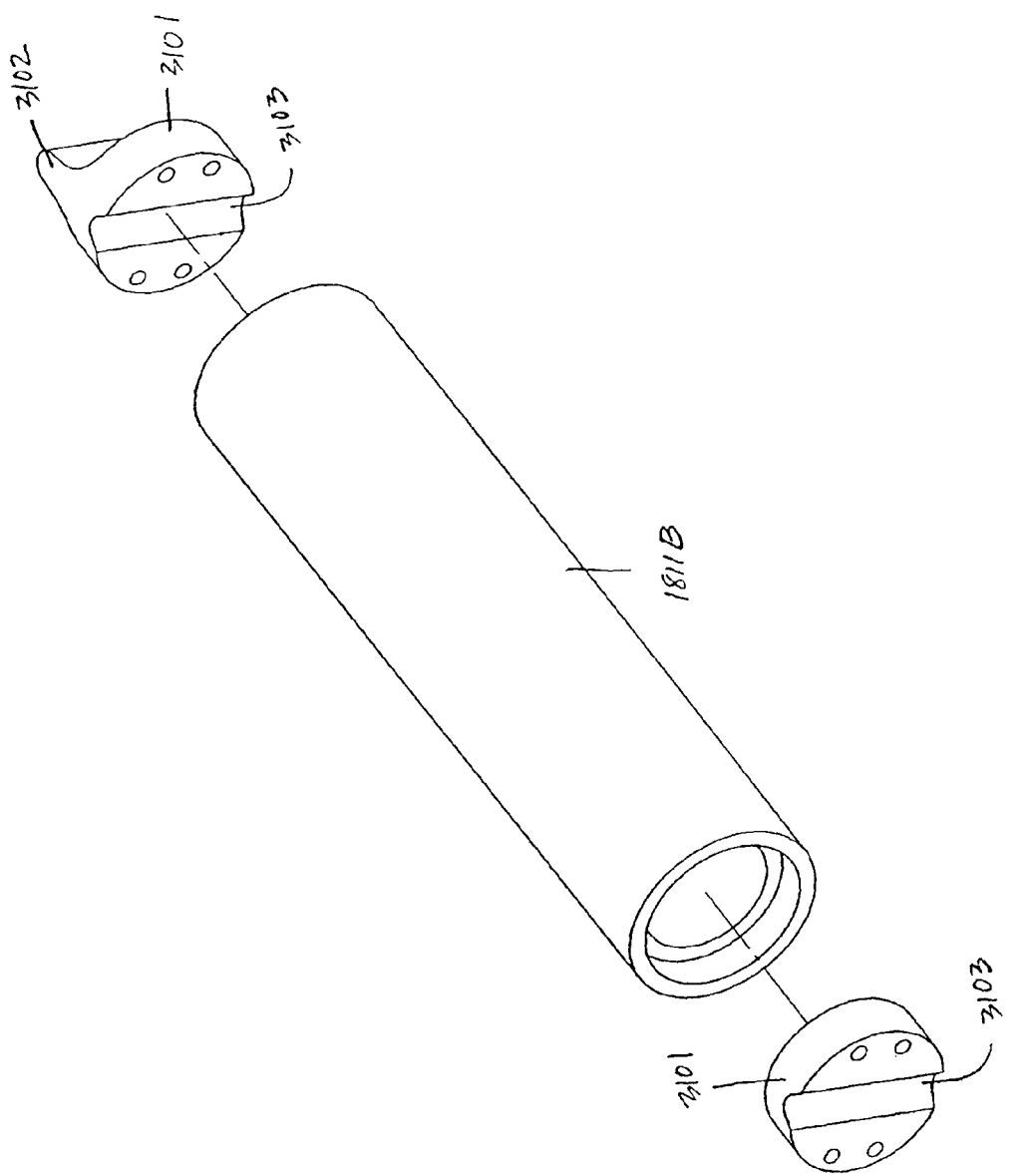

ARTICULATING MECHANISMS WITH ACTUATABLE ELEMENTS

CROSS REFERENCE TO RELATED APPLICATIONS

This application is a continuation of U.S. application Ser. No. 12/766,820, filed Apr. 23, 2010, now U.S. Pat. No. 8,535, 347, which is a divisional of U.S. application Ser. No. 12/109, 333, filed Apr. 24, 2008, which is a continuation of U.S. application Ser. No. 10/997,249, filed Nov. 24, 2004, now U.S. Pat. No. 7,410,483, which is a continuation-in-part a U.S. application Ser. No. 10/444,769 filed May 23, 2003 now U.S. Pat. No. 7,090,637, the disclosures of which are incorporated herein by reference in their entireties.

FIELD OF THE INVENTION

This invention relates to articulating mechanisms and applications thereof, including the remote guidance and manipulation of surgical or diagnostic instruments and tools. In particular, this invention relates to hand-actuated mechanisms for the remote manipulation of body tissue.

BACKGROUND OF THE INVENTION

The ability to easily remotely manipulate instruments and tools is of interest in a wide variety of industries and applications, in particular where it is desired to control movements of instruments or tools in spaces difficult to access by hand, or areas that might otherwise present a risk or danger. These can include situations where the targeted site for the application of a tool or instrument is difficult to access during surgical procedures, or the manufacture or repair of machinery, or even during commercial and household uses, where manual access to a targeted site is restricted or otherwise. Other situations can include, e.g., industrial applications where the work environment is dangerous to the user, for example, workspaces exposed to dangerous chemicals. Still other situations can include, e.g., law enforcement or military applications where the user may be at risk, such as deployment of a tool or instrument into a dangerous or hostile location.

Using surgical procedures as an illustrative example, procedures such as endoscopy and laparoscopy typically employ instruments that are steered within or towards a target organ or tissue from a position outside the body. Examples of endoscopic procedures include sigmoidoscopy, colonoscopy, esophagogastroduodenoscopy, and bronchoscopy. Traditionally, the insertion tube of an endoscope is advanced by pushing it forward, and retracted by pulling it back. The tip of the tube may be directed by twisting and general up/down and left/right movements. Oftentimes, this limited range of motion makes it difficult to negotiate acute angles (e.g., in the rectosigmoid colon), creating patient discomfort and increasing the risk of trauma to surrounding tissues.

Laparoscopy involves the placement of trocar ports according to anatomical landmarks. The number of ports usually varies with the intended procedure and number of instruments required to obtain satisfactory tissue mobilization and exposure of the operative field. Although there are many benefits of laparoscopic surgery, e.g., less postoperative pain, early mobilization, and decreased adhesion formation, it is often difficult to achieve optimal retraction of organs and maneuverability of conventional instruments through laparoscopic ports. In some cases, these deficiencies may lead to increased operative time or imprecise placement of components such as staples and sutures.

Steerable catheters are also well known for both diagnostic and therapeutic applications. Similar to endoscopes, such catheters include tips that can be directed in generally limited ranges of motion to navigate a patient's vasculature.

There have been many attempts to design endoscopes and catheters with improved steerability. For example, U.S. Pat. No. 3,557,780 to Sato; U.S. Pat. No. 5,271,381 to Ailinger et al.; U.S. Pat. No. 5,916,146 to Alotta et al.; and U.S. Pat. No. 6,270,453 to Sakai describe endoscopic instruments with one or more flexible portions that may be bent by actuation of a single set of wires. The wires are actuated from the proximal end of the instrument by rotating pinions (Sato), manipulating knobs (Ailinger et al.), a steerable arm (Alotta et al.), or by a pulley mechanism (Sato).

U.S. Pat. No. 5,916,147 to Boury et al. discloses a steerable catheter having four wires that run within the catheter wall. Each wire terminates at a different part of the catheter. The proximal end of the wires extend loosely from the catheter so that the physician may pull them. The physician is able to shape and thereby steer the catheter by selectively placing the wires under tension.

Although each of the devices described above are remotely steerable, their range of motion is generally limited, at least in part because typically only a single cable set is employed in connecting links or segments of the steerable elements. As such, independent movement at each link or segment is not possible. Rather, the distal links or segments bend together as a unit or units. The steering mechanisms may also be laborious to use, such as in the catheter of Boury et al. where each wire must be separately pulled to shape the catheter. Further, in the case of, e.g., endoscopes and steerable catheters that use knob and pulley mechanisms, it requires a significant amount of training to become proficient in maneuvering the device through a patient's anatomy.

Consequently, a device with enhanced remote maneuverability to controllably navigate complex anatomy may allow more efficient and precise advancement and deployment of surgical and diagnostic instruments and tools, as well as help decrease trauma to surrounding tissues, minimize patient discomfort, and decrease operative time and perhaps even patient morbidity during various surgical procedures. It would also be advantageous for such a device to provide a more intuitive and facile user interface to achieve such enhanced maneuverability.

A user interface that accurately translates finger movement of the human hand to a surgical instrument or tool is one way of achieving remote enhanced maneuverability. Although many attempts have been made to implement such a device, such as described in U.S. Pat. No. 5,441,494 to Ortiz; U.S. Pat. No. 5,807,376 to Viola et al.; and U.S. Pat. No. 5,813,813 to Daum et al., there still exists a need for a device with improved control and range of motion.

Thus, a device that not only provides a hand user interface, but an actuation mechanism that allows for close simulation of human hand movements to enhance remote maneuverability is highly desirable.

SUMMARY OF THE INVENTION

The present invention provides an articulating mechanism useful for a variety of purposes including but not limited to the remote manipulation of instruments such as surgical or diagnostic instruments or tools, including but not limited to endoscopes, catheters, Doppler flow meters, microphones, probes, retractors, dissectors, staplers, clamps, graspers, scissors or cutters, ablation or cauterizing elements, and the like. The articulating mechanism may be used to steer these instruments within a body region or to a target site within a body region of a patient, and can further be employed to actuate or facilitate actuation of such instruments and tools.

In one variation, the articulating mechanism includes multiple pairs of links, each link of each pair being maintained in a spaced apart relationship relative to the other link of the pair, and multiple sets of cables, with each cable set connecting the links of a discrete pair to one another and terminating at the links of each discrete pair, such that movement of one link of a pair causes corresponding relative movement of the other link of the pair. The relative movement at the distal end of the articulating mechanism corresponds to that at the proximal end.

In another variation, the articulating mechanism includes a continuous flexible member. The continuous flexible member includes multiple pairs of segments, with each segment of each pair being maintained in a spaced apart relationship relative to the other segment of the pair, and multiple sets of cables, with each set connecting the segments of a discrete pair to one another and terminating at the segments of each discrete pair, such that movement of one segment of a pair causes corresponding relative movement of the other segment of the pair. In some instances, the continuous flexible member may be, e.g., a catheter with a plurality of lumens, where each cable set terminates at a different axial location along the length of the catheter. In other instances the continuous flexible member may have a helical arrangement, with each segment corresponding to one turn of the helix. If desired, a flexible linkage may be placed between the helical segments or links.

Variations of the articulating mechanism can also include segments or links that may include a channel for receiving a locking rod that can secure and retain the proximal end of the articulating mechanism in a fixed position. Instead of a rod, a locking sleeve may be fitted over the proximal end of the mechanism to secure and retain the proximal end in a fixed position.

A surgical or diagnostic tool may be attached to, and extend from, the distal end of articulating mechanisms according to the invention, or the articulating mechanisms may be otherwise incorporated into such tools. Examples of surgical or diagnostic tools include, but are not limited to, endoscopes, catheters, Doppler flow meters, microphones, probes, retractors, dissectors, staplers, clamps, graspers, scissors or cutters, and ablation or cauterizing elements.

A plurality of articulating mechanisms may also be combined in such a way that a user's finger movements can be remotely mimicked to manipulate an object or body tissue. In one variation, the mechanisms form a hand-actuated apparatus that includes multiple pairs of links, with each link of each discrete pair being maintained in a spaced apart relationship relative to the other link of the pair, the links incorporated into proximal and distal ends of the apparatus with the links of corresponding pairs located on the proximal and distal ends respectively, multiple sets of cables, with each set connecting the links of a discrete pair to one another, and a user hand interface at a proximal end of the apparatus configured to removably secure one or more digits of a human hand for movement, such that movement of said digit when secured to the interface moves one or more links of a pair at said proximal end and causes corresponding relative movement of the other one or more links of the pair at a distal end of the apparatus. In some instances, at least one link of a pair is an elongate link.

In another variation, the hand-actuated apparatus includes a proximal end having a user hand interface configured to removably secure one or more digits of a human hand for movement, such that flexion of the digit when secured is translated into a bending movement at the distal end effector portion. In a further variation, the user hand interface includes a finger slide where translational movement of the finger slide is translated into a bending movement at the effector portion.

The hand-actuated devices of this invention also include one or more joints at their proximal and distal ends that have the range of motion of a distal interphalangeal (DIP) joint, proximal interphalangeal (PIP) joint, or metacarpal phalangeal (MCP) joint. In some instances, control of movement of a proximal joint, such as a MCP joint, is independent of control of one or more distal joints, e.g., a PIP joint or DIP joint. In other instances, movement at the proximal end of the device, e.g., movement of one link of a pair or translational movement of a finger slide, is proportionally scaled to the movement at the distal end of the mechanism, e.g., at the other link of the pair or at the effector portion.

BRIEF DESCRIPTION OF THE DRAWINGS

FIGS. 1A-1E show perspective views of an articulating mechanism according to one variation of the invention, with multiple pairs of links connected by corresponding sets of cables. FIG. 1A shows the mechanism in its natural configuration. FIGS. 1B to 1E show the mechanism in various states of manipulation.

FIG. 1F is a perspective view of the distal end of an articulating mechanism similar to that of FIG. 1A with the end manipulated into multiple curvatures.

FIGS. 2A-2E depict end, side, and perspective views of a link for use in an articulating mechanism according to another variation of the invention.

FIGS. 3A-3C are cross-sectional views of links similar to those of FIGS. 2A-2E having variously shaped stem portions and corresponding recesses. In FIGS. 3A and 3B, the distal end of the stem portions are convex, while in FIG. 3C it is ball-shaped. The recesses are cone-shaped in FIG. 3A, concave in FIG. 3B, and ball-shaped in FIG. 3C.

FIG. 3D is a cross-sectional view of links for use in an articulating mechanism according to another variation of the invention with spherical elements disposed between the links. FIG. 3E is a cross-sectional view of links and spherical elements similar to those of 3D and which also include a center channel extending through and communicating between the links and spherical elements.

FIGS. 4A-4C are cross-sectional views of links for use in an articulating mechanism according to a variation of the invention showing various modes of connecting cables to the links.

FIGS. 5A and B show an individual link for use in an articulating mechanism according to another variation of the invention. FIG. 5A is a perspective view. FIG. 5B is an end view. The depicted link includes lumens and channels for receiving and passing through of cables and other elements.

FIGS. 6A-6C show perspective views of articulating mechanisms associated with a surgical clamp according to variations of the invention.

FIG. 7 is a perspective view of an articulating mechanism associated with a catheter according to a variation of the invention.

FIG. 8 is a perspective view of an articulating mechanism associated with an endoscope according to another variation of the invention.

FIGS. 9A and 9B are perspective views of an articulating mechanism used to remotely form a retractor. In FIG. 9A, the retractor is "u" shaped. In FIG. 9B, the retractor has a triangular retracting surface.

FIG. 9C is a perspective view of an articulating mechanism according to another variation of the invention where the mechanism is attached to the hand of a user.

FIGS. 10A-10B show perspective views of an articulating mechanism according to another variation of the invention having a continuous flexible member that includes helical segments with multiple pairs of such segments connected by corresponding sets of cables. FIG. 10B is an enlarged view, with parts broken away, of the helical segments shown in FIG. 10A.

FIG. 11 is a perspective view of an articulating mechanism according to yet another variation of the invention having a continuous flexible member with a plurality of through lumens with multiple pairs of segments connected by corresponding sets of cables.

FIGS. 12A-12B are perspective views of distal ends of an articulating mechanism according to a further variation of the invention having attached tissue ablation elements.

FIGS. 13A-13F show the distal end of an articulating mechanism according to FIG. 12 being remotely maneuvered to create ablative cardiac lesions.

FIG. 34 is an exploded view of an effector $111k$ that forms a part of the effector portion of FIG. 30.

DETAILED DESCRIPTION OF THE INVENTION

Figure 14:
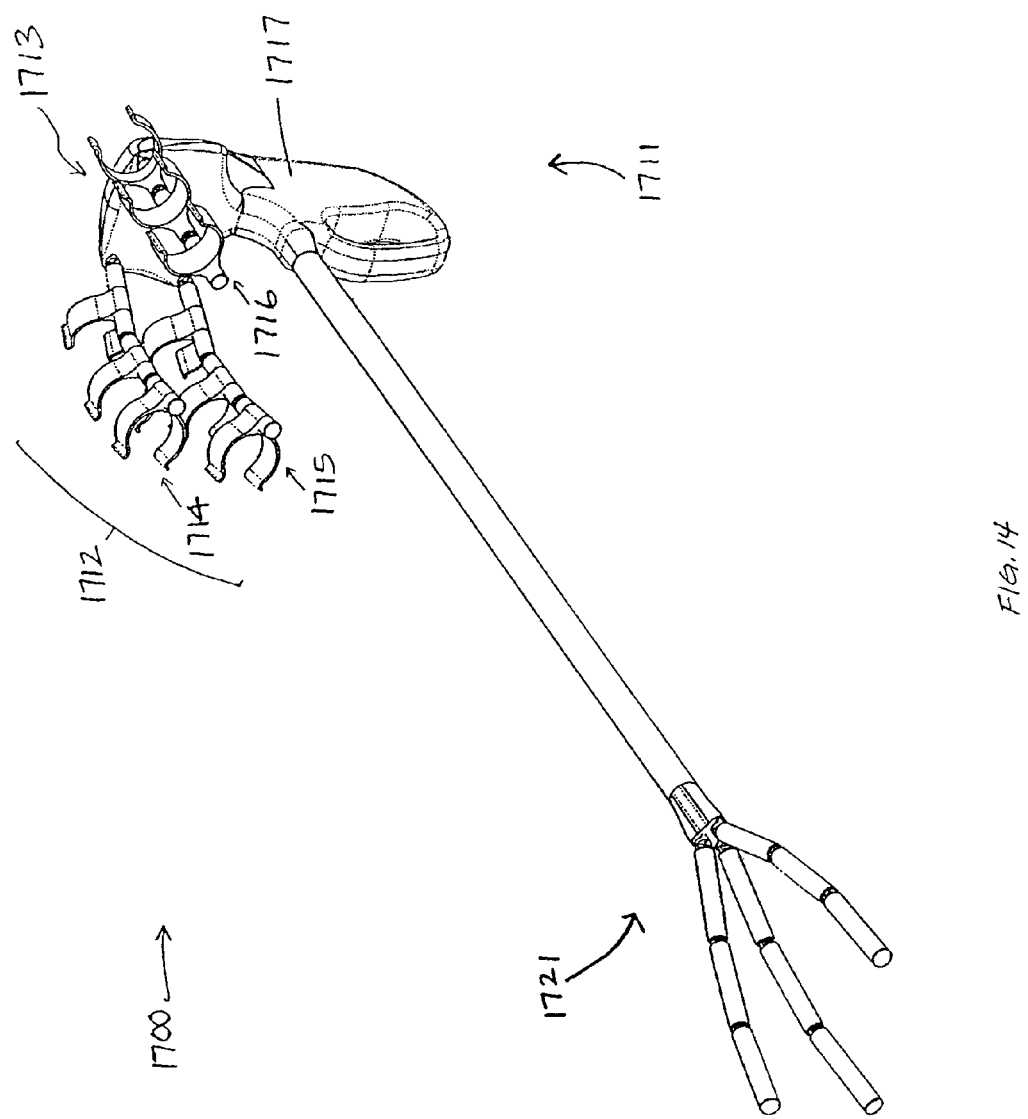
FIG. 14 is a perspective view of a hand-actuated apparatus having finger loops according to one variation of the invention. The apparatus is shown in an unactuated state.

Articulating mechanisms according to the invention generally include multiple pairs of links or segments and multiple sets of cables. The articulating mechanisms may be made from individual, spaced apart segments, i.e., links, or from segments formed from a continuous flexible member. The terms "link" and "segment" as used herein refer to a discrete portion or defined area at one end of the mechanism that corresponds to another discrete portion or defined area at the opposite end of the mechanism. In any event, the articulating mechanism will include a plurality of links or segments that are members of discrete pairs. The links or segments form a proximal end and a distal end, with one link or segment of each pair being situated at the proximal end, and the other link or segment at the distal end. As further described below, links or segments formed from a continuous flexible member may be in the form of, e.g., a continuous tube, or may be situated in, e.g., a helical arrangement, where each segment corresponds to one turn of the helix.

Each cable set connects the links or segments of a discrete pair to one another so that movement of one link or segment of a pair causes a corresponding movement of the other link or segment in the pair. The ability to manipulate individual links allows for the mechanism to readily form complex three-dimensional configurations and geometries as is further detailed herein. With conventional articulating devices that rely on cable sets or wires, it is difficult to obtain such complex geometries because such devices are typically designed such that the steering cables or wires pass through each segment and terminate in a distal-most segment. Thus, all the segments bend together in a coordinated response to movement of the wire or cable set, typically in a curved, or arcuate fashion. For example, the device described by Alotta et al. in U.S. Pat. No. 5,916,146 has such a configuration.

For purposes of illustration, articulating mechanisms of the invention will be described in the context of use for the remote guidance, manipulation and/or actuation of surgical or diagnostic tools and instruments in remote accessed regions of the body, or for the remote manipulation of body tissues. The terms "instrument" and "tool" are herein used interchangeably and refer to devices that are usually handled by a user to accomplish a specific purpose. The term "region" as used herein refers to any solid organ (e.g., liver, kidney, brain, heart) or hollow organ (e.g., esophagus, intestines, stomach, bladder), any solid or luminal (e.g., blood vessels or ducts) tissue, or any body cavity (e.g., sinus, pleural or peritoneal space), in their diseased or nondiseased state. Other applications of the articulating mechanism besides surgical or diagnostic applications are also contemplated and will be apparent to one of skill in the art. These include, without limitation, industrial uses, such as for the navigation of a tool, probe, sensor, etc. into a constricted space, or for precise manipulation of a tool remotely. Other uses include applications where remote manipulation of complex geometries is also desirable. These include uses in recreation or entertainment, such as toys or games, e.g., for remote manipulations of puppets, dolls, figurines, and the like.

Turning to the variation shown in FIG. 1A, articulating mechanism 100 includes a plurality of links 102 that form a proximal end 106 and a distal end 108. Links $A_1$ and $A_2$, $B_1$ and $B_2$, and $D_1$ and $D_2$, respectively, are members of a discrete pair, and one link of a pair is at the proximal end 106 while the other is at the distal end 108. Links $C_1$ and $C_2$ are spacer links, as will be described in greater detail herein. The proximal links ($A_1$, $B_1$, $D_1$) are connected to the distal links ($A_2$, $B_2$, $D_2$) by cables 104. A spacer element 112 is disposed between the proximal end 106 and the distal end 108 to separate the proximal links from the distal links and to maintain them in a spaced apart relationship. The spacer element 112 may be of any length appropriate to the intended application, and is typically hollow so that it may accommodate all the cables 104 that connect the link pairs, as well as additional cables, wires, fiberoptics or other like elements associated with a desired tool or instrument used in conjunction with the mechanism.

The links may be of any size and shape, as the purpose dictates, but their form usually depends on such factors as patient age, anatomy of the region of interest, intended application, and surgeon preference. Links 102, for example, are generally cylindrical, and include channels for passage of the cables that connect the link pairs as well as additional cables, wires, fiberoptics or other like elements associated with a desired tool or instrument used in conjunction with the mechanism. The channel diameters are usually slightly larger than the cable diameters, creating a slip fit. Further, the links may also include one or more channels for receiving elements of attachable surgical instruments or diagnostic tools or for passage of cables that actuate them. The links may typically have a diameter from about 0.5 mm to about 15 mm or more depending on the application. For endoscopic applications, representative diameters may range from about 2 mm to about 3 mm for small endoscopic instruments, about 5 mm to about 7 mm for mid-sized endoscopic instruments, and about 10 mm to about 15 mm for large endoscopic instruments. For catheter applications, the diameter may range from about 1 mm to about 5 mm. Overall length of the links will vary, usually depending on the bend radius desired between links.

In the variation shown in FIGS. 2A-2E, links 200 are generally cylindrical and also include stem portion 202. Links 200 may be aligned so that the distal end 206 of stem portion 202 engages a corresponding recess 208 formed in the surface 210 of an adjacent segment. The distal end of the stem portion may be of various shapes. For example, links 200a and 200b have convex ends 206a and 206b, respectively, (FIGS. 3A, 3B) whereas link 200c has a ball-shaped end 206c (FIG. 3C). Similarly, the corresponding recesses may be of various corresponding shapes, e.g., concave as in recesses 206b and 206c (FIGS. 3B and 3C) or cone-shaped as in recess 206a (FIG. 3A), so long as it permits each link to engage one another and does not restrict the required range of motion for the articulating mechanism.

The stem portion 202 may typically have a length between about 0.5 mm to greater than about 15 mm and a diameter between about 0.5 mm to about 2.5 mm. For endoscopic applications, the stem diameter may range from about 1 mm to about 1.5 mm. Links 200 also include a plurality of channels 212 for passage of the cables that connect the link pairs, as shown in FIGS. 2A-2E. Link 500, as shown in FIG. 5, is designed with an attachment channel 502 that communicates with the segment exterior and is located toward the periphery of the segment, for mounting other elements, e.g., energy sources (for ablation or coagulation) or fiberoptics, or flexible endoscopes, at the distal end of the articulating mechanism. More than one link or segment may include an attachment channel so that the attachment channel may extend from the distal end to the proximal end of the mechanism. Cables, wires, fiberoptics, flexible endoscopes and the like, may also be run through a central channel 504 if desired.

The links or segments may be made from any biocompatible material including, but not limited to, stainless steel; titanium; tantalum; and any of their alloys; and polymers, e.g., polyethylene or copolymers thereof polyethylene terephthalate or copolymers thereof, nylon, silicone, polyurethanes, fluoropolymers, poly (vinylchloride); and combinations thereof.

A lubricious coating may be placed on the links or segments if desired to facilitate advancement of the articulating mechanism. The lubricious coating may include hydrophilic polymers such as polyvinylpyrrolidone, fluoropolymers such as tetrafluoroethylene, or silicones.

A radioopaque marker may also be included on one or more segments to indicate the location of the articulating mechanism upon radiographic imaging. Usually, the marker will be detected by fluoroscopy.

Each link or segment at the proximal end of the articulating mechanism is connected to its corresponding link or segment at the distal end by two or more cables. Each cable set may be made up of at least two cables. As noted, movement of one pair is controlled by its corresponding cable set and is independent of any other pair. In certain variations, for example, a cable set will include three cables spaced 120 degrees apart. By using a set of three cables to connect each link or segment pair, each link or segment pair can be manipulated or moved in three degrees of freedom, independently of any other pairs. By combining a plurality of link or segment pairs, multiple degrees of freedom are achieved, allowing the articulating mechanism to be shaped into various complex configurations. For example, the variation shown in FIG. 1F has a total of nine link pairs each independently connected by sets of three cables each, for possible motion in 27 degrees of freedom. Such multiple degrees of freedom are not available in typical conventional mechanisms where only a single set of cables is employed to manipulate the links.

Cable diameters vary according to the application, and may range from about 0.15 mm to about 3 mm. For catheter applications, a representative diameter may range from about 0.15 mm to about 0.75 mm. For endoscopic applications, a representative diameter may range from about 0.5 mm to about 3 mm.

Cable flexibility may be varied, for instance, by the type and weave of cable materials or by physical or chemical treatments. Usually, cable stiffness or flexibility will be modified according to that required by the intended application of the articulating mechanism. The cables may be individual or multi-stranded wires made from material, including but not limited to biocompatible materials such as nickel-titanium alloy, stainless steel or any of its alloys, superelastic alloys, carbon fibers, polymers, e.g., poly (vinylchloride), polyoxyethylene, polyethylene terephthalate and other polyesters, polyolefin, polypropylene, and copolymers thereof; nylon; silk; and combinations thereof, or other suitable materials known in the art.

Referring to FIG. 1A, cables fixed to a proximal link travel through a spacer element 112 to connect with a corresponding distal link of the pair. As shown in FIGS. 1B-1E, movement of proximal links results in inverted, reciprocal movement of distal links. In other variation, the cables can be twisted or rotated 180 degrees while running through the spacer element 112 so that the reciprocal movement at the distal end 108 is mirrored. The articulating mechanisms of this invention may be configured to include cables twisted in any amount between 0 degrees to 360 degrees to provide for 360 degree range of reciprocal motion.

The cables may be affixed to the links of a pair according to ways known in the art, such as by using an adhesive or by brazing, soldering, welding, and the like. FIG. 4a shows cable 401 affixed within channel 402 of link 410 in such manner. In another variation depicted in FIG. 4B, a cable terminator 400 is mounted, e.g. crimped, brazed, welded, or glued, onto cable end 404 to prevent its slippage through the channel 402. In a further variation, as shown in FIG. 4C, the cable terminators 400 are swaged to form a chamfer within channel 402 so that a friction fit is made between the cable end 404 and cable terminators 400.

FIGS. 10A and 10B show a variation of the invention. Rather than individual links or segments, the segments of articulating mechanism 130 are formed from a continuous flexible member, depicted as an elongated coil. Each turn of the coil is a helical segment 131 of the articulating mechanism. The segments 131 are of a thickness that allow channels 105 to run through them, parallel to the axis of the coil. The helical segments at the proximal end 107 form discrete pairs with segments at the distal end 109. Each segment pair is connected by its own set of cables 111. A spacer element 113 is also disposed between the proximal end 107 and distal end 109 to separate the proximal segments from the distal segments. The cables can be affixed to the helical segments as previously described.

In yet another variation of the invention, as shown in FIG. 11, articulating mechanism 132 is formed of a continuous tube 115 having multiple lumens 117 running through the entire length of the tube. The continuous tube 115 may also optionally include central lumen 119. Cable sets may run the length of the tube and be anchored at varying corresponding axial locations at the proximal and distal ends with, e.g., an epoxy, or run between each segment of a pair and be anchored at or in the vicinity of each segment at the proximal and distal end. For example, at the mechanism proximal end 121, one cable set may be anchored at $A_1$, another at $B_1$, and another at $C_1$. Each cable set would then be anchored at a corresponding location at the mechanism distal end 123, e.g., at locations $A_2$, $B_2$, and $C_2$.

The cables that run between segment pairs may be precisely cut to a certain length, but if desired, may be cut to approximate that length. One method of placing the cables involves advancing the cables through the lumens using a pusher. A visual marker or tactile stop on the pusher would indicate how far to advance the pusher. After the pusher is removed, a needle may be introduced into each lumen to deposit epoxy from, e.g., a syringe exterior to the tube, at each cable end. In another method, which for example can be used with cable sets running the entire length of the tube, the needle may be directed to puncture through the wall of the tube at or near each desired cable attachment point to deliver epoxy to the cable at the desired point, thereby attaching each cable to each corresponding segment pair.

Although the many of the articulating mechanisms have been illustrated in the above figures as having only eight links (four pairs), this is solely for the illustrative purpose of indicating the relationship of the individual device components to one another. Any number of links and link pairs may be employed, depending on such factors as the intended body region of use and desired length of the articulating mechanism. For example, articulating mechanism 101 of FIG. 1F has nine link pairs.

Spacer links, i.e., links not connected by discrete sets of cables (e.g., $C_1$ and $C_2$ in FIGS. 1A-1E), may also be included in the articulating mechanisms. These links can be inserted between active links at either the proximal or distal ends or both, and act as passive links that are not independently actuatable, but do allow for pass through of cable sets to neighboring active links. Spacer links can be desirable for providing additional length to the proximal or distal end. In addition the inclusion of spacer links at one end of the mechanism allows for the proportional scaling of movement or motion of the corresponding other end. For example, the inclusion of spacer links at the distal end would require a more exaggerated movement by the user at the proximal end to achieve to achieve the desired motion at the distal end. This could be advantageous in situations where fine, delicate controlled movements were desired, such as, for example, situations where there is a risk that a user may not possess the necessary dexterity to perform the desired procedure absent such proportional scaling of the distal end movement or motion. Alternatively, spacer links could be provided on the proximal end, in which case the degree of distal end movements would be proportionally greater than those of the proximal end, which may also be desirable for particular applications.

As noted, the articulating mechanisms of this invention may be used to direct a surgical or diagnostic instrument tool within a body region or to a target site within a body region of a patient either in its native, straight configuration, or after undergoing various manipulations at its proximal end from a location outside the patient. After appropriate insertion, movement of the proximal end of the mechanism, results in reciprocal movement at the distal end. Further, the resulting directional movement of the distal end can be inverted, mirrored or otherwise, depending on the degree of rotation of the proximal end relative to the distal end. Also, the proximal end provides for a user interface to control the steering and manipulation of the distal end that is convenient and easy to use relative to other conventional steering mechanisms that rely on e.g., pulleys or knobs to control steering wires. This user interface allows for example a user to readily visualize the shape and directional movement of distal end of the mechanism that is located e.g. within a patient based on the manipulated shape of the externally positioned proximal end user interface.

Complex movements, including up, down, right, left, oblique, and rotational movements, may be accomplished due to the formation of multiple pairs of segments or links connected by discrete cable sets, as described above. For example, in the variation shown in FIG. 1B, the most distal link at the distal end, $A_2$, may be actuated, while all other links remain stationary by actuation of the most distal link at the proximal end, $A_1$. For illustrative purposes, the distal-most link is shown to be rotated to form a right circular cone 114a, the base diameter of which increases with such factors as increased length of stem portions, enhanced cable flexibility, and addition of spacer links 103 (e.g., $C_1$) in addition to the other links.

As shown in FIG. 1C, the most proximal link at the distal end, $D_2$, is actuated while all other links remain stationary by actuating only the most proximal link at the proximal end, link $D_1$. Upon rotation, the base diameter of the right circular cone 114b is larger than cone 114a in FIG. 1B due to the increased number of segments being actuated (thereby increasing the slant height).

If a middle link is actuated at the proximal end, e.g., $B_1$, in FIG. 1D, while all other links remain straight or stationary to one another, than only the corresponding middle link at the distal end, $B_2$, will be manipulated and may be rotated to form, e.g., a cone with curved sides 116a. Or, as shown in FIG. 1E, a larger cone with curved sides 116b may be formed by manipulating the distal-most link, $A_1$, so that all proximal links bend into a curve. All links at the distal end will then mimic the curve, in an inverted fashion.

Although rotational movements are depicted in FIGS. 1B-1E, again, other complex, 3-dimensional movements incorporating up, down, right, left, and oblique movements, may also be accomplished. For example, FIG. 1F shows the distal end 120 of an articulating mechanism having multiple curvatures (122, 124, 126) along its length, each oriented in directions independent of one another. As noted, articulating mechanism 101 of FIG. 1F has nine pairs of links with three cable sets each providing for movement in 27 degrees of freedom, but other configurations of link pairs and cable sets will readily achieve similar complex movements and geometries. The ability of portions the mechanism to bend in different directions at the same time and create active complex configurations is provided by the independent actuation of each link or segment pair as controlled through its corresponding cable set.

The natural configuration of the segments, when connected by cable sets, is usually linear. Thus, if maintenance of a certain curvature or other complex configuration is desired at the distal end of the articulating mechanism, a malleable tube slidable over the proximal segments may be shaped to keep the proximal segments, and thus, their corresponding distal segments in a particular configuration. This may be advantageous where, for example, a surgeon has navigated the mechanism to a desired target location and wishes to "lock" the mechanism in place while e.g. actuating a tool associated with the mechanism, or engaging in a separate procedure altogether. By the term "malleable" it is meant that the tube is flexible enough so that it is capable of being shaped, but rigid enough so that it maintains its shaped form. In another variation, a locking rod may be inserted into one or more attachment channels extending through the links or segments to "lock" the proximal and distal segments of the articulating mechanism in place. The locking rod may be a malleable metal bar that may be shaped and then inserted into the attachment channels to set the proximal and distal segments into a particular configuration, or the locking rods may be provided in preshaped forms.

Other methods of freezing or locking the articulating mechanism in place include the general use of links configured with ball-and-socket type joints together with a tensioning cable. Examples of such systems are generally described in e.g. U.S. Pat. No. 5,899,425 to Corey, Jr. et al. In such systems, a cable passing through the joints is tensioned, causing the balls and sockets to lock together frictionally. The cable can be tensioned by number of ways, including e.g. by affixing the end of the tensioning cable to a screw that is threaded into a nut affixed to the proximal end of the mechanism. FIGS. 3D and 3E illustrate ball-and-socket type link systems for use in articulating mechanisms of the invention. As shown, in FIG. 3D, each link 300 has a recessed socket 301 for receiving a spherical element or ball 302 disposed between the links. When a tension force is applied linearly along the axis of the links, the links will lock into place due to frictional forces between the balls and sockets. FIG. 3E shows a link system of similar configuration, with each link 310 and ball 312 having aligned channels 313 and 314 for the passage of a tensioning cable. Other mechanisms for locking the articulating mechanism in place in a fixed, articulated position include but are not limited to those described in U.S. application Ser. No. 10/928,479, filed on Aug. 26, 2004, incorporated herein in its entirety.

The articulating mechanism may be employed for remote manipulation of surgical instruments, diagnostic tools, various catheters, and the like, into hollow or chambered organs and/or tissues including, but not limited to, blood vessels (including intracranial vessels, large vessels, peripheral vessels, coronary arteries, aneurysms), the heart, esophagus, stomach, intestines, bladder, ureters, fallopian tubes, ducts such as bile ducts, and large and small airways. The articulating mechanism may also be used to remotely direct surgical instruments, diagnostic tools, various catheters, and the like, to solid organs or tissues including, but not limited to, skin, muscle, fat, brain, liver, kidneys, spleen, and benign or malignant tumors. The articulating mechanism may be used in mammalian subjects, including humans (mammals include, but are not limited to, primates, farm animals, sport animals, cats, dogs, rabbits, mice, and rats).

The articulating mechanisms may generally be used in any application or incorporated into other devices in which there is a user interface proximally, and an actuating element distally. The user interface may include the proximal end of an articulating mechanism, while the distal end may be attached to the actuating element. For example, in FIG. 6A, a remotely maneuverable surgical clamp 600 is shown. The clamp jaws 602 are attached to the distal end 604 of the articulating mechanism. The proximal end 606 is built into the clamp handle 608. A user is able to remotely position the clamp jaws 602 by manipulating the proximal end 606 of the articulating mechanism. A middle portion ("neck") 610 is also provided with the surgical instrument, the length and flexibility of which will vary with the application, with the neck providing the function of the spacer element. FIG. 6C shows another variation, where clamp handle 632 of surgical clamp 630 extends from proximal end 634. In other variations, the clamp jaws 602 may be exchanged for scissors or other cutting element, a dissector, a tissue grasper or needle grasper, a stapling device, a cauterizing or ablation device, and or other like tool or instrument.

In a further variation, the articulating mechanism itself may form the clamp jaws. In FIG. 6B, the clamp 612 has a user end with the proximal segments 614 extending from pivot 616 of the clamp. The cables that originate in the proximal segments 614 bifurcate into two cables each in the area of the pivot 616 so that each cable in the proximal end may then terminate in two separate articulating mechanisms that form opposing clamp jaws 618, 618. Thus, when a user manipulates the proximal segments 614, the jaws 618 will remain aligned and be correspondingly remotely manipulated. If desired, the proximal segments 614 may extend and be manipulated from one of the handles 620 of the clamp. The jaws can further be configured with particular tissue engaging surfaces, as well as ablation elements.

In yet a further variation, the articulating mechanism can be incorporated into a catheter and used to guide the catheter, e.g., in difficult central line placements, or in percutaneous or image-guided drainage catheter placement. As shown in FIG. 7, a catheter 700 may include an articulating mechanism with the proximal end of the mechanism 702 configured as an integral component of the user interface, in this instance, handle 706. The distal segments 708 form the distal portion of the catheter, and may be remotely maneuvered to guide the catheter 700 as it is advanced. In another variation (not shown), the articulating mechanism may be threaded through the catheter like a guidewire such that the proximal segments extend from the catheter proximal end, e.g., either directly from the catheter lumen, or from a bifurcated wye connector. The distal segments may extend from the catheter tip, and the catheter remotely guided to its target position as it is advanced. Typically, the articulating mechanism would then be removed to allow flow through the catheter. However, if the articulating mechanism that is employed has a central lumen, its removal may not be necessary.

In the same fashion, the articulating mechanism can be incorporated into and used to steer a flexible endoscope. In FIG. 8, endoscope 800 is configured such that the proximal end 806 of the articulating mechanism forms an integral part of the endoscope handle 804. The distal end 808 of the mechanism would constitute all or a part of the endoscope insertion tube 810. Upon manipulation of the proximal segments 806, the insertion tube 810 may be remotely manipulated.

In another variation, as shown in FIGS. 9A and 9B, the articulating mechanism could be used as a hand-held or self-retaining retractor 900. The proximal segments 902 and distal segments 904 may extend from the retractor handle 906. Manipulation of the proximal segments 902 will move the distal segments 904 in a reciprocal fashion. The distal segments can be manipulated to form a variety of complex shapes, the desired shape depending on the particular application. In operation, the distal end can be first positioned into the desired shape and then engaged with the target tissue. Alternatively, tissue retraction can be performed concurrently with manipulation of the distal end, i.e., the distal end can be engaged with the target tissue and through the act of manipulating the distal end, the tissue can be retracted.

A retractor typically must maintain its shape in use. Thus, the retractor may be "locked" into place using e.g. methods previously described. For example, the mechanism can include links with a ball and socket configuration together with a locking cable (not shown). Alternatively, a malleable sheath (not shown) may be placed over the proximal segments 902 prior to their manipulation or a locking rod (not shown) may be used to fix the retractor in a particular configuration, as has been previously described. In FIG. 9A, the retractor 900 is "u" shaped. In FIG. 9B, the retractor 900 has a triangular retracting surface. As noted, a retractor shape may be varied, depending on factors such as anatomical structure involved or type of surgical procedure.

In another variation, a number of articulating mechanisms can be combined in such a way that a user's finger movements can be remotely mimicked. For example, proximal ends of the mechanisms can be affixed to a user's fingers, for example, either strapped to each digit or otherwise secured to a glove that the user can wear. The distal ends will then move according to the user's finger movements. As used herein, the terms "finger" and "digit" will be used interchangeably, and refer to the thumb, index finger, middle finger, ring finger, and pinky. In the variation shown in FIG. 9C, mechanism 950 includes three articulating mechanisms operable by movement of a user's thumb, index, and middle fingers. As can be seen, proximal ends 951, 952 and 953 are affixed to a user's thumb, index finger and middle finger, respectively, by straps 957. The mechanism is further secured to the user's hand by strap 958 which secures the proximal end of spacer element 956 to the user's wrist. Movement of the user's thumb, index finger, and middle finger causes corresponding movement of distal ends 961, 962 and 963, respectively. Such variations may be advantageous in various surgical situations where gross manipulation of tissue or organs is required. In this as well as other variations, a protective pliable sheath can be extended over the mechanism to avoid potential damage to tissue from individual links or cables.

In yet further variations, the articulating mechanisms or combinations of articulating mechanisms described above that mimic finger movement (also generally referred to herein as hand-actuated devices) and that include a user hand interface at the proximal end of the device for removably securing a digit of a human hand, may be further modified such that the user hand interface is also configured to removably engage with the palm (ventral surface) of the hand. The interface generally includes two portions, a finger portion for actuating movement and releasably securing one or more fingers to the interface, and a handle portion which partially abuts the palm and which provides another surface for releasably securing a user's hand and fingers. The ergonomics of this device configuration is particularly desirable since a user's hand may be quickly engaged and disengaged from the device. The ability to quickly and easily engage or disengage one's hand from the device may be particularly advantageous in, e.g., surgical settings where surgeons typically need to swap surgical tools rapidly. Importantly, although the devices are generally adapted for use by a human hand, and typically include three mechanisms to accommodate the index finger, middle finger, and thumb of the hand, the number of articulating mechanisms that may be included is not so limited, and may include as many mechanism as a user can control at once.

The distal end of the hand-actuated devices usually includes an effector portion that generally mimics the structure and movement of human fingers and which is remotely actuated by corresponding movements at the finger portion of the interface. The effector portion is typically configured to provide such gross movements as gripping and pinching, but also provides for finer finger movements oftentimes required, e.g., for fine tissue manipulation. Thus, in surgical applications, the effector may be used to clamp, provide traction, dissect, debride, suture, or otherwise manipulate body tissues.

Anatomically, human fingers include bones called phalanges. The index finger, middle finger, ring finger, and pinky have three phalanges, commonly referred to as the proximal phalanx, middle phalanx, and distal phalanx. The thumb includes only two phalanges, a proximal phalanx and a distal phalanx. Movement of the phalanges are controlled by finger joints that join the head of one phalanx with the base of the more distal one. Joints at the base of the proximal phalanx (that connect the proximal phalanx to bones of the hand) are metacarpophalangeal (MCP) joints that typically allow flexion, extension, abduction, adduction, and circumduction (movement in two degrees of freedom) of the proximal phalanx. Interphalangeal (IP) joints, on the other hand, which join the distal phalanx to the middle phalanx and/or the middle phalanx to the proximal phalanx, are typically uniaxial hinge joints that permit only flexion and extension (movement in a single degree of freedom).

The hand-actuated devices of this invention are typically made from links adapted in such a way to generally correspond to the anatomical structure of human fingers and generally parallel the range of motion of human finger joints, but can also be configured to provide joint movement in any desired degree of freedom. For example, links can be dimensioned and grouped together so that they look and work similar to human fingers and finger joints. In that vein, links adapted to correspond to phalanges would be, e.g., longer than links used as part of the finger joints (MCP and IP joints). Essentially, a device including components that correspond to the general anatomic structure of human fingers and which generally parallel the function of human finger joints would provide much of the manual dexterity generally associated with the human hand.

The links representative of phalanges may be of any dimension, so long as they are capable of functioning similar to human phalanges, but are typically longer than other links, as mentioned above, and will accordingly be referred to herein as "elongate links". The length of an elongate link may range from a less than a millimeter to a few centimeters, and in some non-medical applications, even several inches. For general surgical use, the length of elongate links corresponding to proximal phalanges may be about 22 mm, for middle phalanges about 17 mm, and for distal phalanges about 15 mm. Elongate links at the proximal end of the device will be generally referred to as "finger links" and those at the distal end of the device will be referred to as "effector links".

The elongate links can take any form that can provide functionality similar to a human phalanx may be used. For example, if desired, the elongate links can be made flexible. The diameter of the elongate links may also vary, depending on factors such as the finger that the link is being associated with (e.g., thumb, index finger, or middle finger) and the device application, but will typically be from about 1 mm to about 20 mm, or more than 20 mm. The diameter of a smaller elongate link may be about 1 mm to about 3 mm, for a mid-range elongate link about 3 mm to about 7 mm, and for a larger elongate link about 7 mm to about 10 mm or more.

The elongate links may be made from any biocompatible material as previously mentioned for links, including, but not limited to, stainless steel; titanium; tantalum; and any of their alloys; and polymers, e.g., acrylonitrile-butadiene-styrene (ABS) terpolymer, Delrin® acetal homopolymers and copolymers, polycarbonate, polyethylene or copolymers thereof, polyethylene terephthalate or copolymers thereof, nylon, silicone, polyurethanes, fluoropolymers, poly (vinyl-chloride); and combinations thereof, or any other suitable material known in the art. The elongate links may also be variously textured to enhance their gripping or traction ability, as will be apparent to one of skill in the art. The elongate links themselves can be textured or a textured material can be applied to the elongate links. In certain variations, the textured material can include tractive surfaces, as disclosed in U.S. Pat. No. 6,821,284, incorporated by reference herein in its entirety.

As previously described, phalanges are joined to one another by human finger joints, i.e., the DIP, PIP, and MCP joints. In a similar fashion, elongate links are connected by joints in the mechanism. As used herein, "joint" refers to discrete links or a discrete combination of links capable of having the range of motion of a DIP, PIP, or MCP joint. At the proximal end of the mechanism, the joint corresponding to an MCP joint will be generally referred to as the "base joint" and the joints corresponding to DIP and PIP joints will be generally referred to as "finger joints". At the distal end of the mechanism, the joint corresponding to the MCP joint will be generally referred to as the "effector base joint" and the joints corresponding to DIP and PIP joints will be generally referred to as "effector joints". The joints may be made from any biocompatible material similar to that used for elongate links, as previously described.

The hand-actuated devices may be formed from a plurality of individually attached elongate links and joints or from elongate links and joints formed integrally with one another. Furthermore, the links and link combinations used as elongate links or joints include those described herein, as well as other suitable links and link combinations, including, but not limited to, those disclosed in U.S. application Ser. No. 10/928,479, filed on Aug. 26, 2004, U.S. application Ser. No. 10/948,911, filed on Sep. 24, 2004, and U.S. application entitled "Articulating Mechanisms and Link Systems With Torque Transmission In Remote Manipulation of Instruments and Tools", filed Nov. 23, 2004, the disclosures of which are herein incorporated by reference in their entirety. Links that are designed to adjust for cable bias, including those described in U.S. application Ser. Nos. 10/928,479 and 10/948,911, are also useful. In order to provide for increased rigidity of the articulating mechanism and hand-actuated devices when manipulated, active links are typically fully constrained so as to resist movement due to laterally applied forces, as is described in U.S. application Ser. Nos. 10/928,479 and 10/948,911. The use of fully constrained links helps to preserve the integrity of the desired shape formed at the distal or proximal end of a manipulated mechanism when in use, and allows force to be distributed across the desired shape. Spacer links on the other hand are typically unconstrained. The provision of spacer links decreases the rigidity of the proximal or distal end in those areas that contain such spacer links or flexible segments, which can be desirable, e.g., when navigating through or around sensitive or fragile anatomical structures.

As previously described, articulating mechanisms of this invention include links at a proximal and distal end of the mechanism. The proximal and distal links form discrete pairs and are connected to each other by cable sets so that movement of one link of a pair causes corresponding movement of the other link in the pair. In the same fashion, hand-actuated devices of this invention include articulating mechanisms having a plurality of elongate links that form members of discrete pairs. The elongate links form a proximal end, or "finger portion", and distal end, or "effector portion", with one elongate link of each pair being situated at the finger portion end, and the other elongate link at the effector portion end. Cable sets run through the joints and connect the elongate links of a discrete pair to one another so that movement of one elongate link of a pair causes a corresponding movement of the other elongate link in the pair, independent of movement of other pairs of elongate links.

The one to one correspondence of movement of elongate links may also be extrapolated to joints. As further described below, articulation of the effector joints may be generally achieved by articulation of a base joint and finger joints at the proximal end of the device or may be achieved by actuation of a finger slide. In some applications, it may be desirable to scale movement of effector links and joints, to either increase or decrease the movement produced at the distal end relative to the corresponding movement at the proximal end, examples of which will be also be provided below. As previously mentioned, proportional scaling of movement in the articulating mechanisms can in general be accomplished by the inclusion of additional spacer links. Proportional scaling of movement in the articulating mechanisms can also be accomplished in general by increasing or decreasing the cable channel pattern radius in the links, at either the proximal or distal end of the mechanism, as is further described in pending and commonly owned U.S. application Ser. No. 10/948,911 incorporated herein by reference in its entirety. For example, if the radial distance of cables from central axis of links of the proximal end is greater than that in the distal end, the degree of bending or flex of the distal end will be proportionally greater than that of the proximal end. The result is that smaller degree of movement at the proximal end will produce a greater degree of movement at the distal end. Alternatively, if the cable radial distance of links of the proximal end is less than that in the distal end, the degree of bending or flex of the distal end will be proportionally less than that of the proximal end, such that movement of the proximal end will be exaggerated relative to the distal end. Proportional scaling of movement will also typically produce scaling of force.

FIGS. 14-17 depict a variation of a hand-actuated device in which articulation of the effector joints may be generally achieved by articulation of a base joint and finger joints at the proximal end of the device. In FIG. 14, the hand-actuated device 1700 has a proximal end 1711 and a distal end 1721. A user interface 1713 at the proximal end 1711 includes a finger portion 1712 and a handle portion 1717. The finger portion 1712 actuates movement at distal end 1701 and releasably secures one or more fingers to the interface 1713. Handle portion 1717 partially abuts the palm and provides another surface for releasably securing a user's hand and fingers. Typically, a user's thumb, index finger, and middle fingers will be releasably secured to finger portion 1712, but any combination of fingers may be releasably secured. In FIG. 14, finger portion 1712 is adapted to releasably secure a user's index finger, middle finger, and thumb in an index finger portion 1714, middle finger portion 1715, and thumb portion 1716, respectively.

Figure 15:
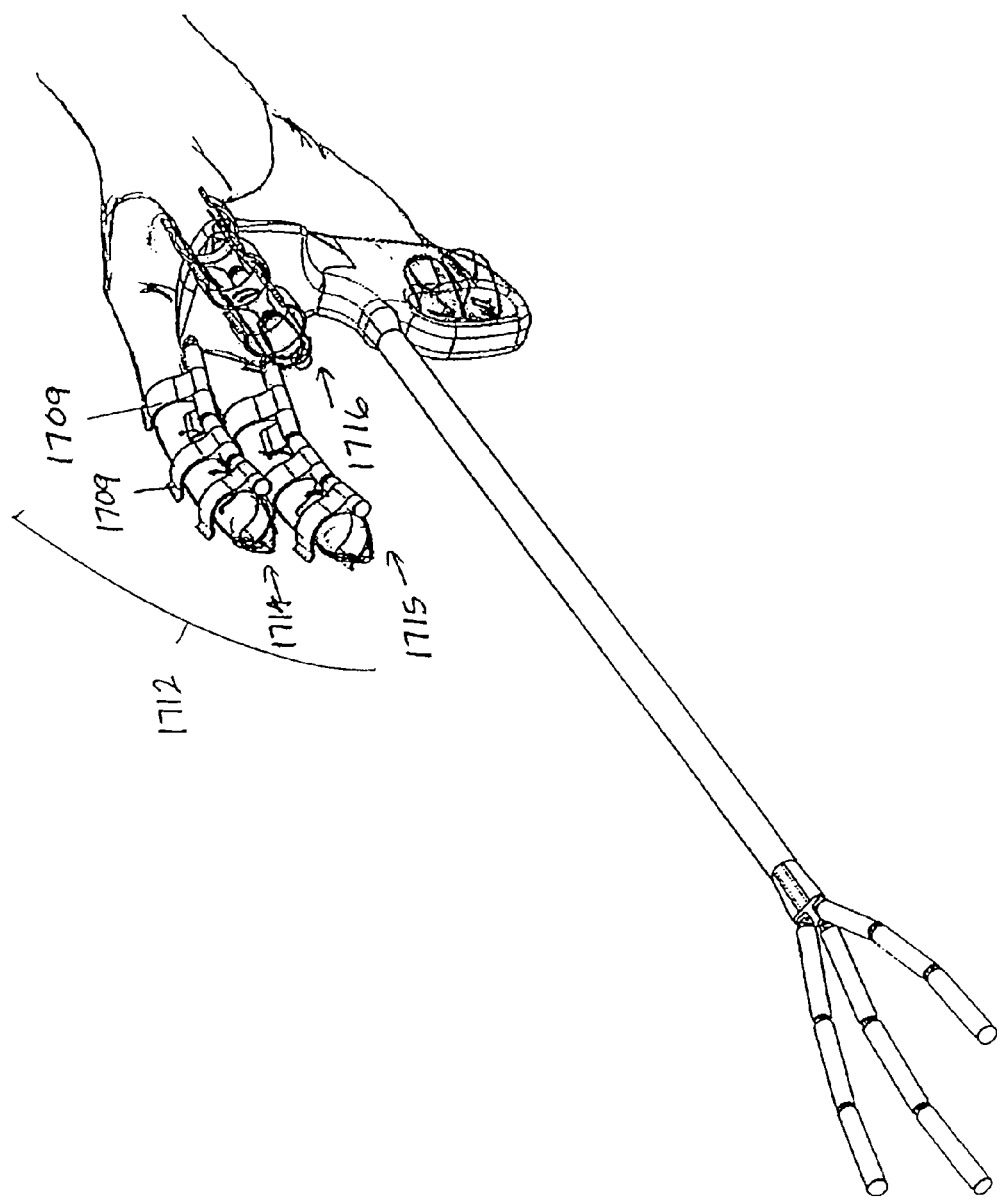
FIG. 15 shows placement of a human hand in the hand-actuated apparatus of FIG. 14.

In one variation, a user's fingers may be releasable secured or releasably engaged to finger portion 1712 by finger loops 1509, as shown in FIG. 15. Specifically, a user's index finger, middle finger, and thumb may be releasable secured to an index finger portion 1714, middle finger portion 1715, and thumb portion 1716, respectively.

Figure 16:
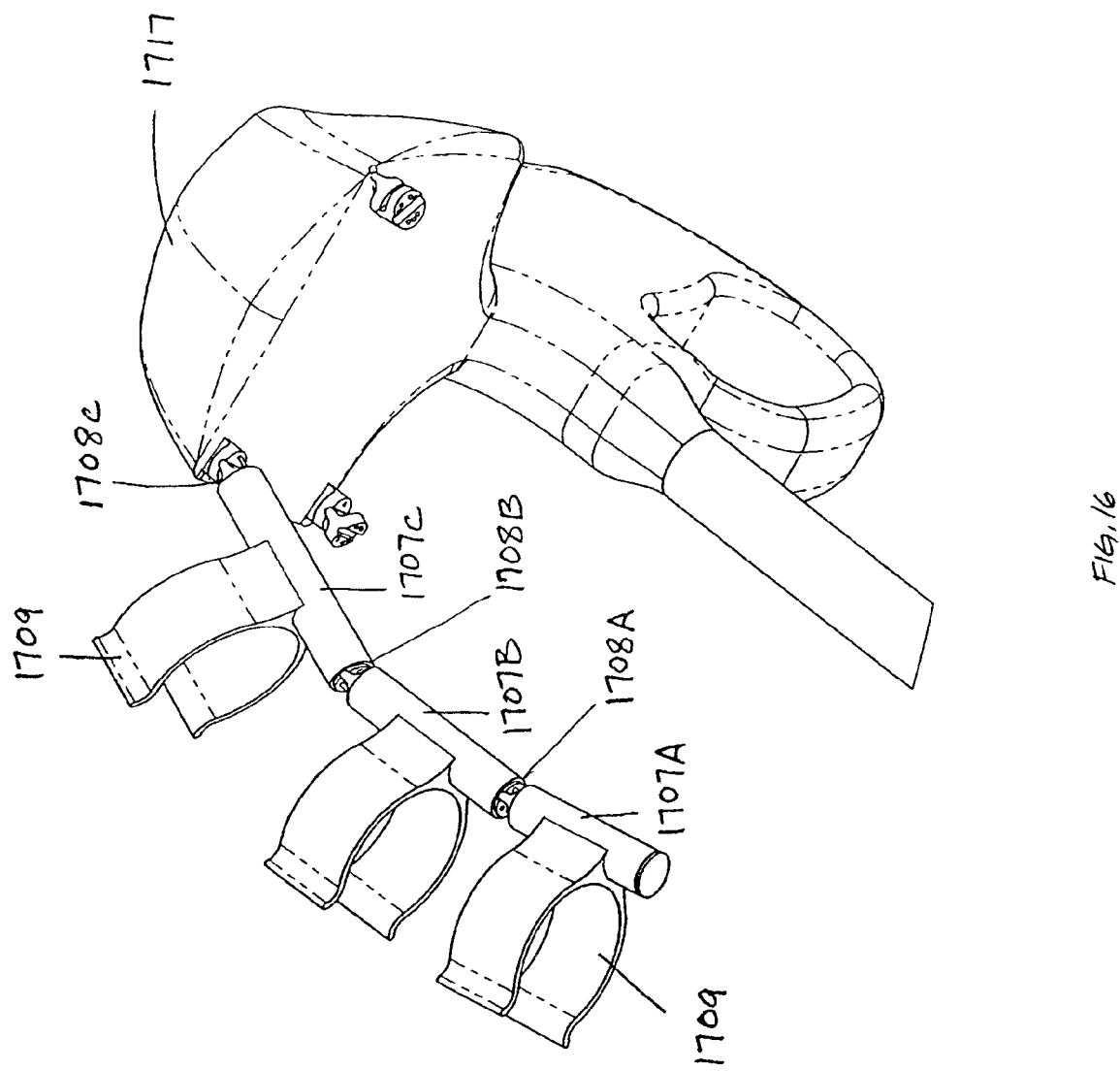
FIG. 16 is an expanded perspective view of the finger loops of FIG. 14.

An enlarged view of an index finger portion is shown in FIG. 16. Finger loops 1709 may be constructed from the same materials as the elongate links described above, and are attached to finger links 1707A, 1707B, and 1707C by techniques well known in the art, such as, but not limited to, fastening, e.g., such as with a mechanical fastener, welding and gluing. Extending between finger links 1707A and 1707B is distal finger joint 1708A, which is configured to have a range of motion similar to a DIP joint. Extending between finger links 1707B and 1707C is another distal finger joint 1708B, which is configured to have a range of motion similar to a PIP joint. Finger link 1707C is coupled to handle portion 1717 by proximal base joint 1708C, which is configured to have a range of motion similar to a MCP joint. The particular structure of the joints will be addressed further below.

The hand-actuated mechanisms of this and other variations also include an effector portion for remote manipulation of, e.g., instruments, tools, or body tissues. In one variation, shown in FIG. 17, effector portion 1701 is shown to include three effectors, 1702, 1703, and 1704, but if desired, the device can be equipped with more or less than three effectors. Similar to finger portions, effectors also include elongate links and joints. Elongate links and joints in the effector portion are generally referred to as "effector links" and "effector joints" respectively, and are also adapted in such a way to mimic human finger/hand movement. Effector links will typically correspond to phalanges, and the range of motion of effector joints will usually parallel that of DIP, PIP, or MCP joints. For example, in FIG. 17, effector links 1705A, 1705B, and 1705C are configured to correspond to a distal phalanx, middle phalanx, and proximal phalanx, respectively, and effector joints 1706A, 1706B, and 1706C are adapted to parallel the function or range of motion of the DIP, PIP, and MCP joints, respectively.

Figure 17:
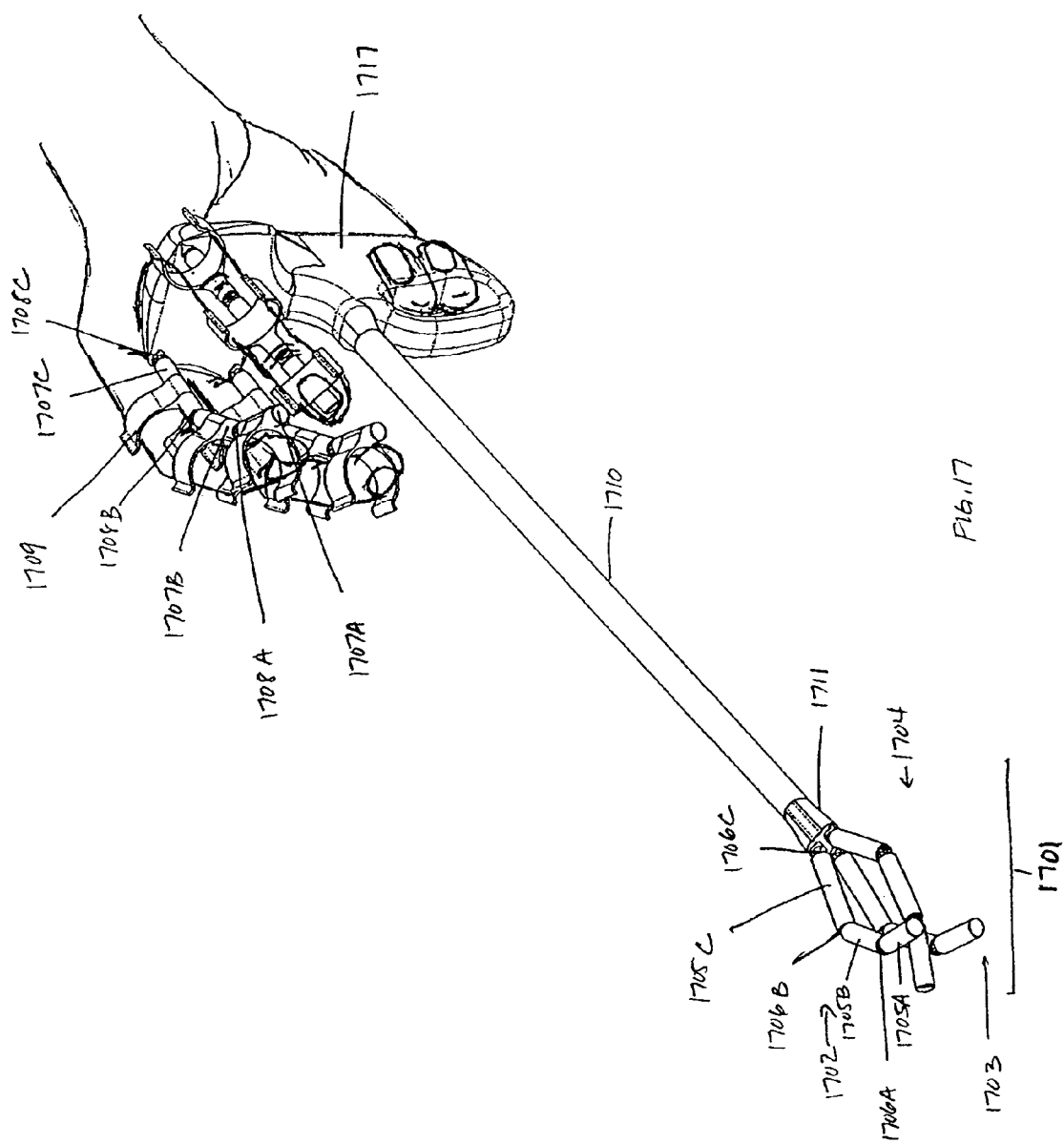
FIG. 17 is a perspective view of the hand-actuated apparatus of FIG. 15 in an actuated state.

In operation, as shown in FIGS. 15 and 17, movement of a user's fingers, e.g., an index finger, middle finger, and thumb, from an open (FIG. 15) position to a closed, grasping position (FIG. 17), correspondingly moves finger links 1707A, 1707B, 1707C and finger joints 1708A, 1708B and effector base joint 1708C because the user's fingers are releasably secured to finger loops 1709 that are also attached to finger links 1707A, 1707B, and 1707C. Cables (not shown) running through the finger links 1707A, 1707B, and 1707C, finger joints 1708A and 1708B, effector base joint 1708C, handle portion 1717, shaft 1710, and effector palm 1711, are actuated by the user's finger movement to produce a corresponding movement of effector portion 1701. Specifically, movement of finger joint 1708A causes a corresponding articulation of effector joint 1706A, movement of finger joint 1708B causes a corresponding articulation of effector joint 1706B, and movement of base joint 1708c causes a corresponding articulation of effector base joint 1706C. Mirrored movement at the effector portion 1701 may be generally achieved by rotating the cables approximately 180.degree. as they travel through the handle portion 1717, or shaft 1710, or effector palm 1711. Mirrored movement may be more intuitive and also desirable in some instances because it allows the effector portion to, e.g., close when a user's fingers are closed, or move right when a user's finger moves right, or move left when a user's finger moves left. Alternatively, inverted movement may be generally achieved by not rotating the cables. In some instances, it may be desirable to provide a combination of mirrored motion and inverted motion in the effector portion.

Although only a thumb, index finger, and middle finger portions are depicted in the user interfaces of FIGS. 14,15, and 17, as well as in other figures, the invention is not so limited. Depending on such factors as the intended use or user preference, the interface may be configured to include a finger portion for releasably securing any number of fingers. In addition, the finger portions may be arranged on the handle portion as illustrated in FIGS. 14-17, but may also be varied to accommodate other arrangements and positions, so long as adequate actuation of the effector portion may be achieved.

Figure 18:
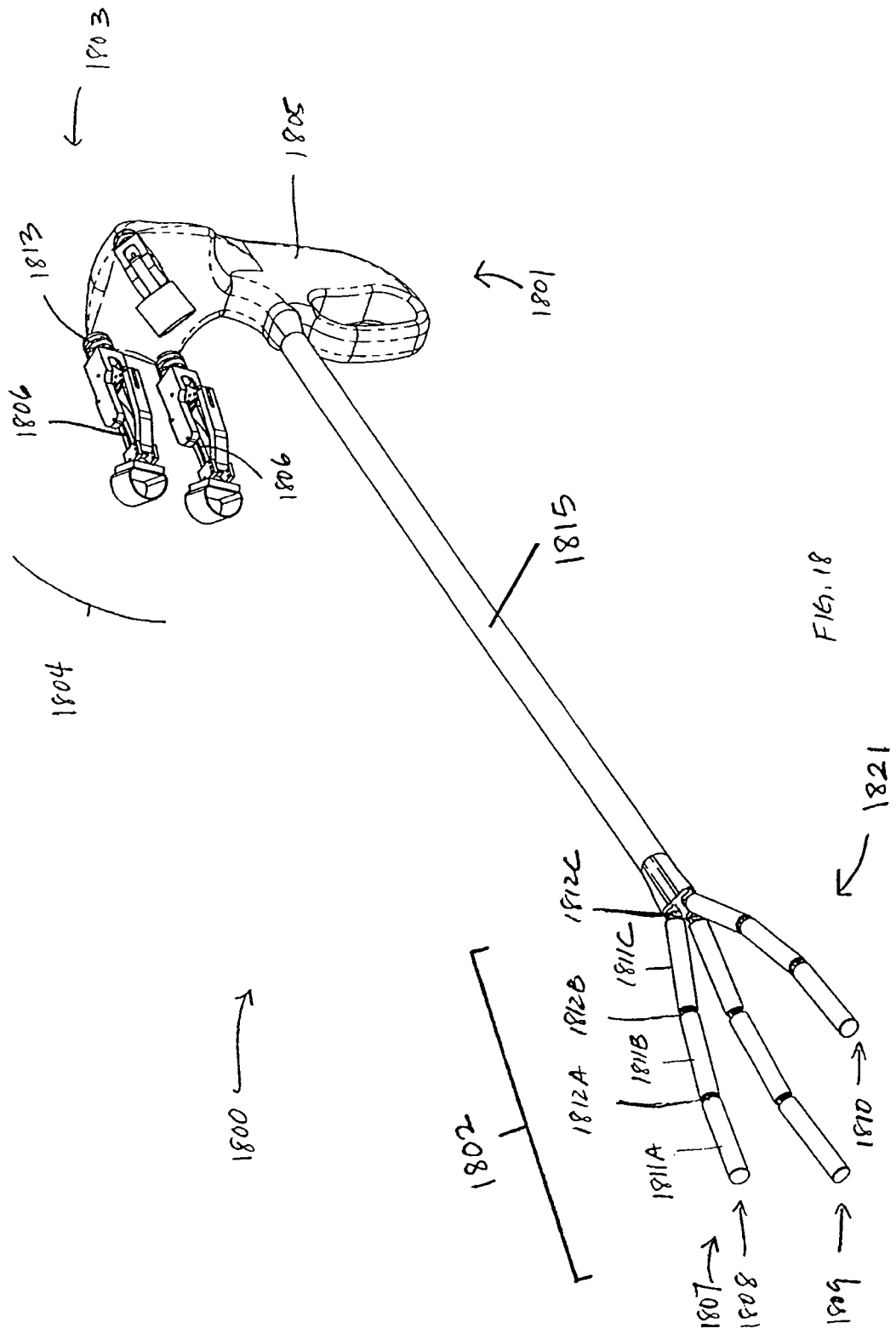
FIG. 18 is a perspective view of a hand-actuated apparatus having finger slides according to one variation of the invention. The apparatus is shown in an unactuated state.
Figure 19:
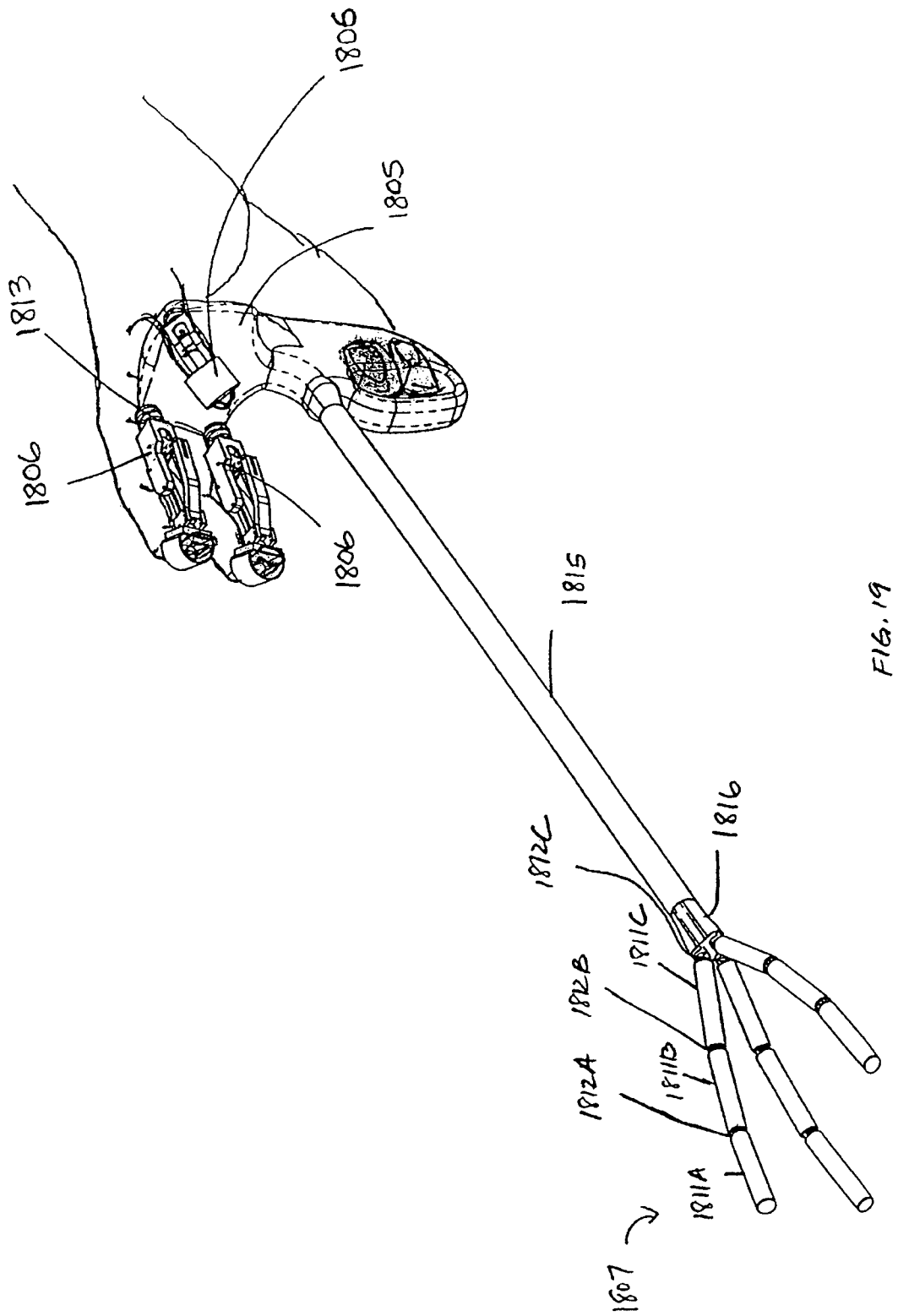
FIG. 19 shows placement of a human hand in the hand-actuated apparatus of FIG. 18.
Figure 20:
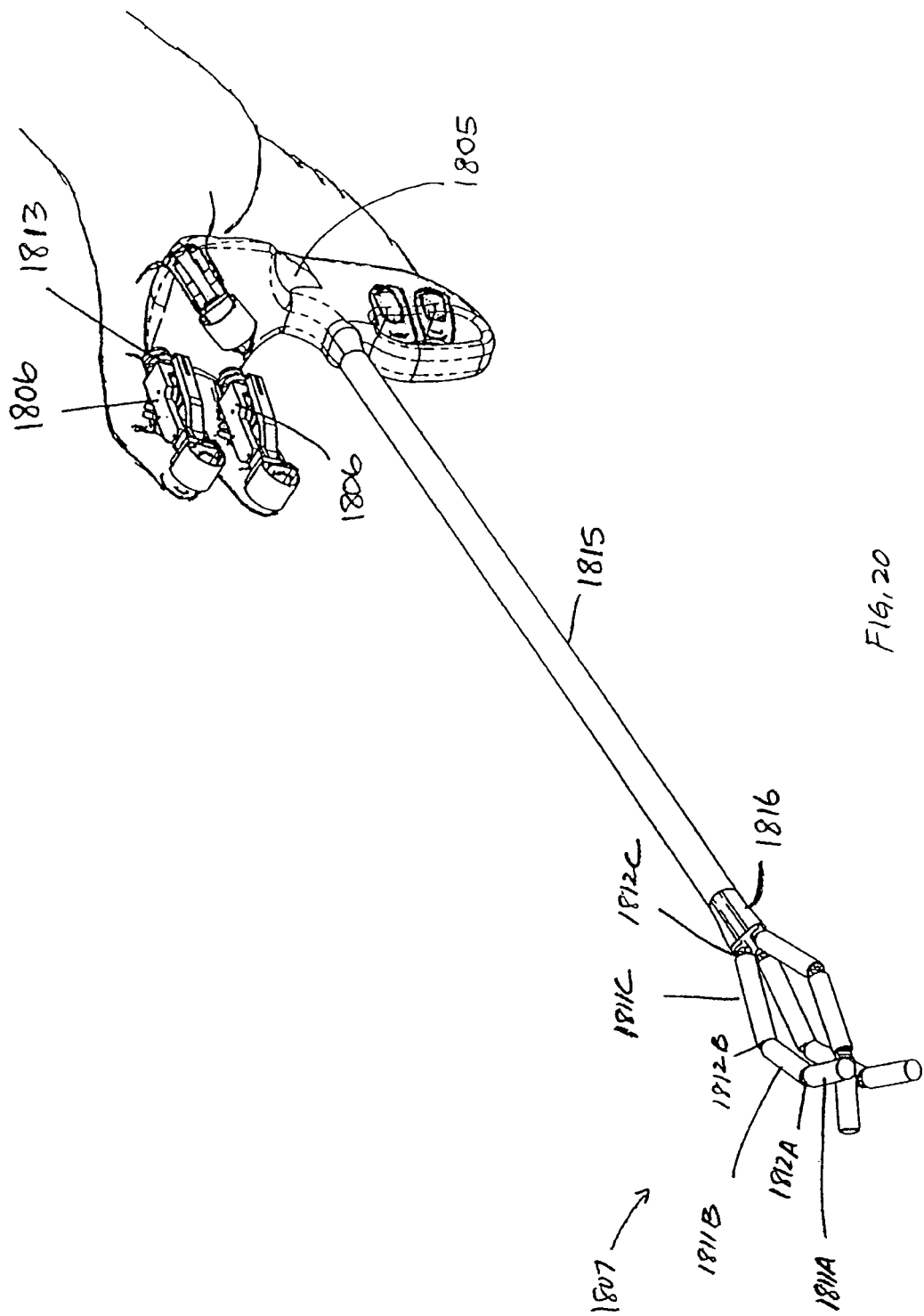
FIG. 20 is a perspective view of the hand-actuated apparatus of FIG. 19 in an actuated state.

FIGS. 18-20 depict another variation of a hand-actuated device in which articulation of the effector joints may be generally achieved by actuation of finger slides. In this variation, as shown in FIG. 18, hand-actuated device 1800 has a proximal end 1801 and a distal end 1821. A user interface 1803 at the proximal end 1801 includes a finger portion 1804 and a handle portion 1805. The finger portion 1804 includes finger slides 1806 for actuating movement at the distal end 1821 and releasably securing one or more fingers to the interface 1803. Handle portion 1805 partially abuts the palm and provides another surface for releasably securing a user's hand and fingers.

Distal portion 1802 includes an effector portion 1807 having effectors 1808, 1809, and 1810. Effectors are made up of effector links and effector joints as previously described. For example, in FIG. 18, effector 1808 includes effector links 1811A, 1811B, and 1811C, and effector joints 1812A, 1812B, and 1812C. In particular, the function of effector joint 1812A parallels a DIP joint, effector joint 1812B parallels a PIP joint, and effector base joint 1812C parallels a MCP joint.

The user interface 1803 of this variation includes finger slides 1806 in addition to a base joint 1813 to actuate movement of effectors 1808, 1809, and 1810. In this as well as other variations, movement of base joint 1813 mimics MCP joint movement and is capable of flexion, extension, abduction, adduction, and circumduction.

In operation, as shown in FIGS. 19 and 20, movement of a user's fingers, e.g., an index finger, middle finger, and thumb, from an open (FIG. 19) position to a closed, grasping position (FIG. 20), actuates finger slides 1806. Using the index finger as an example, actuation of index finger slide 1806 correspondingly articulates effector joints 1812A, 1812B, as described further below. Articulation of base joint 1813, correspondingly articulates effector base joint 1812C in the effector portion 1807, in the same fashion as described for the base joint in the finger loop variation. Cables (not shown) running from finger slides 1806 and base joint 1813 through handle portion 1805, shaft 1815, and effector palm 1816, are actuated by the user's finger movement to produce a corresponding movement of the effector portion 1807. Mirrored movement at the effector portion 1807 may be generally achieved by rotating the cables approximately 180.degree. as they travel through handle portion 1805, shaft 1815, and effector palm 1816. The shaft can be of varying length and can be rigid or flexible, as circumstances warrant.

Figure 21:
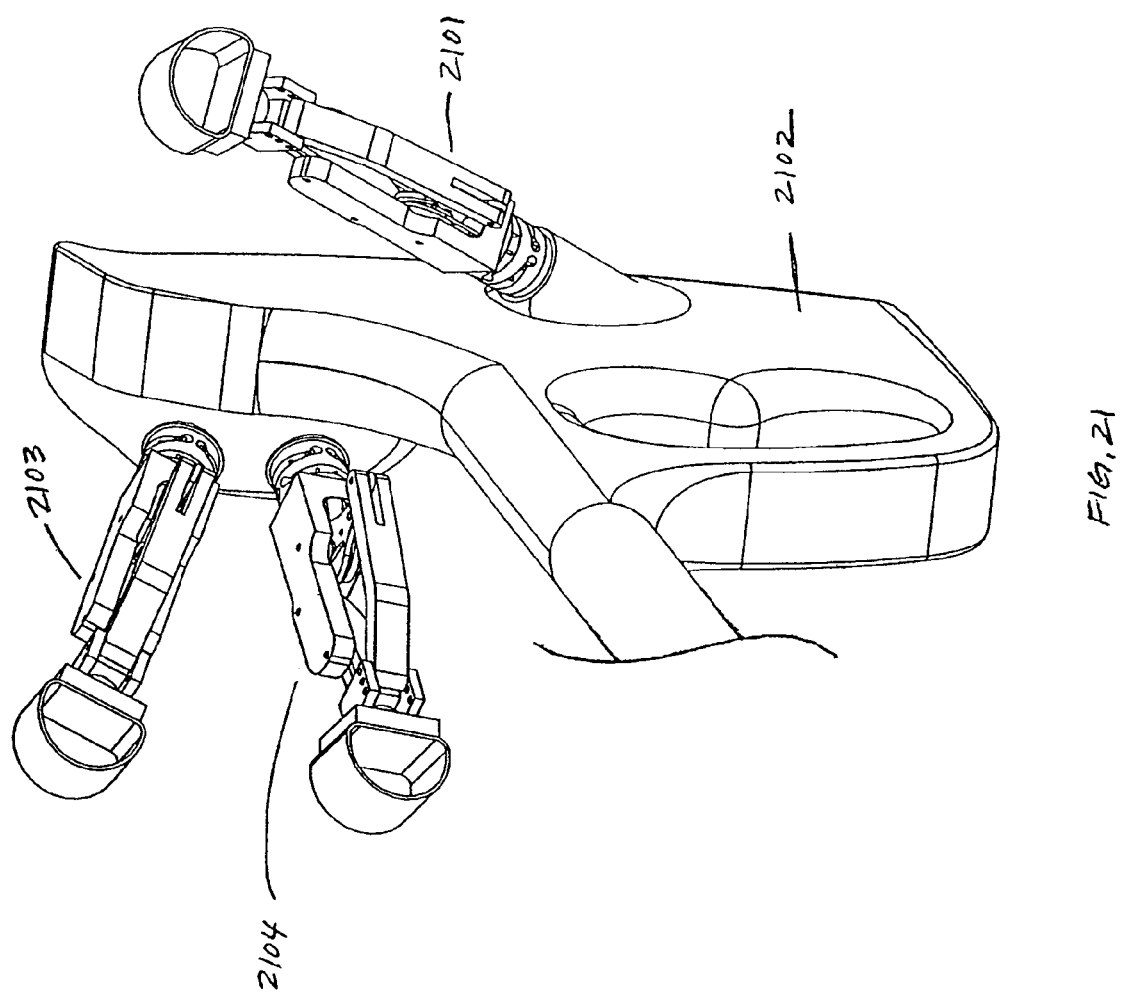
FIG. 21 is a perspective view of a handle of the hand-actuated device according to one variation of the invention.

As briefly mentioned above, the arrangement of the finger portions on the handle portion of the interface may vary to improve ergonomics or depending on factors such as user preference or the type of procedure involved. For example, as shown in FIG. 21, the thumb slide 2101 is mated to the handle portion 2102 at a position different from that shown in FIGS. 14-20. In a particularly ergonomic configuration, as illustrated in FIG. 21, the position of the thumb slide 2101 is lower than the index finger slide 2103 and middle finger slide 2104, and in some instances, also lies posterior to these slides.

The general configuration of the finger slides may vary depending on many user-associated factors such as ergonomics and user preference, but are usually configured to include a holder, a slider, a transmission rod, and a pulley lever, such that translational movement of the holder produces rotational movement of the pulley lever, which in turn moves connecting cables to actuate effector joints and links.

Figure 22:
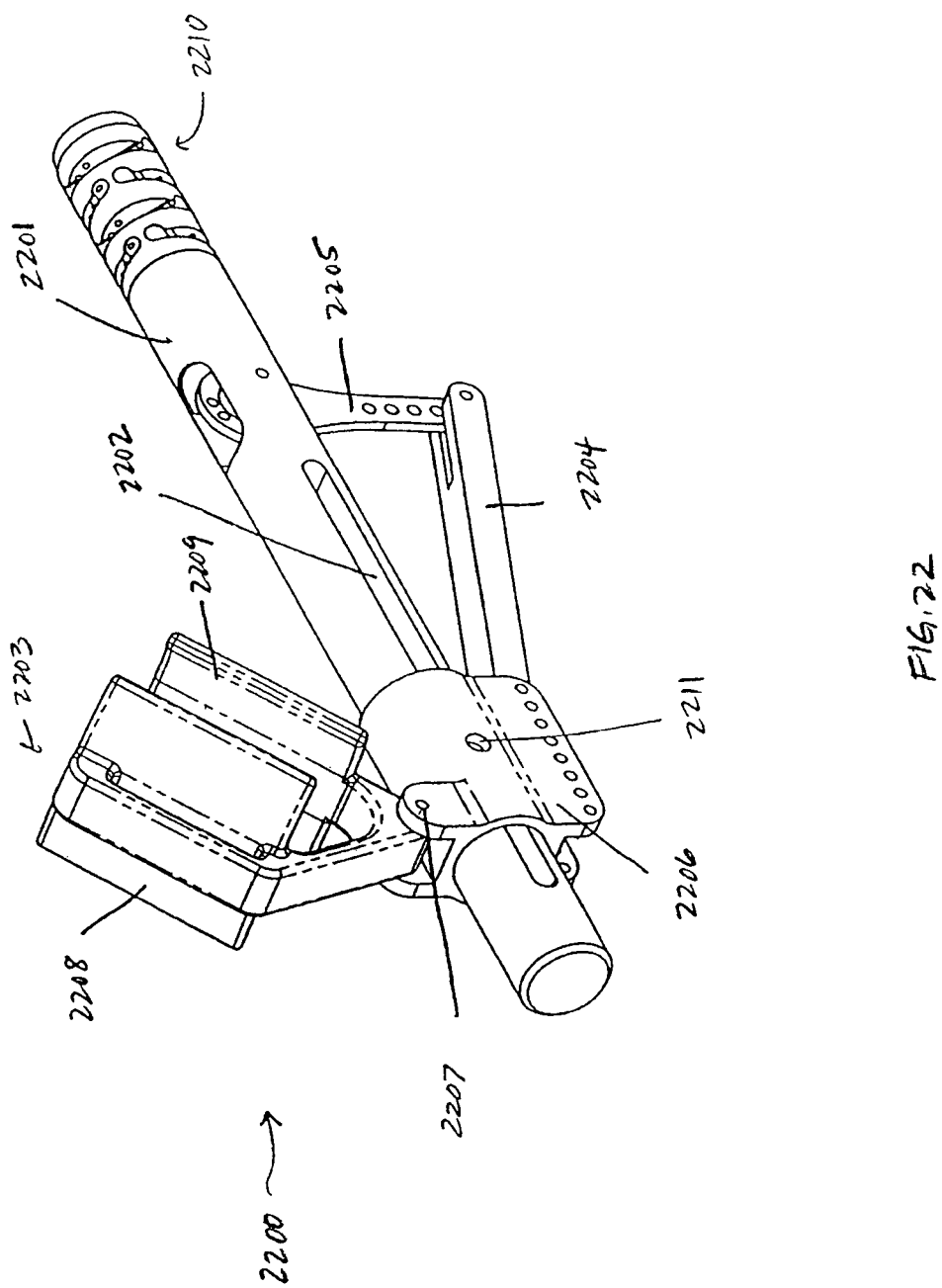
FIG. 22 is a side view of the slide mechanism according to one variation of the invention.

In the variation illustrated in FIG. 22, finger slide 2200 includes a housing 2201, a track 2202 along housing 2201, a holder 2203, a transmission rod 2204, a pulley lever 2205, and a slider 2206. Slider 2206 is coupled to housing 2201 by dowel 2211 placed through slider 2206 and track 2202 to prevent slider 2206 from rotating with respect to housing 2201. Holder 2203 is coupled to slider 2206 at pivotable hinge 2207 that accommodates finger flexion and extension. The tip of a digit may be placed in holder 2203, and upon flexion or extension of the PIP and DIP joints, movement of the holder 2203 causes translational movement of slide 2206 along track 2202. This slide movement translates translational movement of the transmission rod 2204 into rotational movement of pulley lever 2205, thereby pulling cables (not shown) connected to pulley lever 2205 to cause movement of the effector portion as further described below. The holder 2203 depicted in FIG. 27 has a top plate 2208 and bottom plate 2209 for removably securing the fingertip of a user. The holder configurations of this invention, however, not only include the structure shown in FIG. 27, but also contemplate loop-type structures 2310 (FIG. 23), or any configuration suitable for removably securing the fingertip of a user for actuation of the device. In this and other variations, base joint 2210 extends from housing 2201 and may be rigidly fixed to housing 2201 or formed integrally therewith. As previously described, joints such as base joint 2210 are configured to function similar to MCP joints having at least movement in two degrees of freedom. Finger slide actuation corresponds to articulation of DIP and PIP joints which are generally known to move in a single degree of freedom.

Figure 23:
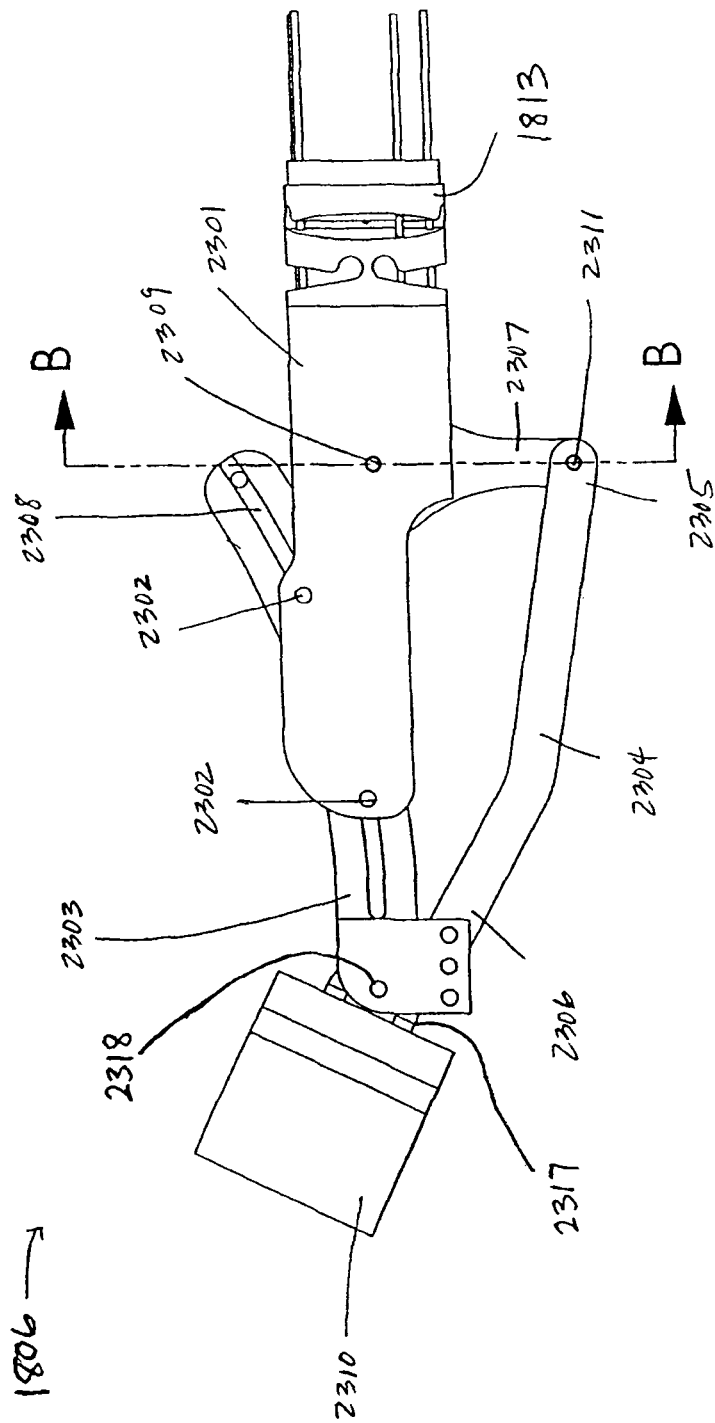
FIG. 23 is a side view of the slide mechanism according to FIG. 18.
Figure 24:
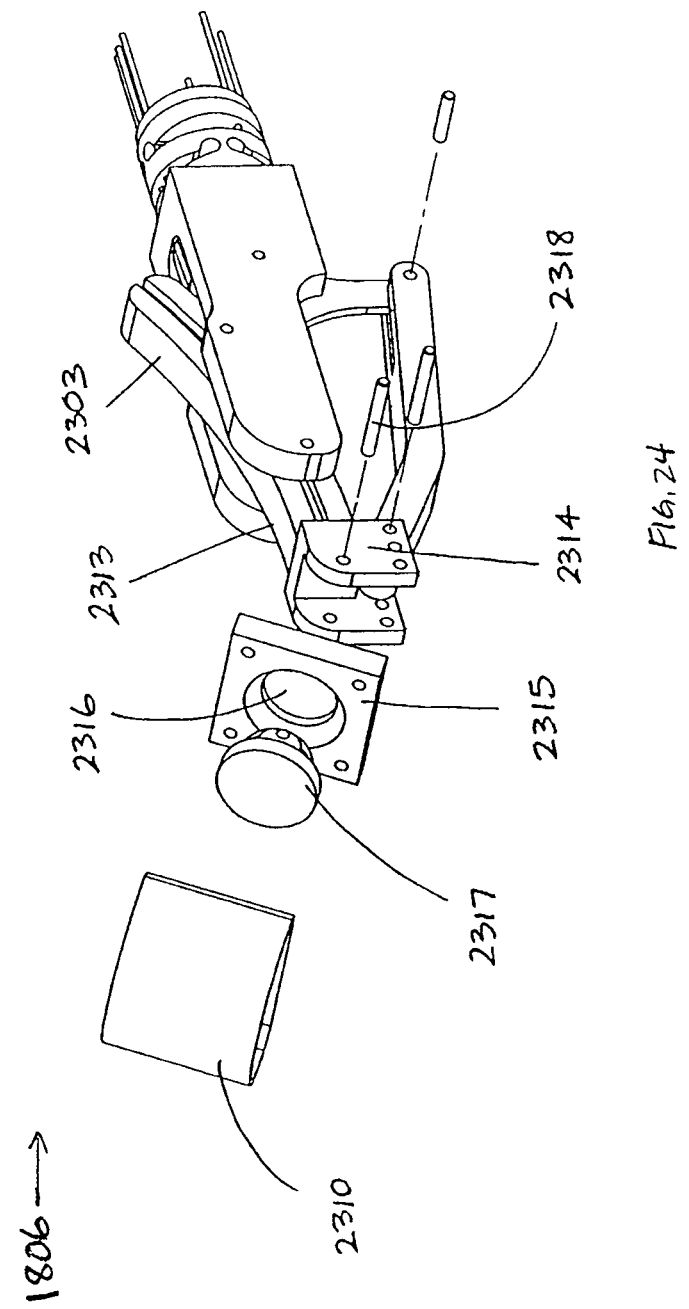
FIG. 24 is a perspective view of the slide mechanism of FIG. 23, partially disassembled.

Another finger slide variation is shown in FIGS. 23 and 24, and in FIGS. 18-21. In this variation, finger slide 1806 includes a housing 2301 with slide pins 2302, a curved slide 2303, a transmission rod 2304, a pulley lever 2307, a holder 2310, and pulleys (not shown). The provision of curved slide 2303 is particularly ergonomic because in operation the overall motion of the finger slide takes a curved path that mimics the path a user's fingertips make when the PIP and DIP joints are bent. Furthermore, use of this curved slide path more accurately mimics human finger movement because with this configuration, a user's DIP and PIP joints can be articulated without moving the MCP joint. For example, referring back to FIG. 20, actuation of effector joints 1812A and 1812B could easily occur independently of actuation of effector base joint 1812C. The curve of slide 2303 may be adapted to be a circular arc, ellipse, parabola, and the like, in order to achieve this motion.

With respect to other features of finger slide 1806, slide pins 2302 insert into track 2308 to couple curved slide 2303 to housing 2301. Pulley lever 2307 is pivotably connected to housing 2301 by a first dowel 2309. A transmission rod 2304 having a proximal end 2305 and a distal end 2306 operably connects pulley lever 2307 to holder 2310. A second dowel 2311 couples transmission rod proximal end 2305 to pulley lever 2307. At distal end 2306, transmission rod 2304 is pivotably connected to curved slide 2303 by a third dowel (not shown). In FIG. 23, a base joint 1813 that is rigidly fixed to housing 2301 is also shown.

In FIG. 24, the relationship of additional finger slide elements to each other is more clearly depicted. As shown in FIG. 24, finger slide 1806 includes a curved slide 2303 having a distal end 2313. Distal end 2313 is fixedly connected to bracket 2314. Plate 2315 has a cylindrical opening 2316 that receives mandrel 2317, such that plate 2315 can rotate about mandrel 2317. Mandrel 2317 is pivotally coupled to bracket 2314 by dowel 2318. Plate 2315 can thus both pivot and rotate relative to bracket 2314, i.e., it can pivot about dowel 2318 as well as rotate relative to mandrel 2317. Holder 2310 is secured to plate 2315 and thus can also pivot and rotate with respect to bracket 2314. This finger slide configuration is particularly ergonomic because it accommodates natural finger movement when the fingers are abducted. The ability of the finger holder to rotate relative to the slide, in particular, is advantageous as it more readily accommodates a combined flexion and abduction movement between fingers during which the fingertips naturally rotate slightly relative to one another.

Figure 25:
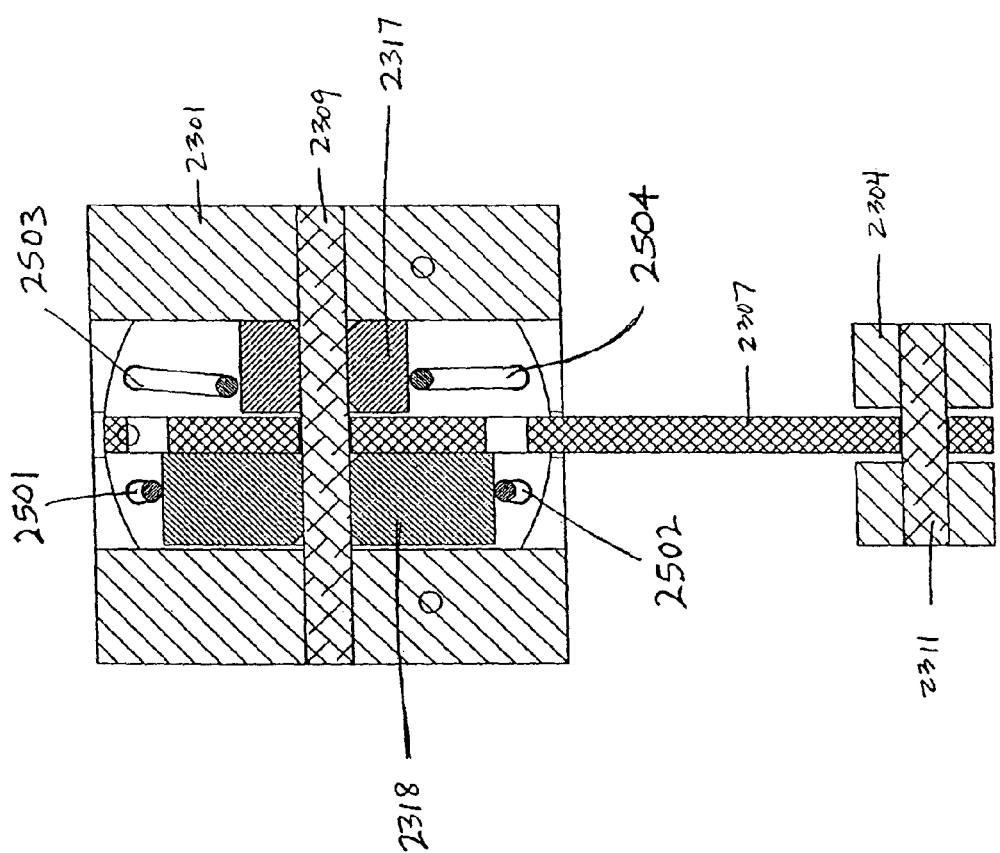
FIG. 25 is a cross-sectional view of the slide mechanism of FIG. 23, taken along line B-B, showing an end joint roller having twice the diameter of a middle joint roller.
Figure 26:
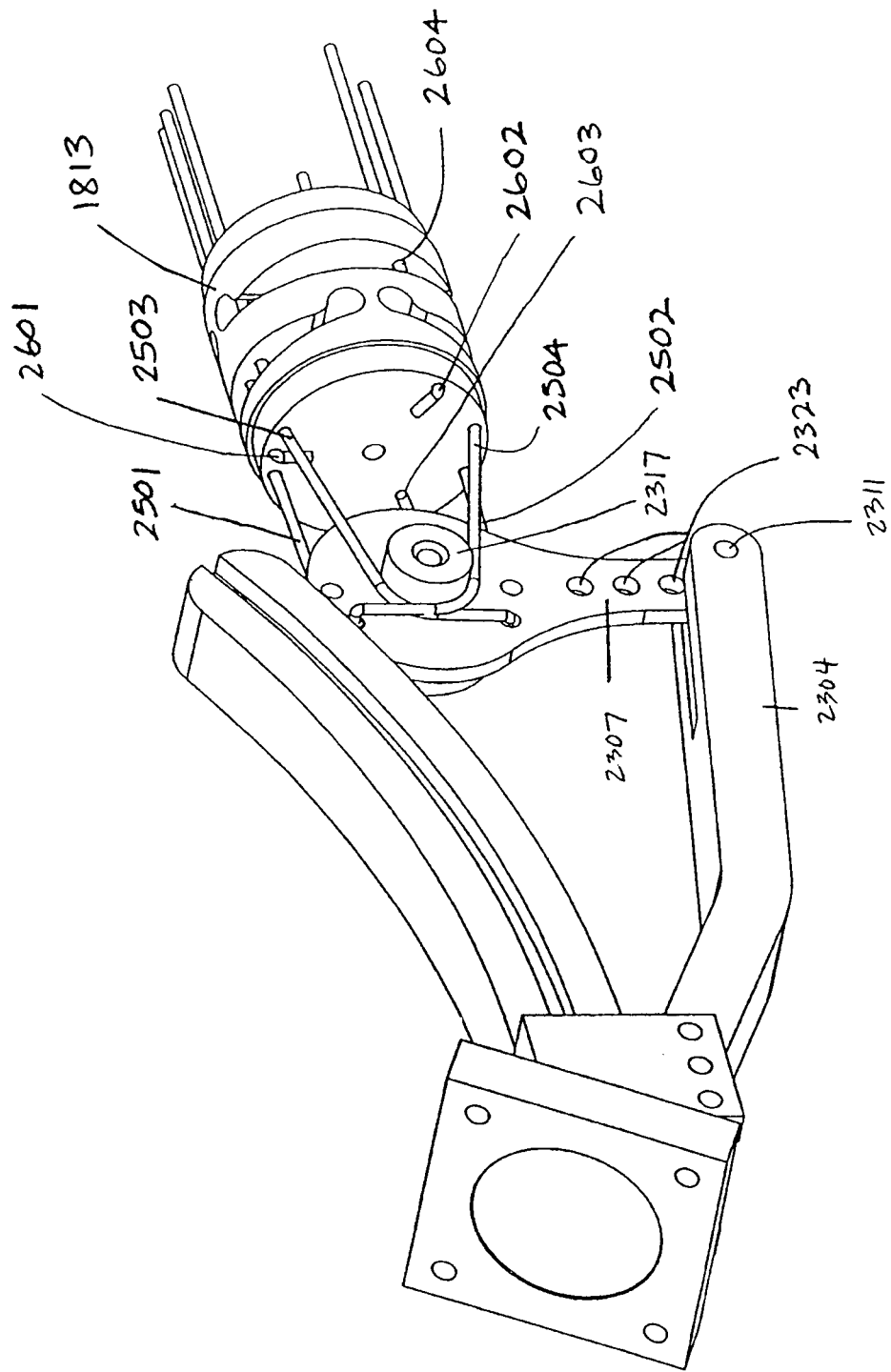
FIG. 26 is a perspective view of the slide mechanism of FIG. 23 showing the cable connections to the rollers and a base joint according to one variation of the invention.

The finger slide of FIG. 23 also includes cables for actuating movement of the effector portion as shown in the cross-section taken along line B-B in FIG. 25 and in FIG. 26. Cables 2503 and 2504 wrap around pulley 2317 and terminate in pulley lever 2307. Cables 2501 and 2502 wrap around pulley 2318 on the opposite side of pulley lever 2307 and similarly terminate in pulley lever 2307. In operation, flexion or extension of a user's finger at the DIP and PIP joints, e.g., an index finger, secured to the finger slide, causes a rotational movement of pulley lever 2307 which thereby freely pulls cables 2501 and 2502 about pulley 2318, and freely pulls cables 2503 and 2504 about pulley 2317. More specifically, when a user's index finger is flexed at the DIP and PIP joints, cable 2501 is pulled about pulley 2318 and cable 2503 is pulled about pulley 2317. When a user's index finger is extended at the DIP and PIP joints, cable 2502 is pulled about pulley 2318 and cable 2504 is pulled about pulley 2317. Cables 2501, 2502, 2503, and 2504 then pass through channels 2604 in base joint 1813 to articulate movement of effector joints (e.g., joints 1812A and 1812B in FIG. 30) as further described below.

The pulleys may be configured to rotate about dowel 2309 or may be fixedly attached to pulley lever 2307, and generally have diameters that vary from one another.

In some instances, it may be desirable to scale movement of the effectors in relation to movement occurring at the user interface. Typically, pulley diameters are selected so that the amount of cable pulled for a given rotation is equal to the cable that would be pulled if an articulating link were substituted in place of the pulley. Thus, because cables that actuate a most-distal effector link (e.g., 1811A in FIG. 20) usually travels farther than cables that actuate another distal effector link (e.g., 1811B in FIG. 20), the diameter of the pulley that controls the most distal effector link must be larger than that of the pulley that controls the distal effector link. For example, in FIG. 25, pulley 2318 is shown to have a diameter approximately twice that of pulley 2317. Scaling of effector movement can be further adjusted by varying the pulley diameters while retaining the same ratio of the pulley diameters relative to one another and/or varying the ratio of the pulley diameters relative to one another. In addition, although the pulleys in FIGS. 25-26 are circular, other pulley shapes may be employed to adjust movement of the effector joints. For example, a cam shape may be used to articulate an effector joint in a non-linear fashion.

Referring to FIG. 26, another way to scale effector movement is to adjust the position of transmission rod 2304 along the length of pulley lever 2307 by lifting distal end of transmission rod 2305 closer to pulley 2317 such that dowel 2323 inserts into one of dowel apertures 2317. Effector movements will be scaled down as distal end 2305 is positioned closer to pulley 2505. Other ways to scale movement of the effectors include, but are not limited to, the inclusion of additional spacer links and/or varying the cable channel pattern radius in the links, as previously discussed. In some instances, e.g., in industrial applications, reverse scaling may be desirable.

Movement of base joint 1813 is actuated by the user's fingers. As previously described, movement of base joint 1813 results in a corresponding movement at an effector base joint (e.g., 1812C in FIG. 20). The cables used to connect base joint 1813 to an effector base joint, cables 2601, 2602, and 2603, terminate as shown on base joint 2813 in FIG. 26. Cable termination at the effector portion will be further described below.

All cables leaving the finger portion of a user interface travel through a handle portion, shaft, and an effector palm before terminating at an effector link. As mentioned above, in order for movement to be mirrored at the distal end of the device, cables traveling from the proximal end are generally rotated approximately 180.degree. prior to terminating at the distal end. However, in certain applications, because a combination of mirrored and inverted movement may be desired, all cables do not necessarily have to be rotated. In addition, in single degree of freedom joints, e.g., a joint corresponding to a DIP or PIP joint, the cables do not have to be rotated 180.degree. in order to provide mirrored movement. The cables simply need to be moved to the other side of the pivot or hinge on one link of the pair relative to cable position on the other link of the pair.

Figure 27:
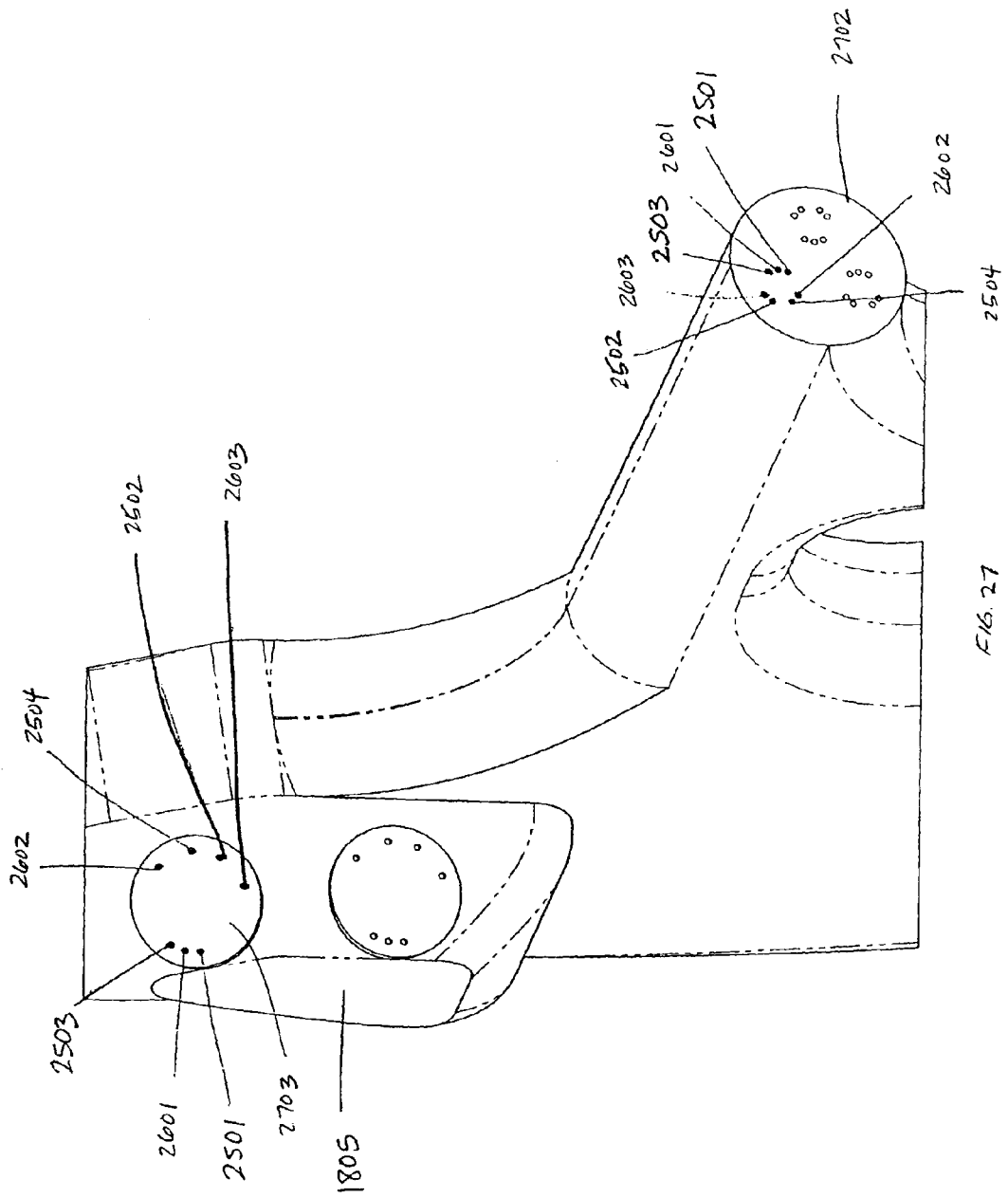
FIG. 27 is a perspective view of a handle showing routing of cables.

FIG. 27 depicts cable rotation through handle portion 1805 by noting the entry and exit points of cables in handle portion 1805. In FIG. 27, cables enter handle portion 1805 in the general pattern shown at a first area 2703. For example cable 2602 is shown to enter first area 2703 at approximately the 2 o'clock position, and 2603 at the 5 o'clock position. Upon exit at a second area 2702, a different cable pattern is seen. Instead of exiting at the 2 o'clock position, cable 2602 exits at approximately the 8 o'clock position, and for cable 2603, instead of exiting at the 5 o'clock position, it exits at approximately the 11 o'clock position. A rotation of 180.degree. is needed only if mirrored movement is desired. Otherwise, cables may be rotated in any manner to suit the intended use of the device.

Figure 28:
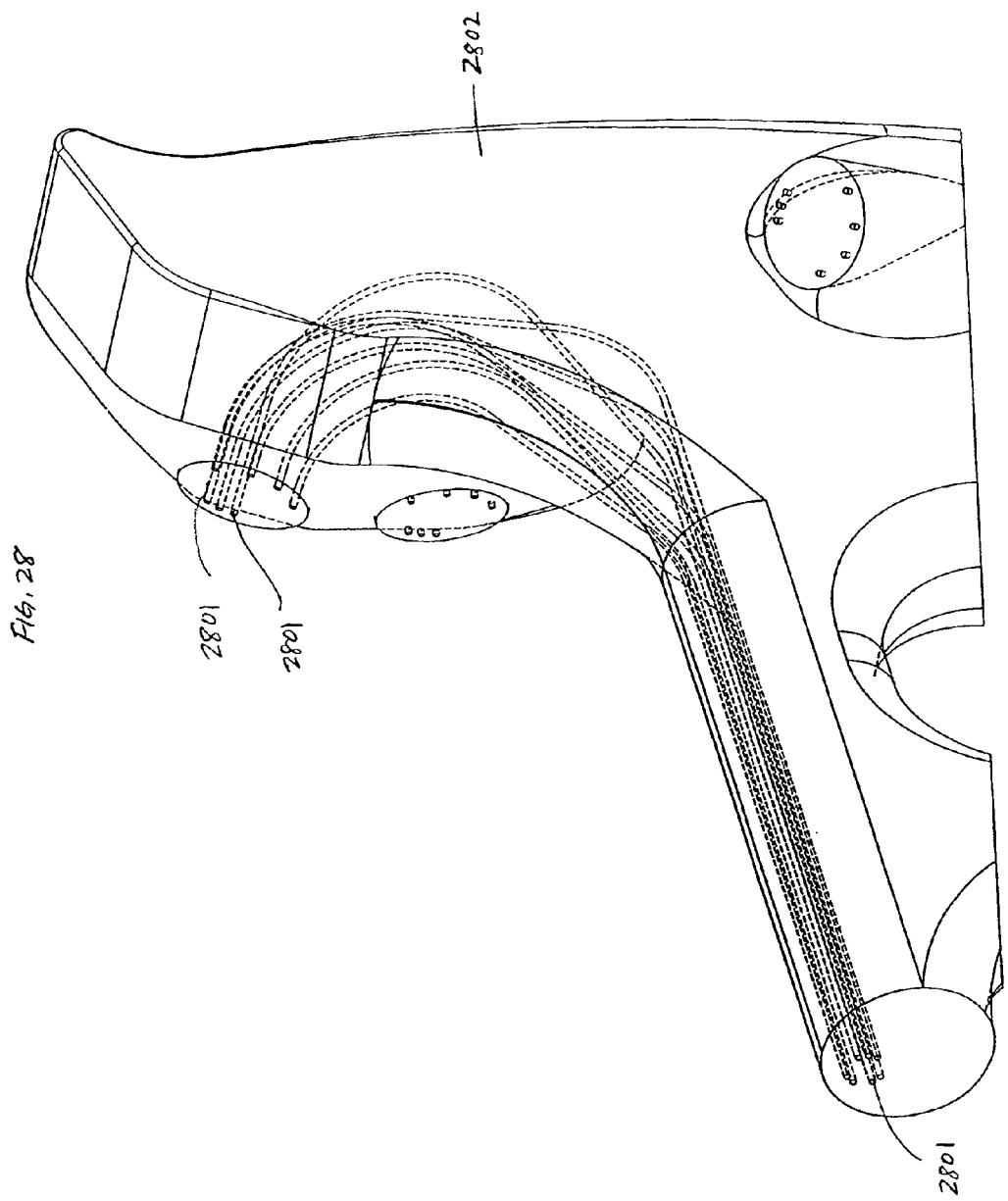
FIG. 28 is an expanded perspective view of a molded handle of a user hand interface according to one variation of the invention, with cables traveling through channels in the interface.
Figure 29:
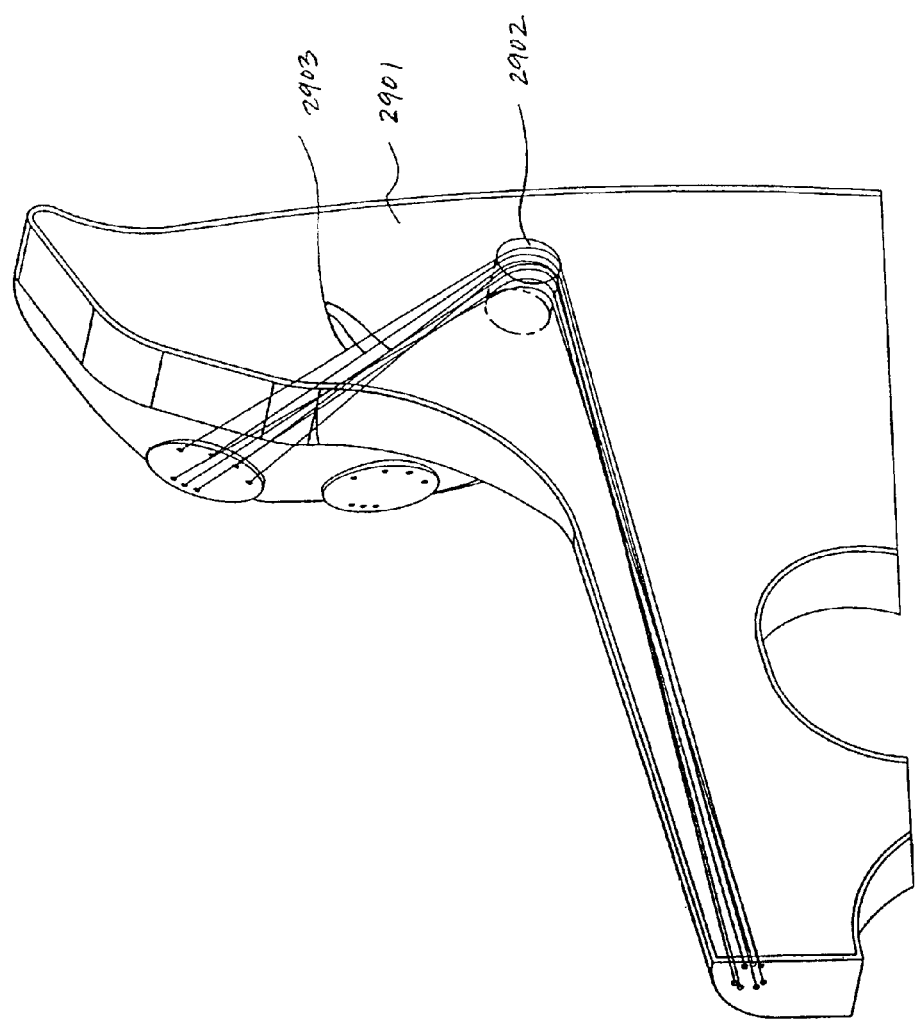
FIG. 29 is an expanded cross-sectional view of a hollow handle of a user hand interface according to another variation of the invention showing the cables being routed by a pulley.

The handle portion 2802 of the user hand interface may be a molded handle, as shown in FIG. 28, with channels or tubes 2801 for routing cables. In this variation, instead of rotating cables, the channels may be rotated or crossed to effect mirrored or inverted movement. In another variation, as shown in FIG. 29, the handle portion 2901 may be hollow and include a pulley 2902 for alignment and routing of cables 2903. The cables 2903 in this variation can be rotated (crossed) either before reaching pulley 2902, or after travel around pulley 2902. Materials that may be used to make the molded or hollow handles of this invention include those previously described for elongate links, as well as others that may be suitable for making medical devices.

Figure 30:
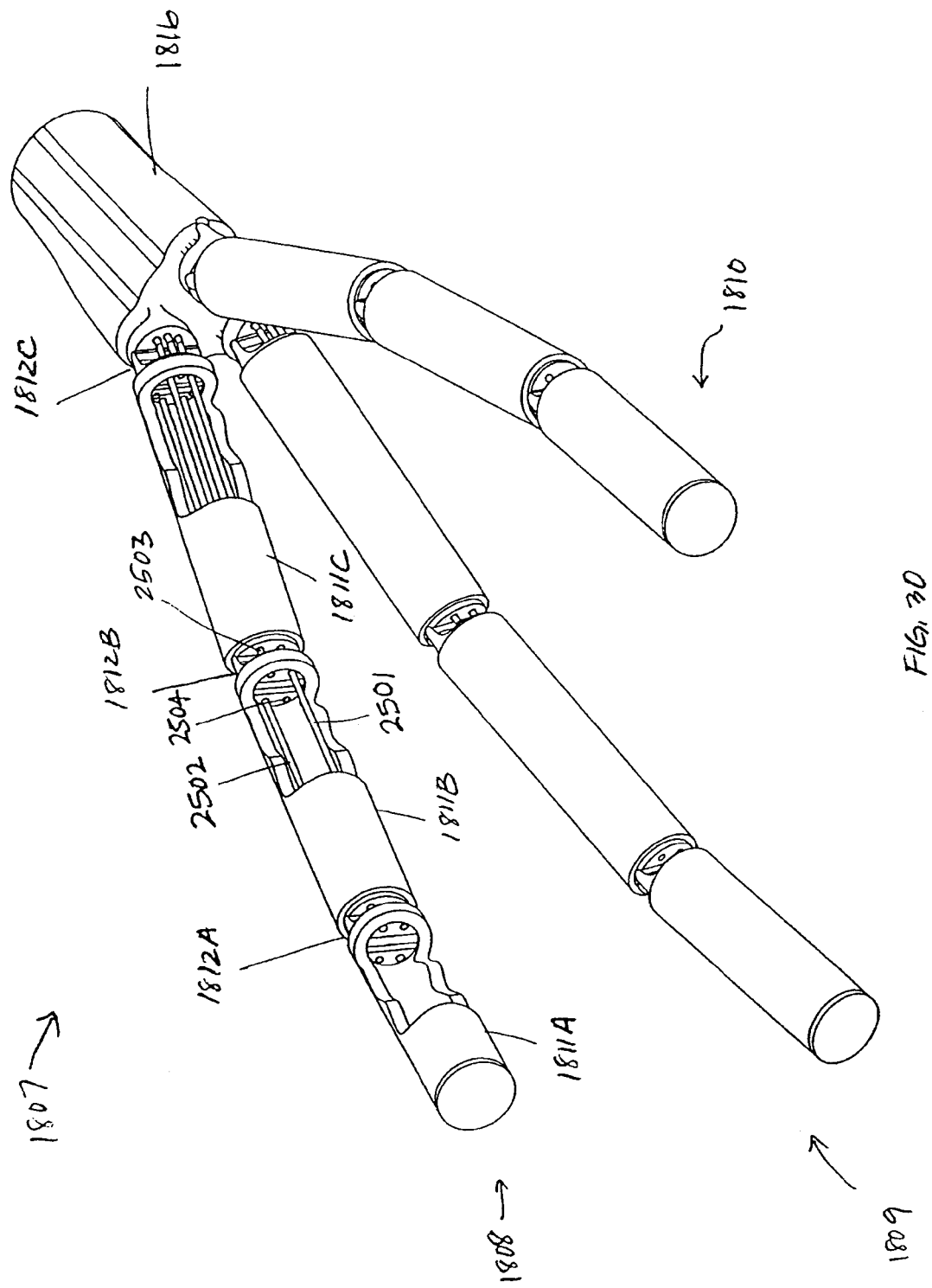
FIG. 30 is an expanded cutaway view of the effector portion of the hand-actuated apparatus of FIG. 14.

The effector portion of the device typically includes three effectors that correspond to a user's index finger, middle finger, and thumb, but any number of effectors may be included. As generally described, cables traveling from the user interface variously terminate at effector links to actuate effector movement. An understanding of joint articulation using a finger slide may be better obtained by viewing the cable termination points shown in FIG. 30 in conjunction with FIGS. 18-20. The effector portion depicted in FIG. 30 represents effector portion 1807 in FIGS. 18-20. Although the general structure and operation of effectors in the finger slide variation are being described, it is understood that this structure and operation also applies to the interface variation having finger loops.

In FIG. 30, effector 1808 corresponds to a user's index finger, and is generally configured to include an effector base joint 1812C, two effector joints 1812A and 1812B, and effector links 1811A, 1811B, and 1811C. Effector link 1811C corresponds to the proximal phalanx of an index finger; effector link 1811B corresponds to the middle phalanx of an index finger; and effector link 1811A corresponds to the distal phalanx of an index finger. Similarly, effector base joint 1812C corresponds to a MCP joint capable of movement in at least two degrees of freedom, effector joint 1812B corresponds to a PIP joint capable of movement in a single degree of freedom, and effector joint 1812A corresponds to a DIP joint, also capable of movement in a single degree of freedom. As depicted in FIG. 34, effector link 1811B, which is representative, is formed by securing links 3101 to the ends of a tube, although other methods of forming the effector links will be readily apparent.

Figure 31:
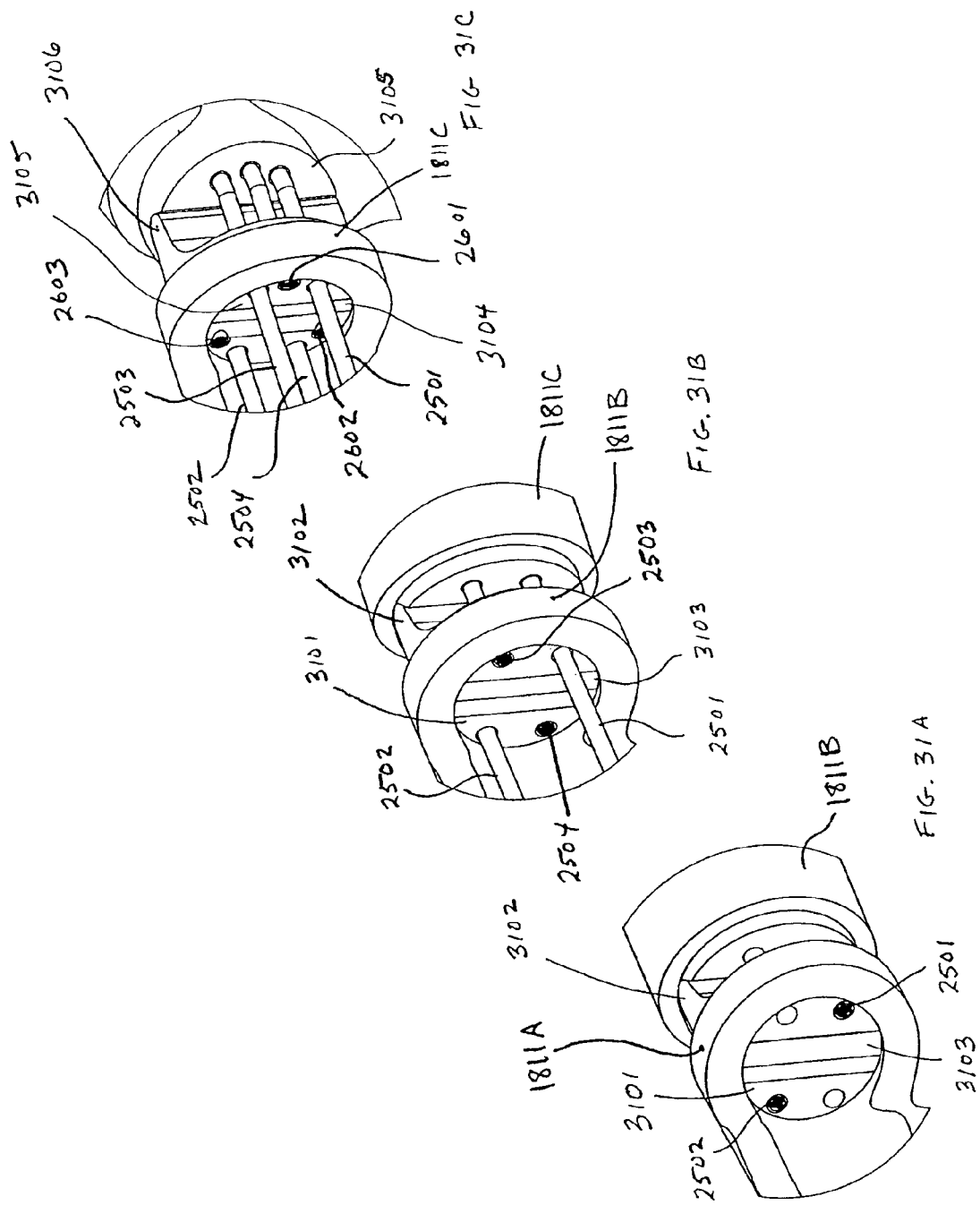
FIGS. 31A-31C are expanded cutaway views of the effector joints in FIG. 30.

Cables from the handle portion of the device are received through shaft (not shown) and are routed to the appropriate effector by effector palm 1816. Effectors emerge from effector palm 1816, as shown in FIG. 30 and other figures, that extends from the shaft. However, if desired, the effectors may be adapted to emerge from different points along the shaft or effector palm 1816 to form, e.g., a staggered or more spread out effector configuration. In this manner, a more or less hand-like effector portion can be made. Typically, cables 2501, 2502, 2503, and 2504 from the slider which actuate movement of effector joints 1812A and 1812B, terminate at one of the two effector links 1811A and 1811B. For example, as more clearly shown in FIG. 31A, cables 2501 and 2502 which are pulled around the larger pulley, and which articulate movement of effector joint 1812A, terminate in distal-most effector link 1811A. Cables 2503 and 2504 which are pulled around the smaller pulley, and which articulate effector joint 1812A, terminate in effector link 1811B, as shown in FIG. 31B. Likewise, cables 2601, 2602, and 2603 originating from base joint (1904 in FIG. 20) and which articulate movement of effector base joint 1812C, generally terminate at effector link 1811C, as depicted in FIG. 31C.

Figure 32:
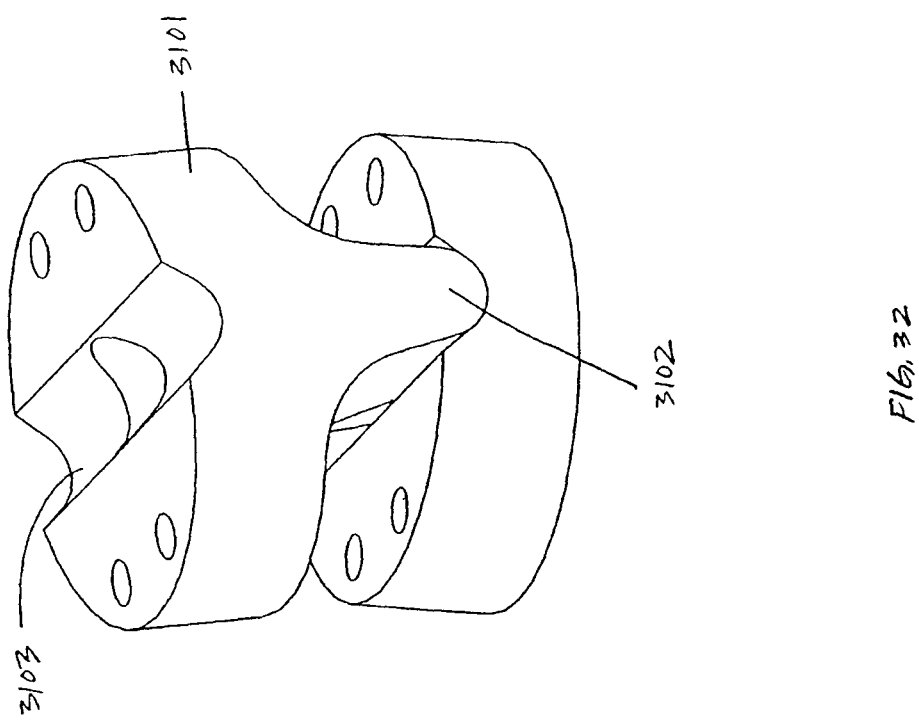
FIG. 32 is an expanded side view of the effector joints in FIGS. 31A and 31B with the joints vertically oriented.
Figure 33:
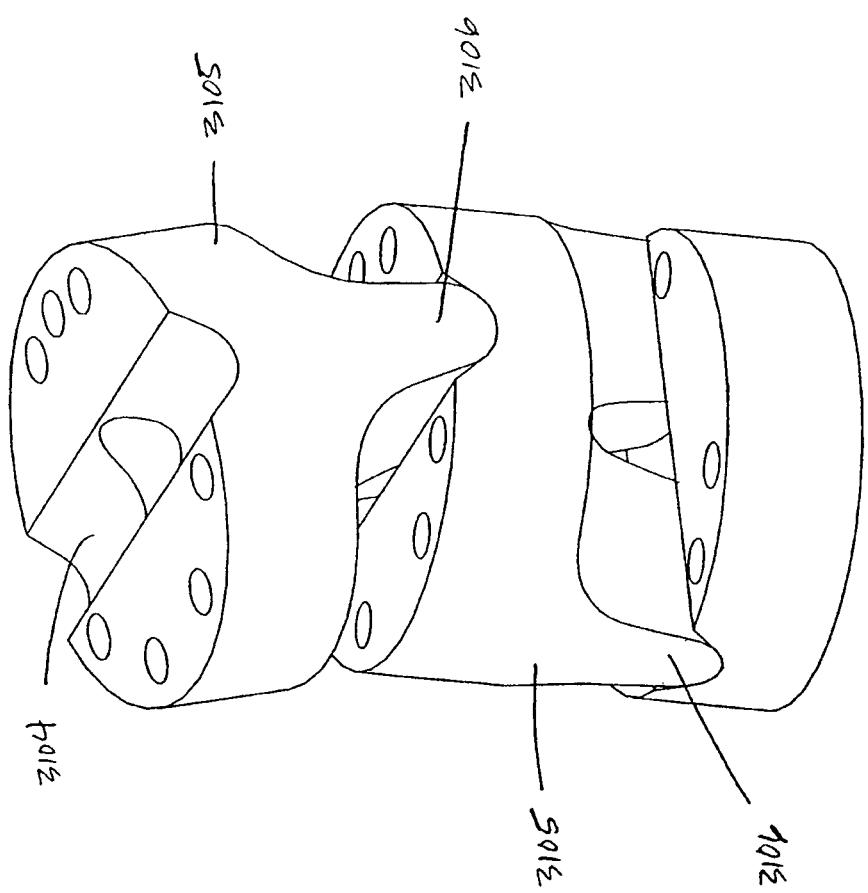
FIG. 33 is an expanded side view of the effector joint in FIG. 31C with the joints vertically oriented.

Effector joints 1812A-1812C are typically configured to have a range of motion that mimics the range of motion of MCP, PIP, and DIP joints, respectively. For example, effector base joint 1812C which corresponds to an MCP joint, is typically equipped to move in at least two degrees of freedom by including, e.g., two or more links 3105 each having a rib 3106 extending from the diameter of one surface of the link and having channels 3104 running across the diameter of their opposite surface. Channels 3104 are adapted to pivotably engage rib 3106 along the entire length of the channel, such that two links can pivot relative to one another about the axis of the channel. In effector base joint 1812C, the two links are positioned with their respective ribs oriented orthogonal to one another and with the rib of the most proximal link engaging a similar channel provided in effector palm 1816, in order to provide movement in two degrees of freedom. Distal effector joints 1812A and 1812B generally only require movement in a single degree of freedom. FIG. 33 is representative of effector base link 1812C also shown in FIGS. 30 and 31C. Another representative joint structure providing a single degree of freedom is depicted in FIGS. 31A-31B, and FIG. 32 and includes links 3101 having a rib 3102 extending from the diameter of one surface of the link and having a channel 3103 aligned with the extending rib on its other side. Channels 3103 are adapted to pivotably engage rib 3102 along the entire length of the channel, such that two links can pivot relative to one another about the axis of the channel, to provide a single degree of freedom.

Importantly, the finger portion of the interfaces described above may be configured to include a combination of finger slides and finger loops for articulation of effector joints. For example, because thumb joints can generally move somewhat independently from one another, a finger loop type finger portion may provide more accurate mimicking of human thumb joint movement at the effector. This is because finger loop input control allows for independent control of distal effector link movement, in contrast to finger slides which only allows coupled control of distal effector link movement. On the other hand, when DIP and PIP joints of fingers such as the index finger, middle finger, and ring finger, are articulated, they usually flex or extend together. Accordingly, it may be more suitable for finger slides to actuate effector movement for these fingers.

It is also understood that the hand-actuated devices may also adopt configurations that differ from the human hand. For example, in certain surgical applications, it may be desirable to shape the effector portion in such a way that it becomes a tool with functionality other than that of gripping of the hand.

In yet another variation, the articulating mechanism may be used for the endoscopic treatment of atrial fibrillation. In particular, the articulating mechanism of the invention can be adapted to facilitate the creation of ablative lesions in heart tissue, which has been demonstrated to be effective in treating atrial fibrillation, as described e.g. by Cox, J. L. (2000). "Minimally Invasive Maze-III Procedure," Operative Techniques in Thoracic and Cardiovascular Surgery Vol. 5(1):79-92; Simha et al. (2001). "The Electrocautery Maze—How I Do It," The Heart Surgery Forum Vol. 4(4):340-345; and Prasad et al. (2001). "Epicardial Ablation on the Beating Heart; Progress Towards an Off-Pump Maze Procedure," The Heart Surgery Forum Vol. 5(2):100-104; and as described in U.S. Pat. No. 6,161,543 to Cox et al. Such procedures can include epicardial or endocardial ablation, and many such procedures require accessing the posterior of the patient's heart, which can be difficult. The articulating mechanism of the invention can be configured with an ablative element, and together with its ability to form complex geometries; the mechanism can be readily navigated through the surrounding anatomy of the heart and easily positioned at various locations in or on the posterior of the heart to facilitate such ablation therapy.

Articulating mechanism 131 shown in FIG. 12A includes ablative element 125 connected to an electromagnetic energy source (not shown), such as an energy source which generated energy in radiofrequency (RF) or microwave frequency ranges. Such ablative elements are well known in the art, including those generally described in U.S. Pat. No. 6,471,696. The ablative element is mounted to links on the distal end 141 of the mechanism by way of attachment member 134 which is fittingly engaged with in channels 144 of links 142. The ablative element includes an insulated portion 127, typically formed of a thermoplastic elastomer, with longitudinally extending antenna or wire 129 for transmitting energy into tissue disposed therein. Other antenna or wire geometries, including helical coils, printed circuits, and the like are equally effective. Insulated conducting leads 136 and 137 are provided for connecting the energy source to the antenna or wire in a monopolar configuration. Bipolar configurations are also contemplated. Additional connectors 138 and 139 to the ablative element are also provided and can function in a variety of capacities, such as providing temperature or other sensors or probes, or to deliver a cooling medium to the element to cool the surrounding tissue and prevent extensive tissue damage, as is described, e.g., in U.S. Patent Application Publication No. US 2003/0078644 to Phan.

FIG. 12B shows another variation of the articulating mechanism of the present invention configured for ablation. In this variation, articulating mechanism 133, which is configured for bipolar use, includes distal end 143 having distal links 152 that contain opposing electrodes 159. The opposing electrodes are separated by channel 164. Insulated conducting leads, such as leads 166 and 167, connect each pair of electrodes to the energy source (not shown). When energized, energy is transmitted across the electrode pairs, creating ablative lesions in the surrounding tissue. Again, additional connections 168 and 169 are also provided to provide additional functions, including probes, sensors, and cooling fluids.

While the above variations use ablative elements that rely on electromagnetic energy, articulating mechanisms according to the invention can also be readily adapted to incorporate other methods of ablation known in the art. For example, the ablative element could be a cryogenic or ultrasonic probe, or ablative elements that use laser energy, or other known ablative techniques.

Epicardial ablative lesions can be created as shown in the example depicted in FIGS. 13A-13F. Access to the posterior of a patient's heart 929 by articulating mechanism 131 may be initially made through, e.g., a thoracotomy, mini-thoracotomy, or trocar port (e.g., a 5-10 mm port), placed in the anterior chest wall of a patient. The spacer element (not shown) of the articulating mechanism may serve the purpose of a fulcrum at the port. As the surgeon bends the proximal links that are outside of the patient, the distal links inside the patient mimic the curvature of the outside links in a reciprocal fashion, in order to wrap around the superior vena cava 933 (13A) and continue to surround and the pulmonary veins 935 (13B) as the articulating mechanism is simultaneously advanced. Once in position, as shown in FIG. 13B, the ablative element on the distal end of the articulating mechanism can then be activated to create a lesion, and as depicted here in particular, pulmonary encircling lesion 943 (FIG. 13C). In FIGS. 13D and 13E the articulating mechanism is shown being repositioned to extend downward from the pulmonary veins 935 to create a lesion 939 down to the mitral valve annulus that connects to prior-formed pulmonary encircling lesion 943 (FIG. 13F).

The invention also contemplates kits for providing various articulating mechanisms and associated accessories. For example, kits containing articulating mechanisms having different lengths, different segment diameters, and/or different types of surgical instruments, or different types of locking rods or malleable coverings may be provided. The kits may be tailored for specific procedures, e.g., endoscopy, retraction, or catheter placement, and/or for particular patient populations, e.g., pediatric or adult.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit and scope of the appended claims.

What is claimed is:

1. A medical instrument comprising:
    a distal articulation mechanism including a plurality of distal segments movable relative to each other;
    an actuatable element coupled to the distal articulation mechanism;
    a proximal articulation mechanism including a plurality of proximal segments, each proximal segment forming a pair with a corresponding distal segment from the plurality of distal segments;
    a user interface coupled to the proximal articulation mechanism, wherein the user interface manipulates the actuatable element; and
    multiple sets of cables, each set connecting the proximal segment and the corresponding distal segment of one of the pairs and terminating at the segments of the pair, such that movement of the proximal segment causes corresponding relative movement of the corresponding distal segment of the pair.

2. The medical instrument of claim 1, wherein the actuatable element includes a pair of jaws.

3. The medical instrument of claim 1, wherein the actuatable element includes a cutting element.

4. The medical instrument of claim 1, wherein the actuatable element includes a stapling device.

5. The medical instrument of claim 1, wherein the actuatable element includes an ablation device.

6. The medical instrument of claim 1, wherein the actuatable element includes a grasping device.

7. The medical instrument of claim 1, wherein the user interface includes a pivot mechanism.

8. The medical instrument of claim 7, wherein the proximal articulation mechanism is coupled to the user interface distally of the pivot mechanism.

9. The medical instrument of claim 7, wherein the proximal articulation mechanism is coupled to the user interface proximally of the pivot mechanism.

10. The medical instrument of claim 1, wherein the user interface includes a clamp handle.

11. The medical instrument of claim 10, wherein a portion of the proximal articulation mechanism extends through the clamp handle.

12. The medical instrument of claim 1, wherein the at least one set of cables is bifurcated to connect one of the proximal segments to a corresponding distal segment on each of two portions of the actuatable element such that movement of the proximal segment causes corresponding relative movement of both of the corresponding distal segments, whereby both of the portions of the actuatable element can be articulated into a common desired shape by manipulation of one or more proximal segments.

13. The medical instrument of claim 12, wherein the two portions of the actuatable element form a pair of jaws.

14. The medical instrument of claim 13, wherein at least one of the jaws includes an ablation element.

15. The medical instrument of claim 1, wherein the plurality of distal segments are generally aligned along a first common axis and the plurality of proximal segments are generally aligned along a second common axis, the first axis being non-parallel to the second axis.

16. The medical instrument of claim 15, wherein the first axis is generally perpendicular to the second axis.

17. The medical instrument of claim 1, wherein the plurality of distal segments are generally aligned along a first common axis and the plurality of proximal segments are generally aligned along a second common axis, the first axis being generally parallel to the second axis.

18. The medical instrument of claim 1, further comprising a spacer element between the proximal and distal articulation mechanisms.

* * * * *